(12) United States Patent
Brown et al.

(10) Patent No.: US 11,289,179 B1
(45) Date of Patent: Mar. 29, 2022

(54) AUTOMATED MEDICATION COMPLIANCE ASSURANCE SYSTEM

(71) Applicants: Steven Brown, Nashville, TN (US); Steven Dickerson, Nashville, TN (US)

(72) Inventors: Steven Brown, Nashville, TN (US); Steven Dickerson, Nashville, TN (US)

(73) Assignee: Compliance Strategies, LLC, Nashville, TN (US)

( * ) Notice: Subject to any disclaimer, the term of this patent is extended or adjusted under 35 U.S.C. 154(b) by 1071 days.

(21) Appl. No.: 15/428,999

(22) Filed: Feb. 9, 2017

Related U.S. Application Data

(60) Provisional application No. 62/293,586, filed on Feb. 10, 2016.

(51) Int. Cl.
*G16H 20/10* (2018.01)

(52) U.S. Cl.
CPC .................................. *G16H 20/10* (2018.01)

(58) Field of Classification Search
None
See application file for complete search history.

(56) References Cited

U.S. PATENT DOCUMENTS

| | | | |
|---|---|---|---|
| 2005/0267356 A1* | 12/2005 | Ramasubramanian | ..................... G06F 19/3462 600/411 |
| 2014/0149131 A1* | 5/2014 | Bear | ...................... G16H 20/10 705/2 |
| 2015/0100343 A1* | 4/2015 | Siedlecki | ............ G06F 19/3456 705/2 |

OTHER PUBLICATIONS

Lam, Medication Adherence Measures: An Overview, Hindawi Publishing Corporation, BioMed Research International, vol. 2015, Article ID 217047, Available at http://dx.doi.org/10.1155/2015/217047 (Year: 2015).*

National Center for Injury Prevention and Control, Opioid Painkiller Prescribing, Jul. 2014, CDC Vital Signs, US Department of Health and Human Services Centers for Disease Control, obatined from https://www.cdc.gov/vitalsigns/opioid-prescribing/index.html, last accessed Feb. 3, 2017, pp. 1-4.

(Continued)

*Primary Examiner* — Rachelle L Reichert
(74) *Attorney, Agent, or Firm* — Patterson Intellectual Property Law, P.C.; Edward D. Lanquist, Jr.

(57) ABSTRACT

Provided is a system providing a solution for improving prescription drug compliance monitoring and compliance. Prescription drug compliance monitoring may be achieved by using patient's electronic device to initiate secure digital imaging. Medications may be dispensed in containers with pre-printed encoded unique identifiers and markings. The patient may use the digital camera in their smart phone to take a picture of the dispensed blister pack which may be processed and analyzed. Analysis may include assessment of the number of pills taken from and remaining in the uniquely identified blister pack. Package identification and consumption information may then be linked with other prescription information to determine if the observed rate of use is compliant with the legal prescription and to document that the imaged medication package is the same as the dispensed medication package. Data may also be linked with pharmacologic and clinical data to categorize risk and urgency of misuse.

21 Claims, 31 Drawing Sheets

(56) References Cited

OTHER PUBLICATIONS

E. H. Crane, Highlights of the 2011 Drug Abuse Warning Network (DAWN) Findings on Drug-Related Emergency Department Visits, Feb. 22, 2013, Substance Abuse and Mental Health Services Administration, obtained from http://archive.samhsa.gov/data/2k13/DAWN127/sr127-DAWN-highlights.htm, last accessed Feb. 9, 2017, pp. 1-7.

DEA Strategic Intelligence Section, 2015 National Drug Threat Assessment Summary, 2015, US Department of Justice Drug Enforcement Administration, obtained from https://www.dea.gov/docs/2015%20NDTA%20Report.pdf, last accessed Feb. 3, 2017, p. ii.

National Center for Injury Prevention and Control, Policy Impact—Prescription Painkiller Overdoses, Nov. 2011, US Department of Health and Human Services Centers for Disease Control, obtained from https://www.cdc.gov/drugoverdose/pdf/policyimpact-prescriptionpainkillerod-a.pdf, last accessed Feb. 9, 2017, pp. 1-12.

C. Gounder, Who is responsible for the pain-pill epidemic, New Yorker, Nov. 8, 2013, obtained from http://www.newyorker.com/business/currency/who-is-responsible-for-the-pain-pill-epidemic, last accessed Feb. 9, 2017, pp. 1-6.

Coalition Against Insurance Fraud, Prescription For Peril—How Insurance Fraud Finances Theft and Abuse of Addictive Prescription Drugs, Dec. 2007, obtained from http://www.insurancefraud.org/downloads/drugDiversion.pdf, last accessed Feb. 3, 2017, pp. 1-75.

G. White, H. G. Birnbaum, M. N. Mareva, M. Daher, S. Vallow, J. Schein and N. Katz, Direct costs of opioid abuse in an insured population in the United States, Journal of managed care pharmacy: Journal of Managed Care Pharmacy, Jul./Aug. 2005, 11, pp. 469-479.

P. J. Christo, L. Manchikanti, X. Ruan, M. Bottros, H. Hansen, D. R. Solanki, A. E. Jordan and J. Colson, Urine Drug Testing in Chronic Pain, Pain physician, Mar./Apr. 2011, 14, pp. 123-143.

C. M. Viscomi, M. Covington and C. Christenson, Pill counts and pill rental: unintended entrepreneurial opportunities. The Clinical Journal of Pain, 2013, 29, 623-624.

L. Osterberg and T. Blaschke, Adherence to medication, The New England Journal of Medicine, Aug. 4, 2005, 353:5, pp. 487-497.

New England Healthcare Institute, Thinking Outside the Pillbox a System-wide Approach to Improving Patient Medication Adherence for Chronic Disease, Aug. 2009, New England Healthcare Institute, 21, obtained from http://www.nehi.net/writable/publication_files/file/pa_issue_brief_final.pdf, last accessed Feb. 3, 2017, pp. 1-21.

M. C. Roebuck, J. N. Liberman, M. Gemmill-Toyama and T. A. Brennan, Medication Adherence Leads to Lower Health Care use and Costs Despite Increased Drug Spending, Health affairs 30, No. 1, Jan. 2011, pp. 91-99.

Agency for Healthcare Research and Quality, 30-Day Readmission Rates to U.S. Hospitals, Healthcare Cost and Utilization Project (HCUP), US Department of Health and Human Services Agency for Healthcare Research and Quality, obtained from https://www.hcup-us.ahrq.gov/reports/infographics/HCUP-hospital-readmission-infographic-final.pdf, last accessed Feb. 9, 2017, 1 page.

M. L. Barrett, L. M. Wier, H. J. Jiang and C. A. Steiner, All-Cause Readmissions by Payer and Age, 2009-2013: Statistical Brief #199, Healthcare Cost and Utilization Project (HCUP) Statistical Briefs, Dec. 2015, pp. 1-13.

\* cited by examiner

AUTOMATED MEDICATION COMPLIANCE ASSURANCE SYSTEM

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application claims benefit of U.S. Provisional Patent Application No. 62/293,586, filed Feb. 10, 2016, and which is hereby incorporated by reference.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to providing an automated medication compliance assurance system.

Misuse, abuse, and diversion of prescription medications are major problems in the United States today. According to the Centers for Disease Control and Prevention (CDC), 46 people die every day from overdoses of prescription painkillers (NATIONAL CENTER FOR INJURY PREVENTION AND CONTROL, Opioid Painkiller Prescribing) over 1,000 people end up in Emergency Departments (E. H. CRANE, Highlights of the 2011 Drug Abuse Warning Network (DAWN) Findings on Drug-Related Emergency Department Visits). Drug overdose was the leading cause of injury death in 2013 and, among people 25 to 64 years old, drug overdoses caused more deaths than motor vehicle traffic crashes (DEA STRATEGIC INTELLIGENCE SECTION, 2015 National Drug Threat Assessment Summary).

For every opioid death in 2008, the CDC estimates that there were 825 non-medical users. (NATIONAL CENTER FOR INJURY PREVENTION AND CONTROL, Policy Impact—Prescription Painkiller Overdoses) This translates to over 12 million nonmedical prescription drug abusers in 2008 alone. According to one New Yorker article, "By 2010, the United States, with about five percent of the world's population, was consuming ninety-nine percent of the world's hydrocodone (the narcotic in Vicodin), along with eighty percent of the oxycodone (in Percocet and OxyContin), and sixty-five percent of the hydromorphone (in Dilaudid)." (C. GOUNDER, Who is responsible for the pain-pill epidemic).

The estimated economic impact of prescription drug diversion on healthcare costs was 72.5 Billion dollars per year as of 2007 (COALITION AGAINST INSURANCE FRAUD, Prescription For Peril—How Insurance Fraud Finances Theft and Abuse of Addictive Prescription Drugs). Opioid abusers generate direct health care costs that are 8.7 times higher than non-abusers (WHITE et al., Direct costs of opioid abuse in an insured population in the United States, Journal of managed care pharmacy).

In response, the Drug Enforcement Agency (DEA) has increased controls on hydrocodone-containing compounds by reclassifying them as Schedule II of the Controlled Substance Act. The Center for Disease Control (CDC) has mounted a major public health campaign to reduce the impact of opioid and benzodiazepine misuse, abuse, and diversion that includes roles for state-based prescription drug monitoring programs (PDMP), State Legislatures, Pharmacy Benefits Manages (PBM), and health care providers.

Healthcare providers attempt to control prescription drug misuse, abuse, and diversion via methods including narcotics contracts, urine drug testing, and short-notice return visits for pill counts. These methods alone are not enough. Narcotics contracts may not be either effective or enforceable. Urine drug testing has significant shortcomings including an inability to determine dosing compliance and concerns about being profit-driven (CHRISTO et al., Urine drug testing in chronic pain). Visits for pill counts are costly and can be circumvented by "pill-renting" from illicit opioid dealers prior to the visit (VISCOMI et al., Pill counts and pill rental: unintended entrepreneurial opportunities).

In short, existing methods for healthcare providers to control misuse, abuse, and diversion can be expensive, inconvenient, easily defeated, and/or inaccurate.

A second major problem includes the health and economic impacts of medication non-adherence in the treatment of chronic disease in the United States. An estimated one third to one half of all patients in the U.S. do not take their medications as prescribed by their doctors. (OSTERBERG et al., Adherence to medication). The New England Healthcare Institute (NEHI) estimates that non-adherence along with suboptimal prescribing, drug administration, and diagnosis could result in as much as $290 billion per year in avoidable medical spending, or 13 percent of total health care expenditures. (NEW ENGLAND HEALTHCARE INSTITUTE, Thinking Outside the Pillbox A System-wide Approach to Improving Patient Medication Adherence for Chronic Disease).

Poor adherence often leads to preventable worsening of disease and increased healthcare costs, particularly for patients with chronic illnesses. Roebuck et al examined the prescription spending and overall medical spending comparing adherent and non-adherent patients with congestive heart failure, hypertension, diabetes and dyslipidemia. They found that adherent patients had significantly reduced overall medical spending per year for all four conditions: ~$8000 less medical spending per year for congestive heart failure patients, ~$4000 less medical spending per year for diabetes and hypertension patients and ~$1000 less medical spending per year for patients with dyslipidemia. (ROEBUCK et al., Medication adherence leads to lower health care use and costs despite increased drug spending).

Non-adherence has been shown to result in $100 billion per year in excess hospitalizations alone (OSTERBERG et al., Adherence to medication) Readmissions within 30 days are particularly common, expensive and potentially avoidable. For example, in 2010 25% of patients admitted for exacerbations of congestive heart failure and 22% of patients admitted for schizophrenia were readmitted within 30 days. (AGENCY FOR HEALTHCARE RESEARCH AND QUALITY, HCUP-hospital-readdmission-infographic-34-51-12-Final(s)). In 2013, average readmission costs ranged between $10,000 per readmission of uninsured patients and $14,000 for readmission of patients with private insurance totaling over $50 billion in potentially avoidable costs. (BARRETT et al., *All-Cause Readmissions by Payer and Age, 2009-2013: Statistical Brief* #199).

Identifying and effectively intervening in cases of non-adherence or mis-adherence is challenging. A common method relies on analysis of pharmacy prescription fill patterns. This data may not be available for weeks or months after instances of non-adherence and provides only 30-90-day summary snapshots of prescription compliance behaviors. Interventions typically rely on counseling during clinical encounters or with dispensing pharmacists, relatively rare events in the course of a patient's daily routine. Other intervention methods include direct outreach to "at risk" patients at home via phone calls. Direct outreach can be effective but requires professional high wage staff.

BRIEF SUMMARY OF THE INVENTION

Various embodiments of the present invention provide systems, apparatuses, and methods for providing automated medication compliance assurance.

The present disclosure discusses an application, an apparatus, a system, and an integrated technology-service solution to improve prescription drug compliance monitoring, usage verification, and/or misuse verification (collectively referred to herein as conformance) at a low cost. In its most basic form, prescription drug monitoring conformance may be achieved by using the patient's own cell phone to initiate secure digital imaging, telemedicine, and computer-based scrutiny of dispensed medications over the course of the prescription.

In addition to compliance, one or more embodiments of the present disclosure may enable monitoring, tracking, and confirming or denying adherence to a prescription plan or schedule. Adherence and compliance are two words that are commonly used when it comes to healthcare, and these two words are often seen to be used synonymously at times. Yet it may be inaccurate to do so in certain instances. Adherence may refer to a patient, him or herself, adhering to the proper practices of medicine. Compliance may be viewed as when the patient follows the instructions of the doctor. Adherence empowers the patient thereby becoming co-equal to the doctors. Compliance may sometimes be viewed as a paternalistic and condescending attitude towards medicine. Adherence may offer more advantages than compliance in various scenarios.

Although described herein with reference to compliance, it should be appreciated that usage of the term compliance herein may include one or more embodiments relating to adherence as previously described, and not merely to compliance verification. As such, use of the term compliance herein may include one or more acts or verification relating to adherence.

In one exemplary embodiment, narcotics may be dispensed in blister packs with pre-printed encoded unique identifiers and markings to aid image analysis, security, and prescription control. In one embodiment, the encoded unique identifiers and markings may be placed on a product at time of packaging. In alternative or addition to the encoded unique identifier being placed on a product at time of manufacture, the encoded unique identifier may be affixed or otherwise associated with a container after time of packaging. At various intervals, the patient may use his or her digital camera built into their smart phone to take a picture of the dispensed blister pack. The image may be securely electronically sent to a Service Provider for processing and analysis. Analysis may include automated, semi-automated, or manual assessment of the number of pills taken from and remaining in the uniquely identified blister pack. This package identification and consumption information may then be linked with other prescription information including dispensed package identifier, medication issuance date, and instruction for use to determine if the observed rate of use is compliant with the legal prescription and to document that the imaged medication package is the same as the dispensed medication package. Package and consumption information can also be linked with pharmacokinetic, pharmacodynamic and other relevant data such established indications and known off-label uses to help risk stratify medication misuse events.

Monitoring of non-narcotic prescription compliance may be achieved with reduced security precautions. In this use scenario, computer vision may be used to identify potential compliance issues, either in tandem with direct outreach phone calls, or as a screening trigger for automated interventions such as reminders or direct outreach by a trained professional.

A multitude of benefits may be derived, either in whole or in part, through the use of systems and methods consistent with the present disclosure. For example, immediate payback may include (i) reduced healthcare costs directly related to reduced return visits for narcotic pill counts, reduced readmission rates for chronic diseases exacerbation (ii) enhanced compliance screening at low cost with better targeting of human-based interventions may be achieved, and (iii) data regarding patterns of medication use may be of interest to pharmaceutical companies and health insurers.

Medium-term paybacks may include (i) reduced healthcare costs relating to reduced abuse—e.g., "bending the curve" of the 8.7-fold healthcare cost increase of opioid abusers, (ii) improved health and well-being relating to reduced misuse, abuse, and diversion, and (iii) improved health and reduced healthcare spending for noncompliant patients with chronic diseases due to improved compliance.

One aspect of the present disclosure provides a system for automated medication compliance assurance for a patient. The system includes a portal configured to receive monitoring data (and/or metadata) relating to the patient and to transmit a monitoring plan request, a compliance service configured to receive the monitoring plan request, the compliance service being further configured to generate and store a monitoring schedule based on the received monitoring plan request, and an electronic device having a data capture apparatus, the data capture apparatus being configured to obtain data associated with a medication container, the medication container being configured to provide indicia associated with a state of at least a portion of the medication container. The compliance service is further configured to determine a patient medication usage metric based at least in part on an analysis of the data associated with the medication container, and the compliance service is configured to determine a medication compliance status by comparing the patient medication usage metric to an expected utilization associated with the monitoring schedule associated with a prescription or other pertinent data (e.g. established common patterns for particular medications).

Another aspect of the present disclosure provides a method of providing patient medication compliance assurance. The method includes steps of receiving monitoring data relating to the patient, transmitting a monitoring plan request to a compliance service, receiving the monitoring plan request at the compliance service and generating a monitoring schedule based at least in part upon the received monitoring plan request, obtaining data associated with a medication container by an electronic device configured to provide indicia associated with a state of at least a portion of the medication container, determining a patient medication usage metric based at least in part upon an analysis of the data associated with the medication container, and determining a medication compliance status by comparing the patient medication usage metric to an expected utilization associated with the monitoring schedule.

A further aspect of the present disclosure provides an apparatus for providing medication compliance service assurance for a patient. The apparatus includes a communications unit configured to receive a monitoring plan request relating to the patient and to obtain data associated with a medication container from an electronic device, the data containing an identifier associated with a state of at least a portion of the medication container, and a data processing component configured to (i) determine a patient medication usage metric based at least in part upon an analysis of the data associated with the medication container, and (ii) determine a medication compliance status by comparing the patient medication usage metric to an expected utilization associated with the monitoring schedule.

Numerous other objects, features, and advantages of the present invention will be readily apparent to those skilled in the art upon a reading of the following disclosure when taken in conjunction with the accompanying drawings.

DETAILED DESCRIPTION OF THE INVENTION

Figure 1:
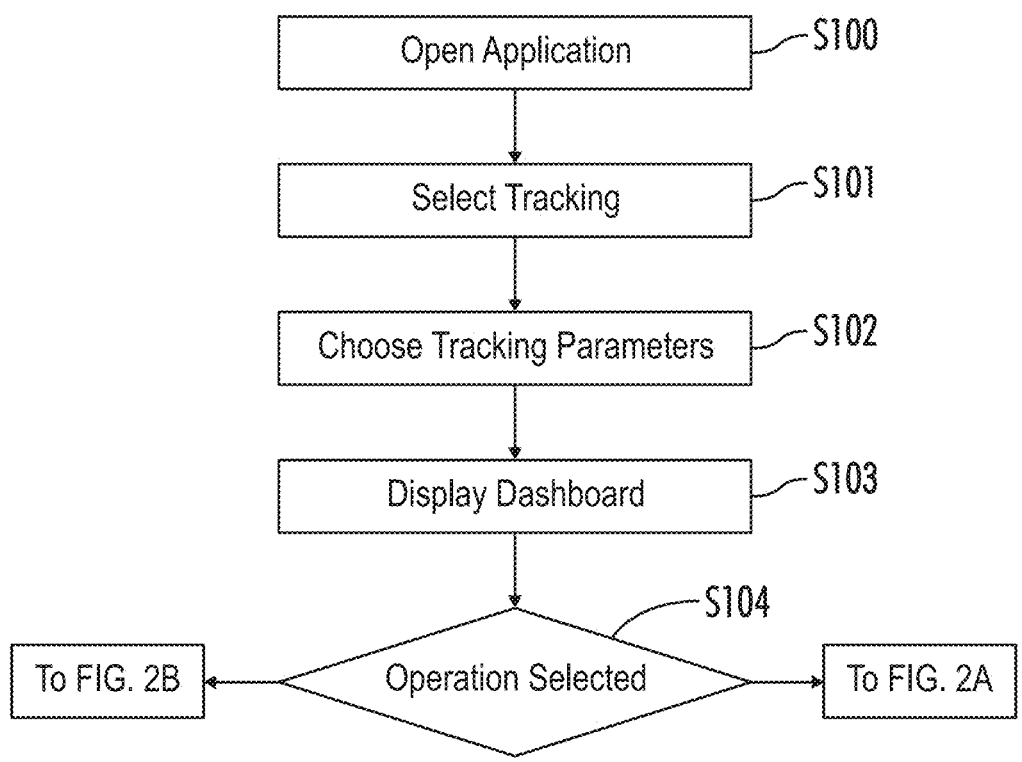
FIG. 1 is an exemplary embodiment of a patient compliance tracking method in accordance with the present disclosure.

Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment," as used herein does not necessarily refer to the same embodiment, although it may.

Depending on the embodiment, certain acts, events, or functions of any of the algorithms described herein can be performed in a different sequence, can be added, merged, or left out altogether (e.g., not all described acts or events are necessary for the practice of the algorithm). Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and algorithm steps described in connection with certain embodiments disclosed herein can be implemented as electronic hardware, computer software, or combinations of both. To clearly illustrate this interchangeability of hardware and software, various illustrative components, blocks, modules, and steps are described generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable medium known in the art. An exemplary computer-readable medium can be coupled to the processor such that the processor can read information from, and write information to, the memory/storage medium. In the alternative, the medium can be integral to the processor. The processor and the medium can reside in an ASIC. The ASIC can reside in a user terminal. In the alternative, the processor and the medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Medication Packaging consistent with the present disclosure may be designed to aid in the secure and accurate monitoring of prescription drug use, misuse, abuse, and diversion. One such packaging system may comprise blister packaging. The blister packaging may include tamper proof markings to ensure security, package identity authentication and to aid in image processing. Markings may be character-based or graphical (e.g., bar codes, QR codes, or the like) and include may identifiers such as, for example, (i) a package Globally Unique Identifier (package GUID), Universally Unique Identifier (UUID) or other unique identifier we subsequently and collectively refer to as such as a Unique Package identifier (UPID), (ii) a standards-based identifier for the dispensed product (e.g., RxNORM RXCui), a count associated with a dispensed product, (iii) an imprint code of the dispensed product, (iv) physical characteristics of the dispensed product (e.g., size, shape color), and (v) a public encryption key if label data is to be encrypted. Security labeling consistent with the present disclosure may be tamper proof, securely printed to prevent copying, and may be printed multiple times on the blister pack to enhance reading reliability. Labeling may also include graphical objects to support high reliability image registration such as lines of known length and colored objects. Markings may be used to demonstrate that the package is intact.

Blister packaging consistent with the present disclosure may be configured to provide clear contrast between filled and empty blisters to support image analysis. Contrast may be enhanced via the use of colored devices (e.g., inks or other physical entities) that may permanently change color or conformation upon opening e.g., via exposure to air or its constituents or in response to pressure changes. Tablets may be positioned with their respective imprint codes clearly visible through the blister film.

In various embodiments, the blister packaging may be configured to convey information about the package itself, about the prescription, about individual pills within the package, or the like. For example, in one exemplary embodiment, the front of a blister pack may be configured with one or more identifiers associated with overall prescription information. A back of the blister package may be configured to provide one or more additional identifiers overlying one or more pills within the blister pack to aid in counting remaining pills the in the package and establishing proper usage and sequencing (e.g., such as a daily pill drug content which may vary by day, or the like). In one embodiment, the one or more additional identifiers on the back of the blister package may be disrupted when a pill is removed such that would be obvious and/or make at least one of the additional identifiers become unreadable or unusable.

An exemplary embodiment of a blister package consistent with various aspects of the present disclosure is provided below with reference to FIGS. 24-25.

Each packaged product (e.g., a single blister pack) may be traceable via its unique package identifier, e.g., GUID or UUID (collectively referred to as a Unique Package identifier (LIPID)). One or more UPIDs may be linked to distributors upon shipment and/or to each prescription at the time of dispensing. In one exemplary embodiment, the dispensing pharmacist may scan a securely packaged product with a barcode reader or other imaging device before transferring prescription custody to the patient.

In various embodiments, a patient identity identifier such as a patient identity QR code may be scanned using a user device. The patient identity identifier may be associated with one or more prescriptions and at least one user. The patient identity identifier may be included as or included within an identifier associated with a packaged product. The patient identity identifier may be generated and/or provided to a user when a prescription is written, when a prescription is packaged, or any other time between prescription writing and prescription medication completion. For example, in one implementation, a patient identity identifier may be given to a user by a prescribing doctor at time of writing a prescription. In this example, the patient identity identifier may function as a patient-specific and prescription specific "ticket" and may optionally be required to be scanned in association with one or more sets of captured data.

Additionally or alternatively, a patient identity identifier may be printed on a surface of a packaged product for scanning by the user. Further, the patient identity identifier may include at least one of metadata configured to be added to, edited within, or removed from metadata of captured data from a user device (e.g., a user device hardware identifier inserted into a captured image as metadata or the like). Although described with reference to metadata, the patient identity identifier may additionally or alternatively take the form of user- or computer-perceptible information included within or otherwise associated with captured or stored data.

In one embodiment, home monitoring may be accomplished via imaging dispensed medications and transmitting those images for processing, analysis, and reporting. A patient or their proxy may image dispensed medications and packaging using a digital camera or other image-capturing means, such as a camera built into a smart phone. A smart phone application may assist the process at several steps including:

1. Image Acquisition—the application may permit taking a timely, high quality picture via several methods. The application may process the image on-screen before the picture is taken to:
   i. Determine the packaging edges and to assess size and angle of the as-is image.
   ii. The application may assess image brightness and ambient lighting adequacy
   iii. Read at least one barcode, QR code, or other identifier prior to sending the image to assess focus.
   iv. Analyze other image defects e.g., light reflections
   v. Correct defects via automated software control when possible
   vi. Provide corrective user feedback (visual and auditory) ("move the camera back") when automated correction is not possible.
   vii. Provide confirmatory user feedback (visual and auditory) when image quality is satisfactory, such as a green frame or soothing tone.
   viii. Support an "auto snap" mode that may capture an image automatically when quality is determined to be satisfactory. This permits imaging to include one-hand operation.
   ix. The application may remind a user that imaging is due ("alarm clock" mode), either directly or via electronic communication to the patient or their proxy. The application may also provide a calendar of upcoming required imaging events
2. Image analysis—pre-transmission lightweight image analysis may be performed by the application to determine number of pills taken and remaining, and if any problems are detected (e.g., semi-destroyed packaging). Basic results and advice may be given to the user (e.g., "6 pills remaining" or "Image may be unusable, please try again")
3. Image Transmission—the application may manage secure transfer of images for analysis and confirmation of receipt. Messages may be encrypted and certificates may confirm the identity of at least one of the sender, sending and/or receiving devices, and may ensure that transmitted images and metadata have not been changed or fabricated.
4. Results Feedback—the application may share the results of image analysis and metrics with the sender. User feedback may range from (i) a simple confirmation of transmission and processing success, (ii) results of image analysis for a single image, and (iii) results of image analysis across images and time.

Various features for of the smart phone application may be replicated in a web application running on other computer platforms, such as a PC. In that case, options to use an existing picture may have to be employed if a specific computer does not have a suitable imaging device connected thereto.

Images transmitted in accordance with the present disclosure may be processed to assess image quality, to decode metadata, and/or to detect medication presence and absence from a package. In one exemplary embodiment, various aspects of image processing may be accomplished using high quality optimized computer vision libraries, such as Intel's Open source Computer Vision (OpenCV).

1. Image Quality—may include size, shape, brightness, reflection as initial measures. Secondary measures may be based on additional processing.
2. Image Metadata—data encoded on the package may be read and converted into required usable formats (e.g., barcode-to-text package UPID).
   i. Barcode read errors and their corrections may be tracked.
   ii. Registration mark identification, e.g., for size and color correction.
   iii. OCR may be used in combination with post OCR error correction based on lexical and semantic approaches.
3. Image Preprocessing
   i. Image quality may be improved algorithmically, when necessary.
   ii. Optimal Preprocessing using sequential application of techniques such as noise, smoothing, thresholding, geometric transformation and edge detection may be empirically determined and applied
4. Image-based Medication Presence and Absence analysis.
   i. Deterministic morphologic image analysis (e.g., "how many contiguous pixel collections with color range between x and y, long axis and short axis within 2% of each other, and area within 5% of (pi*long axis) (e.g., a circle) are found in the image?")
   ii. Machine Classification Image analysis—machine learning and classification may be used to determine medication presence or absence. The unit of inquiry may be the whole package or subsections (e.g., a single blister, a front section, a rear section, etc., for example as described below with at Paragraph [00265]).
   iii. Integration of multi-modality results. Methods to integrate findings of different image analysis techniques may be used to assess reliability (e.g., agreement) and to improve results when possible.
5. Quality and Reliability data from each step may be used to
   i. Accept the result
   ii. Guide additional processing
   iii. Request that the image be re-sent from the consumer
   iv. Place the image in queue for human review and possibly intervention For example, image processing consistent with the present disclosure may provide image analysis on one or more pill pictures. Metrics to be calculated may include, but are not limited to:

1. Single Image Processing
   i. Number of pills removed from the blister pack
   ii. Number of pills remaining in the blister back
   iii. Percentage use
   iv. Image quality
2. Single Image+Prescription Data (may require Personally Identifiable Information (PID)
   i. Rate of consumption
   ii. Percentage of time elapsed and remaining for the intended duration of the prescription
   iii. Ratio of the percent used to the percent of covered time
   iv. High and low allowed usage statistics for PRN dosing and comparison to actual usage.
3. Results over Time
   i. Trends in all metrics across the life of a prescription
   ii. Trends in all metrics across prescriptions for the same medication (may require PID
   iii. Trends in all metrics across all monitored prescriptions. (may require PID
4. Results integrated with pharmacologic or clinical knowledge that potentially impacts urgency or extent of mis-compliance System Integration Provision of metrics derived from packaged product imaging to clinicians is important to "close the loop" in computer-aided prescription drug compliance monitoring. Metrics can be provided via progressively sophisticated methods including Snapshot and time series package-specific statistics
   a. Free of personally identifiable information (PII); and
   b. Augmented by prescription-specific information, i.e., containing PII Non-PII based metrics and graphics, indexed by package UPID, may be provided by a Service Board via a website (for viewing) or web service data provision for integration with the prescriber's electronic health record (EHR) system.

Consumption and compliance statistics may be provided to the prescriber in at least two modes—(i) on request of the provider or provider EHR system (pull), and (ii) when a potentially serious misuse is detected (push). In an advanced version, the application may notify a provider, patient, other members of the healthcare or homecare team or registered recipient with various alerts that may escalate depending upon the nature of the alert. For example, detecting that all pills have gone missing in a short interval could indicate diversion or overdose. In one embodiment, the consumption and compliance statistics may be implemented as a subscription-based service.

Integration with Pharmacy System

Integration of new dispensing information (e.g., package UPID) with Pharmacy systems may be provided to successfully implement computer-based prescription drug monitoring. In one such scenario, data acquired at the time of dispensing may be package-specific only. No personally identifiable information (PII) can be included until linkage to a pharmacy system is established.

Prescription dispensing may be supported via a software system that may minimally read a QR or barcoded package UPID on an actual package being dispensed at the time of dispensing and custody transfer. Advanced configurations may provide extra information such as an image of the actually dispensed packaged product and other package-specific metadata.

Package UPIDs, images and metadata may be shared in one embodiment as a secure service (e.g., via a software component accessible to computers connected over a network) configured to integrate with existing pharmacy systems. Accepted standards such as the National Council of Prescription Drug Programs (NCPDP) Script version 10.6 may be used, where possible. A technical evaluation of primary storage methodologies (e.g., a centralized database) may be conducted to optimize performance and ease integration. In various embodiments, one or more primary storage methodologies may include at least one of centralized, federated, and/or stand-alone databases or data sets, for example depending upon one or more needs or requirements.

If a PII in custody of Service Provider option is elected, numerous opportunities and paths exist. An initial implementation of a Prescription Monitoring Health Record may be built with data elements contained in NCPDP Script, problem list, care providers and other essential .EHR components at its core.

Although described with reference to a pharmacy system, it should be appreciated that implementations consistent with the present disclosure may extend to electronic health records (EHRs). For example, electronic records may be integrated in various embodiments to get clinical data based on standards required for .EHR certification and meaningful use and standards required for data exchange via other accepted standards such as Nationwide Health Information Network (NwHIN)—a set of standards, services, and policies that enable the secure exchange of health information over the Internet. Medication orders, outbound e-prescribing messages and other key from .EHR may be incorporated. Data may be sent back to .EHR via CCDA, HL7 Fast Health Integration Resources (FHIR), etc.

Medication Monitoring Prescription Scheduling

Who—The monitoring prescriber or designated proxy. Permitted roles may include the prescription writer, nursing staff, pharmacy staff or administrative members of a care team, depending on practice scope and organizational policy.

What—Monitoring events may be scheduled and managed as "calendar appointments" using established standards, calendar software and notification software (with necessary extensions).

Ways to Schedule:

1. Explicit Enumeration: User may select dates for monitoring in a manner similar to making an appointment. One exemplary user interface may include a calendar application where dates and times may be directly entered in a Graphical User Interface (GUI).
2. Repeating Events—a user may select dates and/or times for monitoring as repeating events, such as sequential Tuesday afternoons for 4 repetitions.
3. Machine Selected Events—a user may pick the number of events to occur in a particular time period. For example, eight events in four weeks, and the precise date/time of events may be determined by the system. While machine-selected events may not be totally random, they may be random within particular temporal windows (e.g., daytime, work days, etc.).
4. Some combination of 1-3.
5. Named Monitoring Profiles—potentially complex named profiles, such as "tight control" may be created to easily allow rapid selection of desired schedules.

Components
1. Monitoring Period Start—may be defined as Date/Time explicitly or as a time duration from an arbitrary event, such as "Two days after prescription is filled."
2. Monitoring Period Duration—time during which monitoring may be conducted
3. Required Response Date/Time—date and time for the monitoring to occur
4. Required Response Interval—interval in which the monitoring must be conducted, in one embodiment starting from the required response time (e.g., three hours allowed to upload image in order to be considered compliant).
5. Frequency—how many monitoring events occur in the monitoring period, if events are to be scheduled by computer (e.g., machine-selected events as described above)
6. Event Status
   i. Announced—announced events may be known to the monitoring prescriber and to the monitored patient.
   ii. Unannounced—unannounced events are not known in advance by the monitored patient and may or may not be known to the monitoring prescriber. The Compliance Service may change a status of one or more unannounced monitoring event appointments to announced appointments when appropriate based on a timer and/or required response window (e.g., three-hours' notice)

Workflow of Event Scheduling
1. Scheduler opens application and logs in.
2. Role-based access control determines functions available to User.
3. Find Patient to be monitored.
   i. Look up by ID or other characteristic in monitoring system.
   ii. Selectively read QR code ID (or other identifier) off patients phone.
   iii. Matching algorithm based on characteristics of patient
4. Confirm prescription.
5. Open Scheduling component with calendar and menus offering scheduling options as noted in an exemplary "ways to schedule" section.
6. Select monitoring schedule for the chosen patient, prescription and/or time period.
7. Publish monitoring schedule to Compliance Service electronically, for example, via iCalendar or similar standard such as xCal or jCal with extensions as necessary to accommodate system requirements.
8. Receive confirmation of monitoring schedule from Compliance service.
9. Log out.

Monitoring Event Messaging
In one exemplary embodiment, one or more calendar appointment standards may be implemented and integrated with one or more notification systems, such as those on IOS and Android platforms.

Medication Monitoring Patient Response
Who—Patient or Caregiver Workflow of Monitoring Response
1. Patient may receive notification of monitoring event on their smartphone and/or in their calendar.
   i. To receive notices patient may subscribe to their provider-determined monitoring calendar designated by a Monitoring Service.
   ii. Notification and appointment may contain links to open a smartphone monitoring application 2. Patient launches monitoring application, for example on their smartphone with a single touch or click of the notification of calendar appointment
3. Application may launch directly into an Imaging Mode, ready to take a picture of the patient's medications (e.g., a blister pack)
4. Patient points phone at the blister pack. If imaging is set to "auto" mode a picture may be automatically snapped when quality parameters are met. If Imaging is set to "manual" mode, the patient may press a button to snap a picture of one or more medications.
5. Software on the smartphone may ensure that image quality is sufficient. If not the user may be alerted to re-take the picture. Parameters of quality may include elements common to all pictures (e.g., focus, brightness, etc.) and elements specific to the monitoring application, such as the ability to read bar-coded UPID, and basics of package geometry.
6. Software on the smartphone may securely transmit the image and necessary metadata to the Compliance Service for processing.
7. Software on the smartphone may receive a receipt corresponding to a successful transmission.
8. Software on smartphone may display a confirmation of receipt to a patient; it may optionally display a message regarding compliance status (e.g., "Good Job!"; "You've missed some pills," or the like).

Compliance Performance Tracking—Patient Perspective
1. Patient starts smartphone application
2. Patient selects "My Compliance" capability
3. Dashboard View presented based on selected view—
   i. View Parameters—
      1. Time Frame: e.g., day, week, month, all
      2. Rx Characteristics
         a. Prescription
         b. Medication across prescriptions
         c. Rx Class (e.g., AHFS)
   ii. Initial view based on "on board" data previously downloaded from Compliance Service (push vs pull).
   iii. Software contacts Compliance Service for Updates.
   iv. Updated View presented including any new data.
4. Drill Down View
   i. Accessed from Dashboard View.
   ii. User Selects a particular dashboard view and requests details.
   iii. Smartphone Software sends request for monitoring image thumbnails dates and pill counts; waits for response from Compliance Service
   iv. Smartphone software displays returned data and images Compliance Performance Monitoring—Prescriber Perspective
1. Patient Specific Pull Mode
   i. Used to assess past compliance on demand such as at the time of prescription re-issuance for opioids; if a clinically relevant event has been detected (push mode); caregiver inquiry etc.
   ii. User logs in and finds patient
   iii. User selects "Compliance Monitoring Results" functionality iv. Dashboard View presented based on selected view—
  1. View Parameters—
    a. Time Frame: day, week, month, all
    b. Rx Characteristics
      i. Prescription
      ii. Medication across prescriptions
      iii. Rx Class (e.g., AHFS)
  2. Summary data regarding compliance with prescription (e.g., medication possession ratios) and compliance with monitoring requirements (e.g., percent on time, percent late, percent deferred)
  3. This information may be part of a special purpose portal, integrated into the prescribers' electronic health record system (in one embodiment via standards such as HL7 CCDA) or accessed via some other methodology.
2. Patient-Specific Push Notification
i. Notification of potentially significant compliance events may be pushed to the healthcare provider, patient, and/or patient caregiver.
ii. Examples
  1. Dangerous overutilization—patient may have taken too many pills in a given time period that could cause harmful effects (e.g., "overdose") or have diverted pills.
  2. Dangerous underutilization—patient may have missed essential medication doses that could have adverse outcomes (e.g., heart failure medication noncompliance that could result in worsening symptoms, emergency room visits, or hospitalizations)
  3. This information may be pushed to a special notification application, integrated into the notification system of the prescribers' electronic health record system or via some other methodologies.
iii. Management
  1. Various actors (patient, provider, nurse, family member) can subscribe or unsubscribe to notifications for a patient or a group of patients (e.g., all notifications for a practice group). Message subscriptions may be tailored based on urgency, role of the recipient, preferred language and communications modality.

Standards and Resources

Particular exemplary standards and resources consistent with various aspects of the present disclosure may include—

NCPDP SCRIPT Standard Implementation Guide: Used to standardize transmission of prescription information including new prescriptions, changes, refill requests, fill status notifications, cancellations and medication history.

NCPDP Structured and Codified Sig Format Implementation Guide: Used to standardize electronic prescription directions based on existing standards such as NCPDP SCRIPT, Health Level 7 (HL7) and ASTM Continuity of Care Records (CCR).

NCPDP Specialized Standard Implementation Guide: Used to standardize transmission of medication therapy management transactions including clinical information exchanges.

NCPDP Post Adjudication Standard Implementation Guide: Used to standardize transmissions of detailed post-adjudication drug or utilization claim information.

NCPDP Prescription File Transfer Standard Implementation Guide: Used to electronically transfer prescriptions between pharmacies.

Calendar Standards
Internet Engineering Task Force (IETF) iCalendar (RFC 5545, "Internet
Calendaring and Scheduling Core Object Specification "September 2009)
RFC 7529 Non-Gregorian Recurrence Rules in the Internet Calendaring and
Scheduling Core Object Specification (iCalendar)
RFC 6321 xCal: The XML Format for iCalendar
RFC 7265 jCal: The JSON Format for iCalendar
Additional Standards that may be deployed
HL7 Consolidated Clinical Document Architecture (C-CDA)
Standards specified in the 2015 Edition health IT certification criteria from Office of National Coordinator for Health Information Technology.
HL7 Version 3 Standard, Value Sets for Administrative Gender
PHVS_RaceCategory_CDC for self-reported race
ISO 639.2 for preferred language
Numerous semantic types from National Library of Medicine RxNorm
National Drug Codes (NDC)

Referring generally to FIGS. 1-27, various exemplary apparatuses and associated methods according to the present disclosure are now described in detail. Where the various figures may describe embodiments sharing various common elements and features with other embodiments, similar elements and features are given the same reference numerals and redundant description thereof may be omitted below.

Various embodiments of an apparatus according to the present invention may provide an automated medication compliance assurance system. Although described as being used in the context of prescription drugs, implementations consistent with the present disclosure may additionally or alternatively comprise any system which tracks or monitors usage or exposure to a regulated or otherwise controlled area or item.

As shown in FIG. 1, in one exemplary embodiment, a patient compliance tracking method may be provided. The method may begin at step S100, where a patient may open an application. In one embodiment, the patient may execute the application on an electronic device (e.g., client electronic device 10). The electronic device may comprise, for example, a desktop computer, a laptop computer, a tablet computer, a smartphone, or any other device capable of executing programmed instructions, within the scope of the present disclosure. The application may be stored in a memory of the electronic device in one embodiment, or may have one or more portions stored remotely from the electronic device. In one exemplary embodiment, the application may be implemented as a partially or wholly distributed program, for example in a cloud computing environment or any other distributed manner. The electronic device may be connected to a network, through which the electronic device may be capable of sending and/or receiving data for use consistent with the present disclosure.

At step S101 the user may select a tracking option within the application. By selecting the tracking option, the application may permit an application user to choose tracking parameters at step S102. After selecting tracking options, a dashboard may be displayed to the application user at step S103. The dashboard may enable the application user to select one or more options at step S104. For example, the application user in one exemplary embodiment may select from summary data and detail data.

Figure 2A:
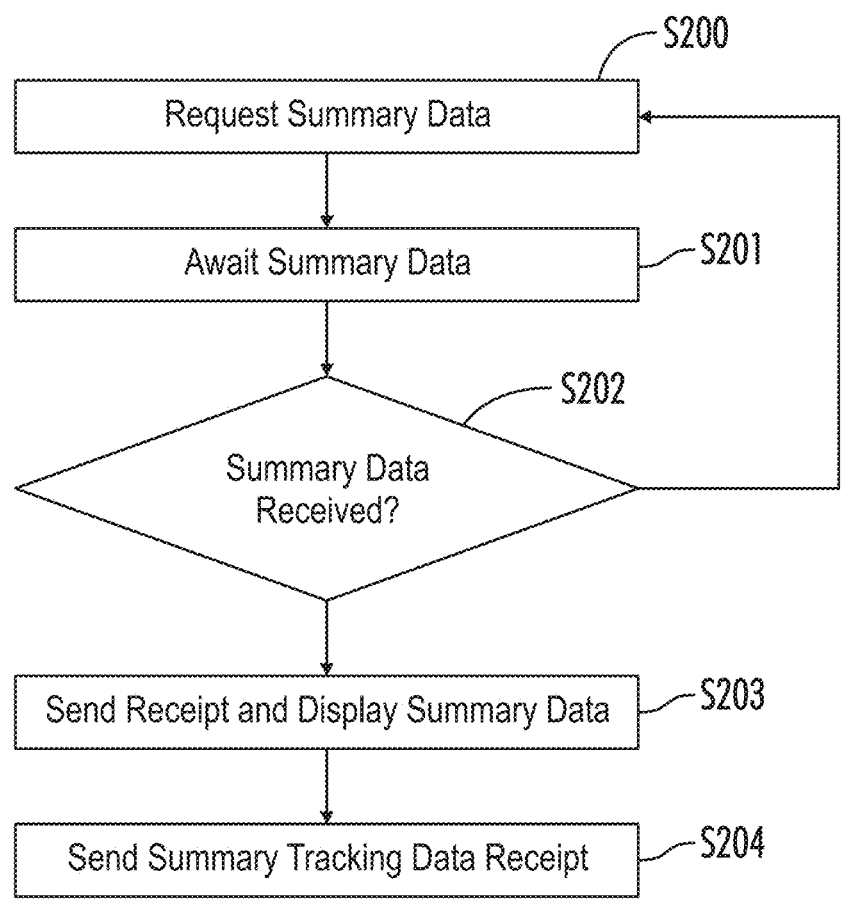
FIGS. 2A-B are exemplary embodiments of processes for requesting and receiving summary data and detail data, respectively, in accordance with the present disclosure.

If summary data is selected at step S104, the process may continue to step S200, illustrated by FIG. 2A, where summary data may be requested. The summary data request may, in one embodiment, be transmitted over a network, may be a local storage request, or may be a combination thereof. After requesting the summary data, the application user (e.g., a patient) may await receipt of the summary data at step S201. At step S202 the application may determine whether summary data has been received. If summary data has not been received, the process may return to step S200, or the application state may return to a previous screen or processing stage. If summary data is received at step S202, the process may proceed to step S203, where a send receipt may be transmitted and summary data may be displayed to the application user. In one embodiment, the application may transmit a summary tracking data receipt at step S204, for example to a compliance service (e.g., executing on one or more compliance servers 20 in an exemplary embodiment).

Figure 2B:
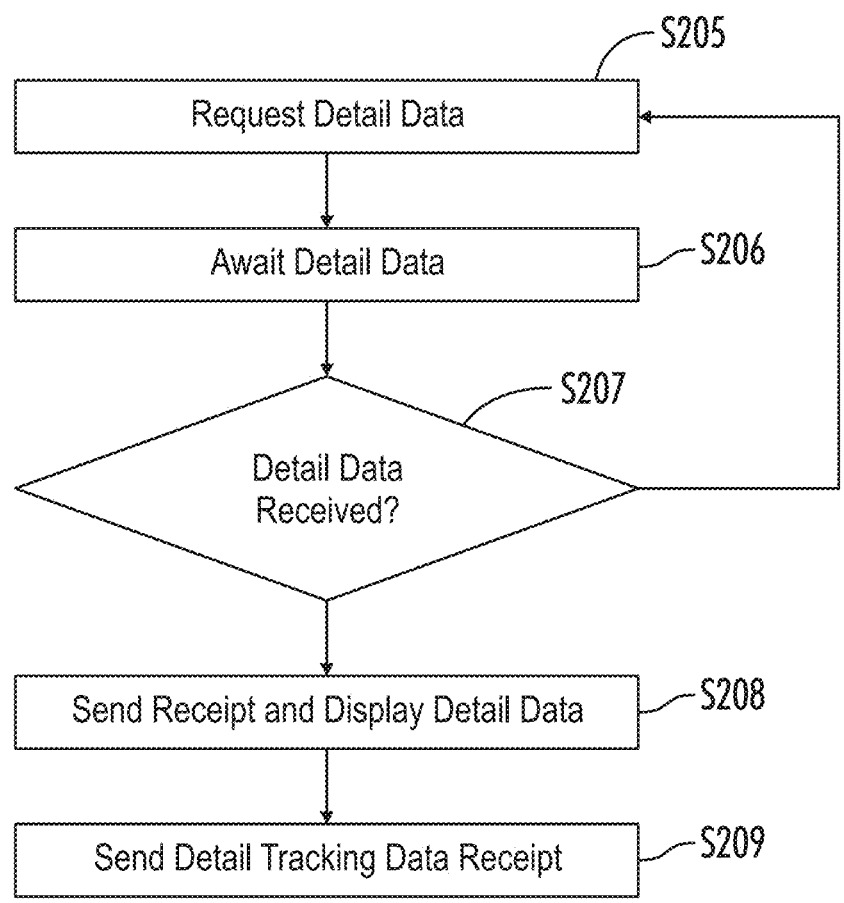

If detail data is selected at step S104, the process may continue to step S205, illustrated by FIG. 2B, where detail data may be requested. The detail data request may, in one embodiment, be transmitted over a network, may be a local storage request, or may be a combination thereof. After requesting the summary data, the application user (e.g., a patient) may await receipt of the detail data at step S206. At step S207 the application may determine whether detail data has been received. If detail data has not been received, the process may return to step S205, or the application state may return to a previous screen or processing stage. If detail data is received at step S207, the process may proceed to step S208, where a send receipt may be transmitted and detail data may be displayed to the application user. In one embodiment, the application may transmit a detail tracking data receipt at step S209, for example to a compliance service.

Figure 3:
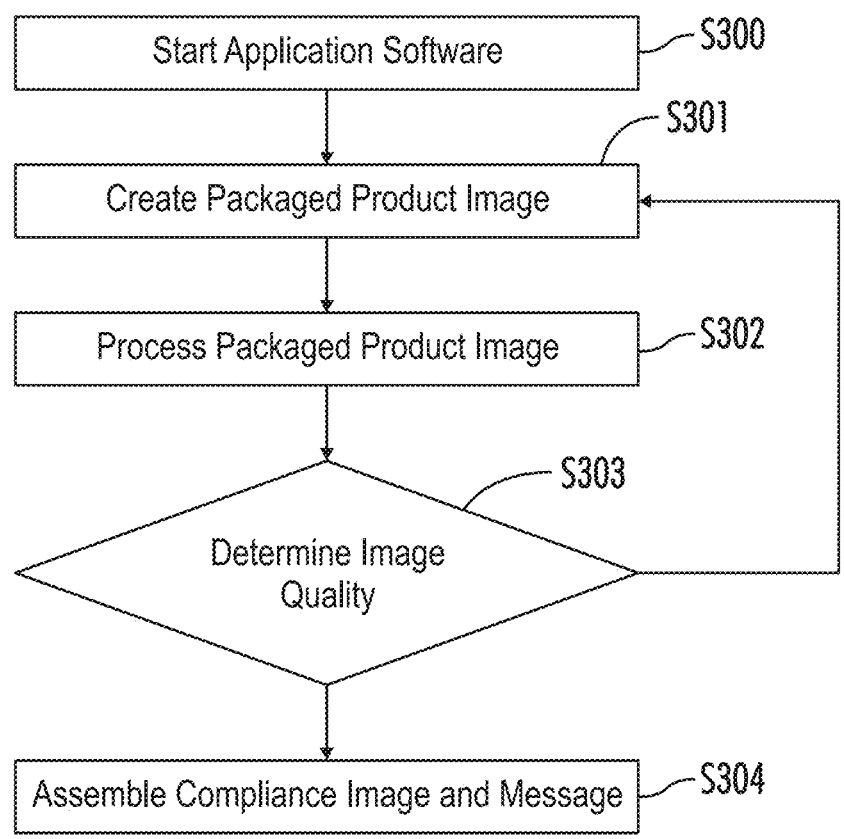
FIG. 3 illustrates an exemplary patient-based monitoring method in accordance with the present disclosure.
Figure 4:
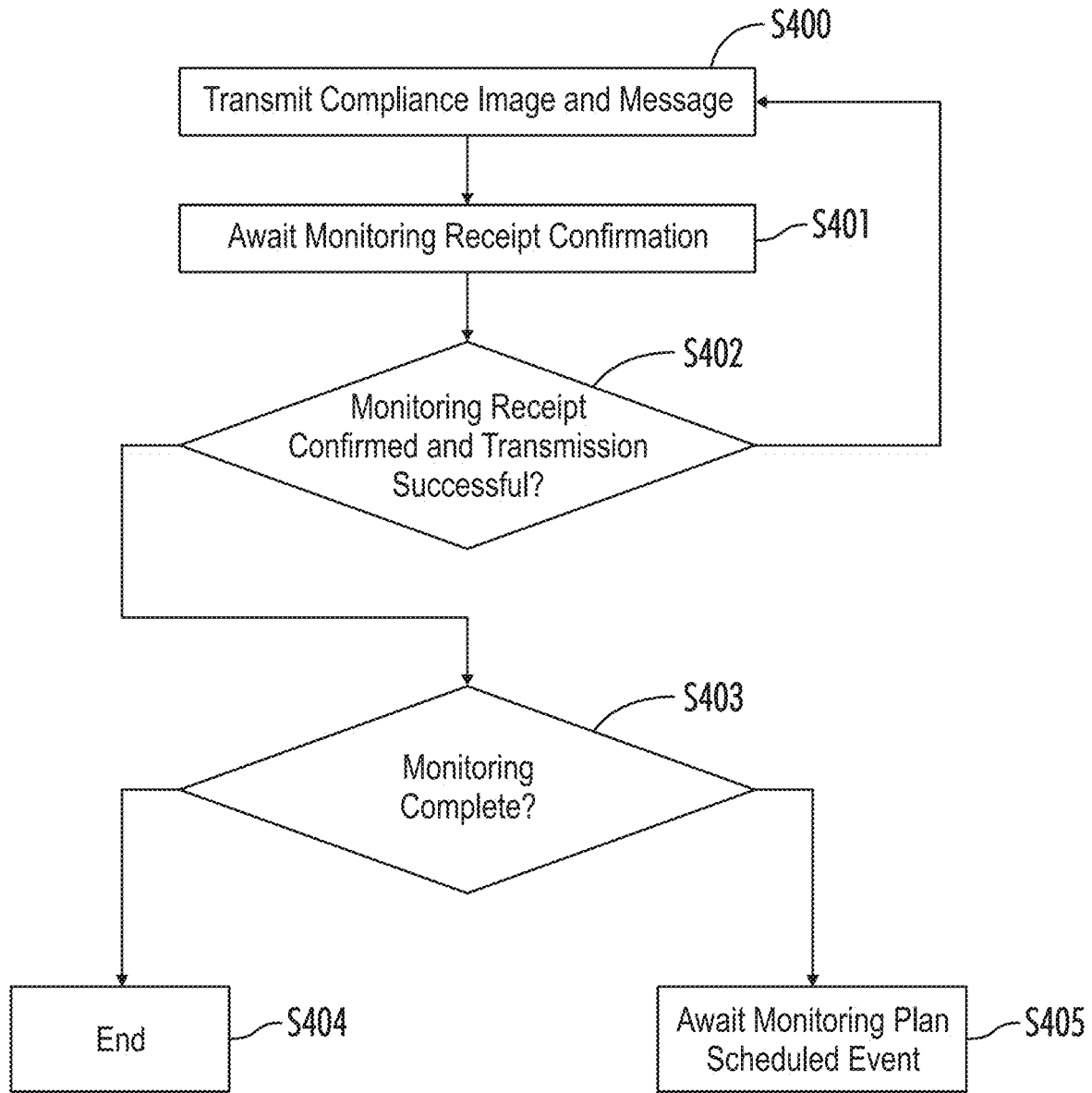
FIG. 4 illustrates an exemplary embodiment of a compliance monitoring process performed at a patient electronic device, in accordance with the present disclosure.

FIG. 3 illustrates an exemplary patient-based conformance monitoring method. The illustrated method may begin at step S300, where an application user (e.g., patient) may execute application software on an electronic device. The application user may create a packaged product image at step S301. The packaged product may, in one exemplary embodiment, comprise a package containing one or more prescription drugs. In one exemplary embodiment, the application user may obtain an image corresponding to the packaged product by means of the electronic device. The electronic device may obtain the image of the packaged product, for example, by means of a camera associated with the electronic device, or by any other means of obtaining an image of the packaged product, for example, from an external device.

Although described as pertaining to prescription drugs, it should be appreciated that the present disclosure may be implemented in numerous other fields. Specifically, aspects of the present disclosure may be implemented in any system where access to or conformance verification of any regimen may be monitored and/or verified, without departing from the spirit and the scope of the present disclosure.

After obtaining an image of the packaged product, the image of the packaged product may be processed at step S302 (e.g., by the application running on the electronic device). An image quality of the image of the packaged product may be determined at step S303. The image quality may be variously analyzed either before processing at step S302 or after processing. If an image quality associated with the packed product image is poor or below a threshold, the process may return to step S301, where an application user may obtain an image of the packaged product. If the image quality of the packaged product is determined to be acceptable at step S303, the process may continue to step S304, where a compliance image and message may be assembled.

After a compliance image and message are assembled, the process may continue at step S400, where the compliance image and message are transmitted (e.g., to a compliance service). The application may then wait to receive a monitoring receipt confirmation at step S401. At step S402, it may be determined whether the monitoring receipt was confirmed and that the transmission was successful. If the result of the determination at step S402 is negative, the process may return to step S400. If the result of the determination at step S402 is positive, the process may continue to step S403, where it may be determined whether monitoring is complete. If monitoring is complete, the process may end at step S404. If the monitoring is not complete, the process may continue to step S405, where the application may await a monitoring plan scheduled event.

Figure 5:
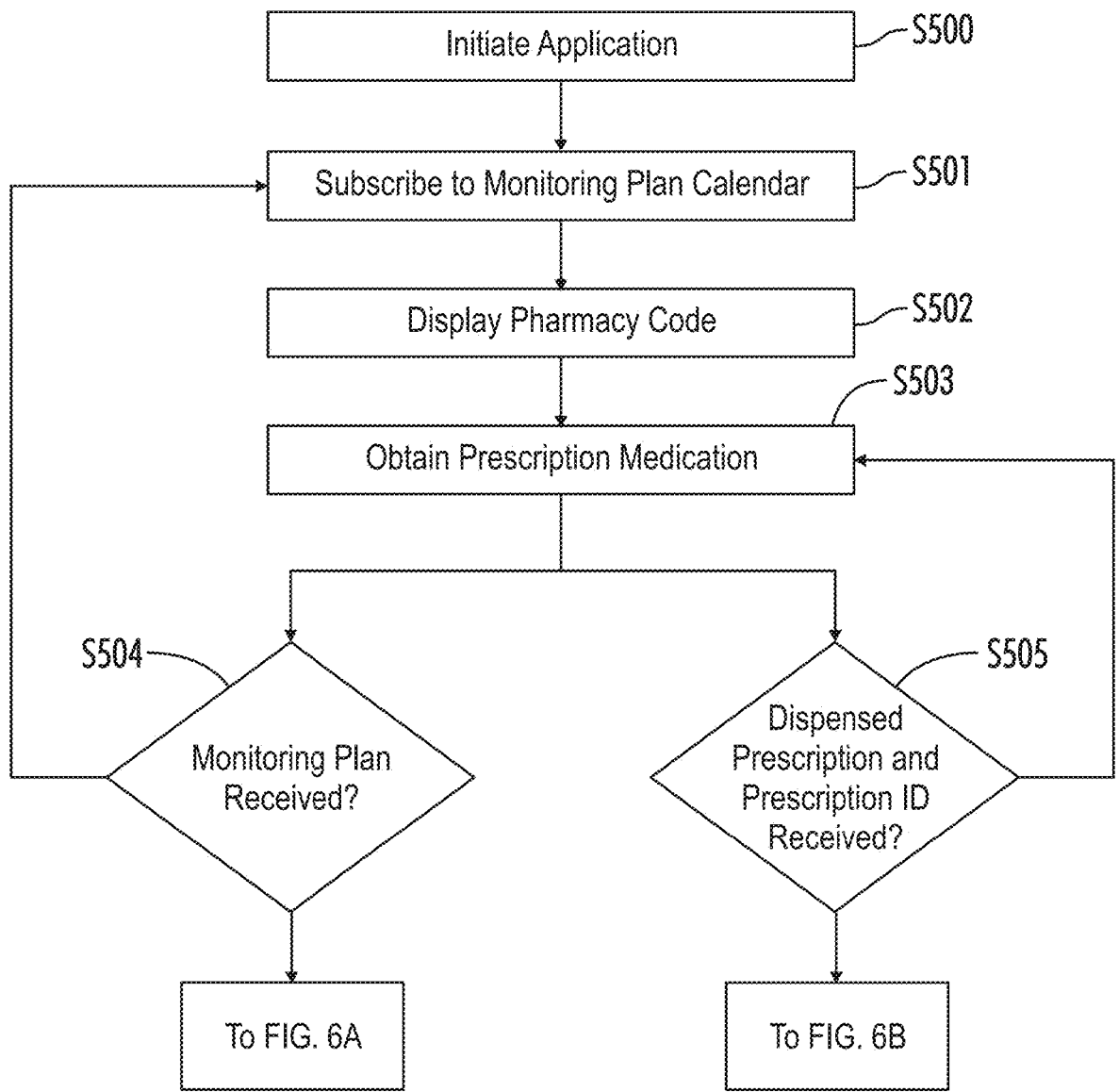
FIG. 5 illustrates an exemplary embodiment of a process of a patient obtaining medication in accordance with the present disclosure.

FIG. 5 illustrates an exemplary embodiment of a process of a patient obtaining medication according to an exemplary embodiment of the present disclosure. The process may begin at step S500, where an application user (e.g., patient) may initiate an application at an electronic device. In one exemplary embodiment, the application user may subscribe to a monitoring plan calendar. However, application users are not required to subscribe to a monitoring plan calendar in various embodiments of the present disclosure. A pharmacy code may be displayed by the application at step S502. The pharmacy code may be used by the patient to provide at least one of proof of identity and/or proof of valid prescription to a pharmacy employee so that the patient may obtain his or her valid prescription. The pharmacy code may comprise, for example, a QR code, a barcode, or any other visual means of indicating or conveying information associated with a prescription, patient, provider of goods, or good(s).

A patient may obtain a prescription medication at step S503. After the patient has picked up their prescription, it may be determined at step S504 whether a monitoring plan has been received. If a monitoring plan has not been received, the process may wait for a monitoring plan to be received and/or may return to step S501. If a monitoring plan is received, the process may continue at FIG. 6A. It may also be determined at step S505 whether a dispensed prescription and prescription identifier JD) have been received. If it is determined that one or more of a dispensed prescription and prescription ID have not been received, the process may await receipt of the one or more of the dispensed prescription and prescription ID and/or the process may return to step S503. If it is determined that the dispensed prescription and prescription ID are received at step S505, the process may continue at FIG. 6B.

Figure 6A:
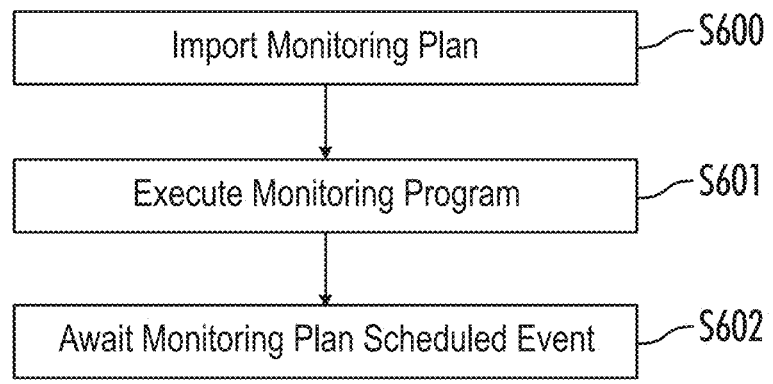
FIGS. 6A-B respectively illustrate an exemplary process for executing when it is determined that a monitoring plan was received, and an exemplary process for executing when it is determined that a dispensed prescription and prescription ID have been received, in accordance with the present disclosure.

FIG. 6A illustrates an exemplary process for execution when it is determined at step S504 that a monitoring plan has been received. The process may begin at step S600, where the monitoring plan may be imported. The imported monitoring program may be executed at step S601. After executing the monitoring program, the application may away a monitoring plan scheduled event, for example a future monitoring scheduled event provided in the monitoring plan at step S605.

Figure 6B:
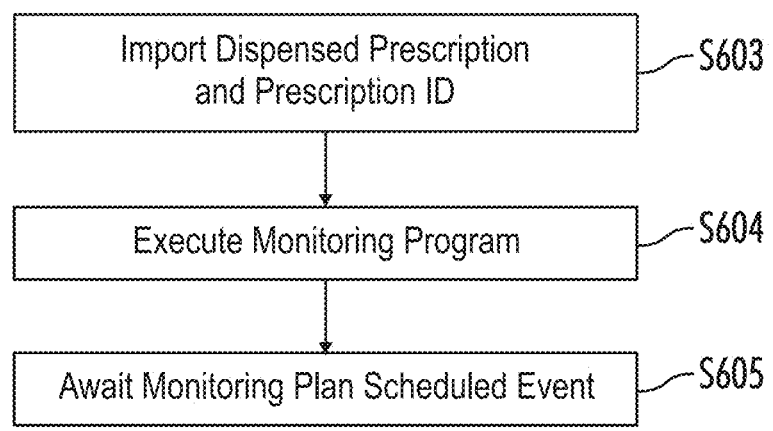

FIG. 6B illustrates an exemplary process for execution when it is determined at step S505 that the dispensed prescription and prescription ID have been received. The process may begin at step S603, where the dispensed prescription and prescription ID may be imported. The monitoring program may be executed at step S604. After executing the monitoring program, the application may away a monitoring plan scheduled event, for example a future monitoring scheduled event provided in the monitoring plan at step S605.

Figure 7:
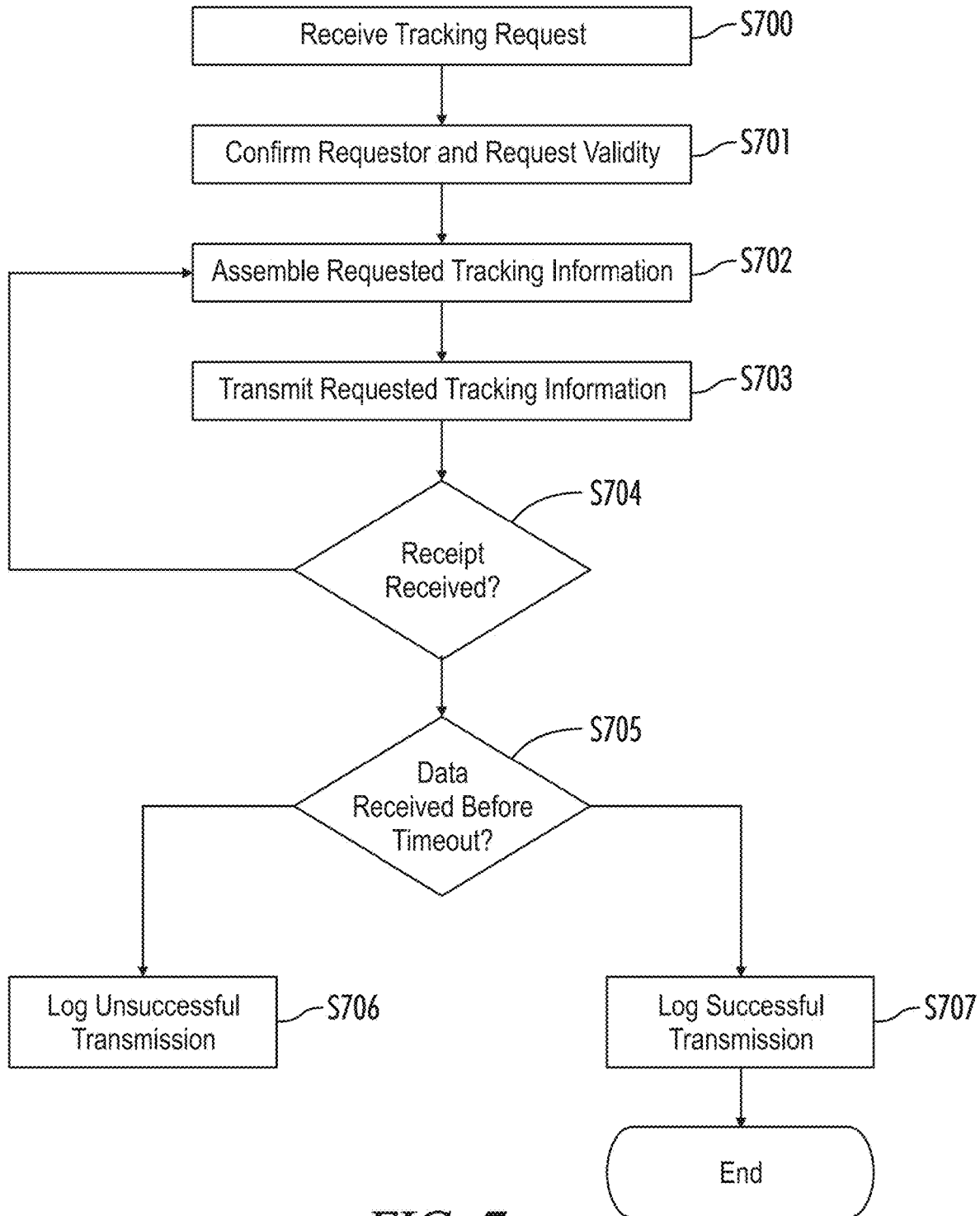
FIG. 7 illustrates an exemplary tracking process for a compliance service in accordance with the present disclosure.

FIG. 7 illustrates an exemplary tracking process for a compliance service consistent with various aspects of the present disclosure. The compliance service may, in one exemplary embodiment, comprise a computing service, for example executing on an electronic device. In one embodiment, the compliance service may execute upon a network-connected electronic device located remotely from the electronic device of the application user. The compliance service may also be executed on the application user's electronic device, without departing from the spirit and the scope of the present disclosure.

The process illustrated by FIG. 7 may begin at step S700, where a tracking request may be received at the compliance service. In one embodiment, the tracking request may be received from an application user. The tracking request may comprise, for example, at least one of a summary data request and/or a detail data request (e.g., as described above with reference to steps S200 and S205). In response to receiving a tracking request, the compliance service may confirm a requestor's identity and/or a validity of the received request at step S701. After confirming the request and request validity, the compliance service may assemble requested tracking information at step S702. The assembled requested tracking information may be transmitted by the compliance service at step S703. In one exemplary embodiment, the assembled requested tracking information may be transmitted to an application associated with an application user (e.g., patient). In one exemplary embodiment, the assembled requested tracking information may be transmitted to and received at the patient's electronic device, for example, as described above with reference to steps S202 and S207.

At step S704 it may be determined whether a receipt has been received corresponding to the transmitted assembled requested tracking information. In one exemplary embodiment, the compliance service may determine whether a receipt has been received from an application associated with a patient, for example, as described above with reference to steps S204 and S209. If the determination at step S704 is negative, the compliance service may await receipt and/or may return to step S703. If the determination at step S704 is positive, the process may proceed to step S705, where it may be determined whether data was received before a timeout occurred. The timeout value may comprise any spatial and/or temporal value or setting capable of conveying a value associated with the received data. If the result of step S705 is negative, the compliance service may log an unsuccessful transmission at step S706 and/or return to step S703. If the determination at step S705 is positive, the compliance service may log a successful transmission at step S707 and this process may end.

Figure 8:
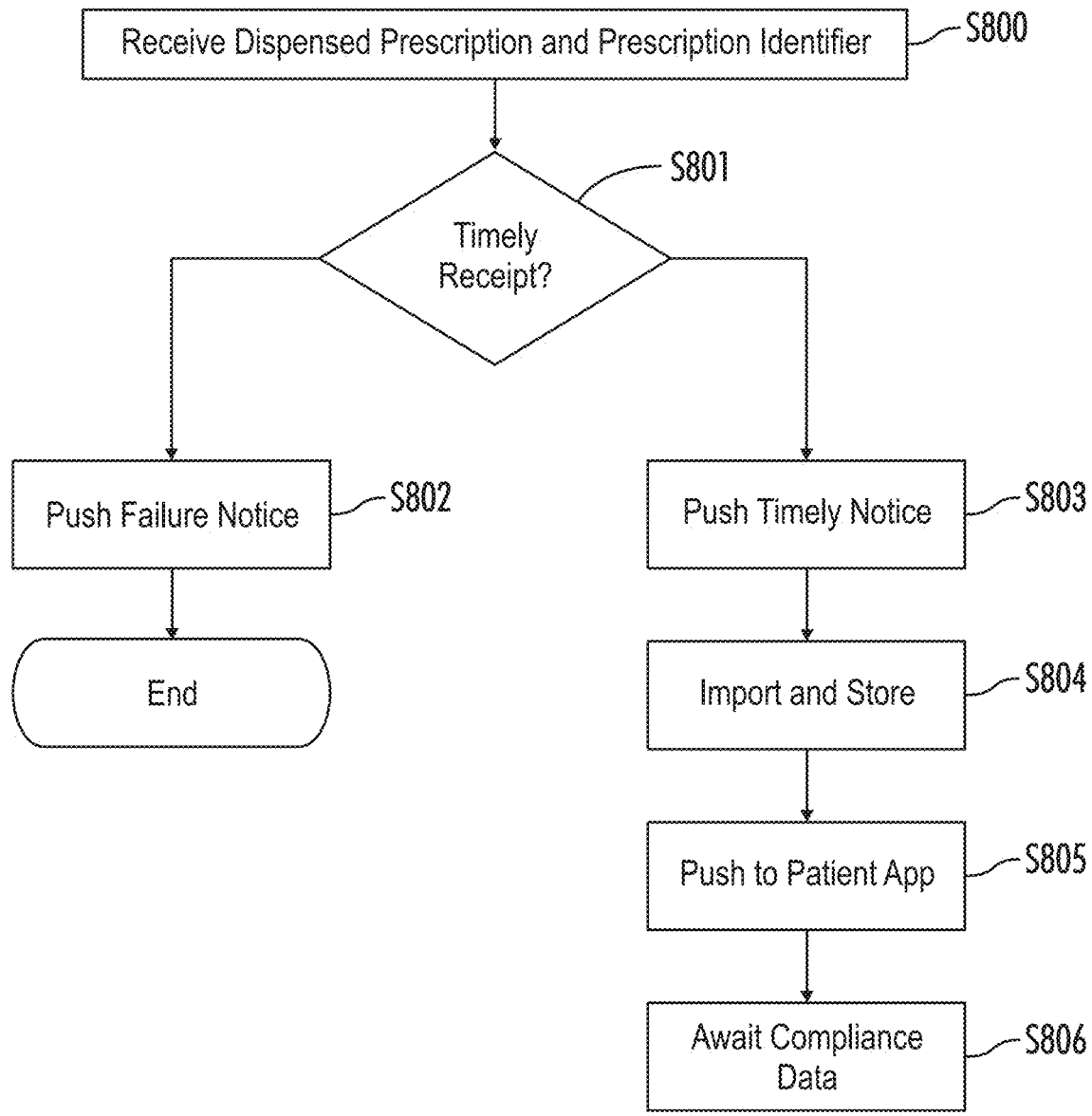
FIG. 8 illustrates an exemplary process occurring after dispensed prescription information and a dispensed prescription ID are received by the compliance service, in accordance with the present disclosure.

FIG. 8 illustrates an exemplary process occurring after dispensed prescription information and a dispensed prescription ID are received by the compliance service. The process may begin at step S800, where one or more dispensed prescription and prescription identifier may be received at the compliance service. It may be determined at step S801 whether receipt of the dispensed prescription and/or prescription identifier is timely. If the determination at step S801 is negative, the compliance service may issue a push failure notice at step S801 and this process may optionally end. If the determination at step S801 is positive, the process may continue to step S803, where notification of the timely receipt may be transmitted (e.g., pushed) from the compliance service. In one embodiment, the notification may be transmitted to a notification engine of the compliance service. The notification engine of the compliance service may be configured to receive one or more notifications and optionally convey the one or more notifications to the intended recipient(s) and/or process(es). In one exemplary embodiment, the notification engine of the compliance service may convey the one or more notifications to a second notification engine which is configured to transmit push notifications corresponding to the one or more notifications.

The compliance service may be configured to import and/or store dispensed prescription and/or prescription identification information at step S804. The compliance service may import and/or store at least a portion of the dispensed prescription and/or prescription identification information locally at the compliance service (e.g., in a local database), at a remote storage location (e.g., an external database), or any combination thereof. At least one of the dispensed prescription and/or prescription identification information may be transmitted (e.g., pushed) to the patient application. The compliance service may then await compliance data at step S806. In one embodiment, the awaited compliance data may correspond to a compliance image and/or metadata message transmitted from a patient application (e.g., as described with reference to step S400). However, compliance data may take the form of any set of information relating to compliance received by the compliance service without departing from the spirit and the scope of the present disclosure.

Figure 9:
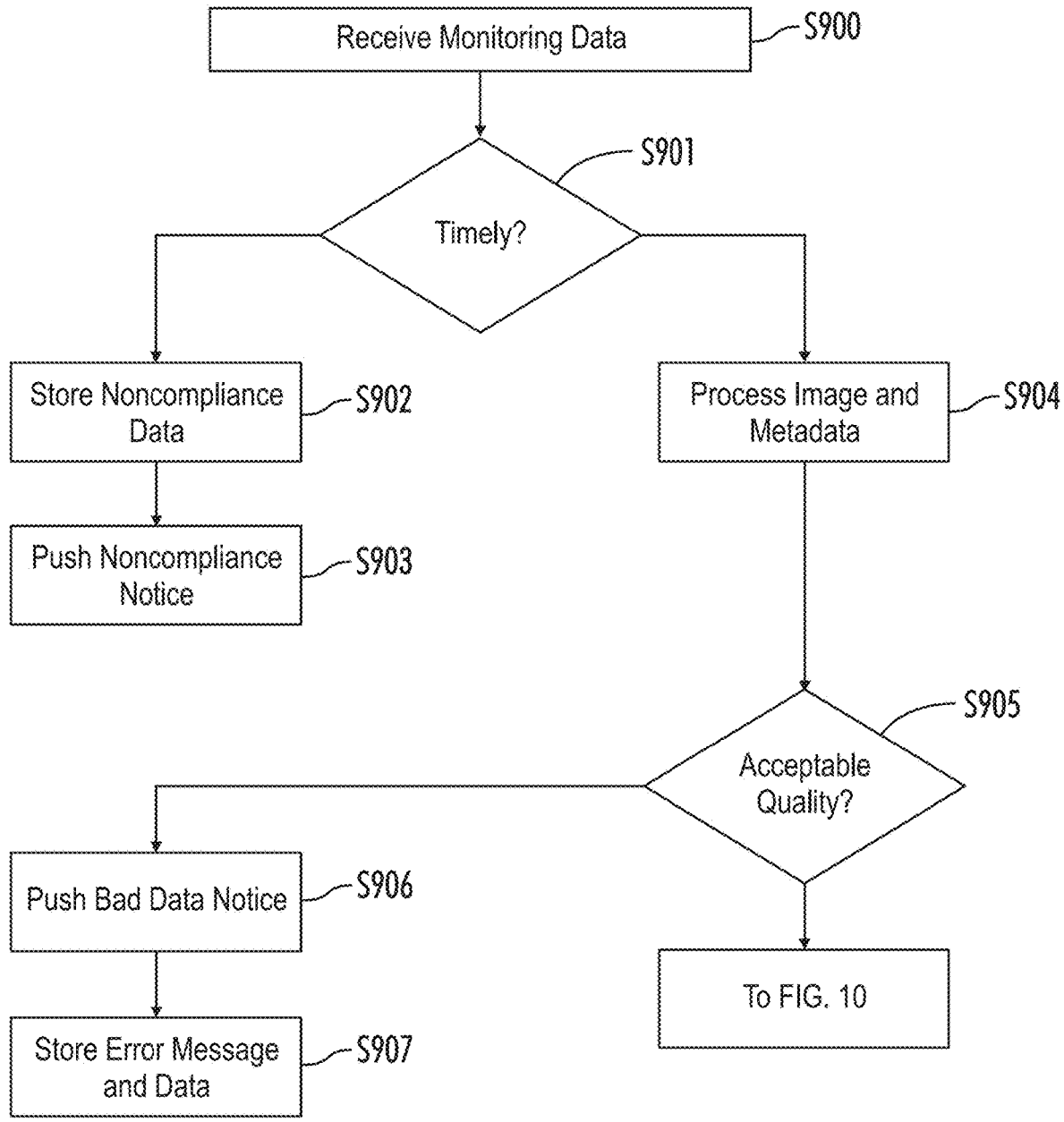
FIG. 9 illustrates an exemplary monitoring process consistent with the present disclosure.

FIG. 9 illustrates an exemplary conformance monitoring process consistent with the present disclosure. The process may begin at step S900, where monitoring data is received by the compliance service. It may be determined at step S901 whether the received monitoring data is timely. If the received monitoring data is not timely received, noncompliance data may be stored at step S902. The noncompliance data may comprise, for example, at least one of an identification of a patient, dispensed prescription, prescription identifier, or any other data associated with a patient and/or prescription. The noncompliance data may be stored in a local and/or remote data storage associated with the compliance service without departing from the spirit and the scope of the present disclosure. After the noncompliance data is stored, a noncompliance notice may be transmitted (e.g., pushed) from the compliance service at step S903. The compliance service may then determine whether monitoring is complete.

If it is determined that the received monitoring data is timely, the process may continue to step S904, where an image and/or metadata received by the compliance service may be processed. In one exemplary embodiment, the received image and/or metadata may be received from the patient application or from any other source. The received image and/or metadata may be stored locally to the compliance service (e.g., in a local database) or may be remotely stored and accessed by the compliance service. The compliance service may determine at step S905 whether the received image and/or metadata are of acceptable quality. If it is determined that the received image and/or metadata are not of sufficient quality (e.g., at least one metric fails to meet a quality threshold), the compliance service may transmit a bad data notice at step S906 (e.g., to a notification engine associated with the compliance service). The compliance service may optionally store at least one of an error message and data corresponding to the bad data notice at step S907 (e.g., in a local and/or remote storage).

Figure 10:
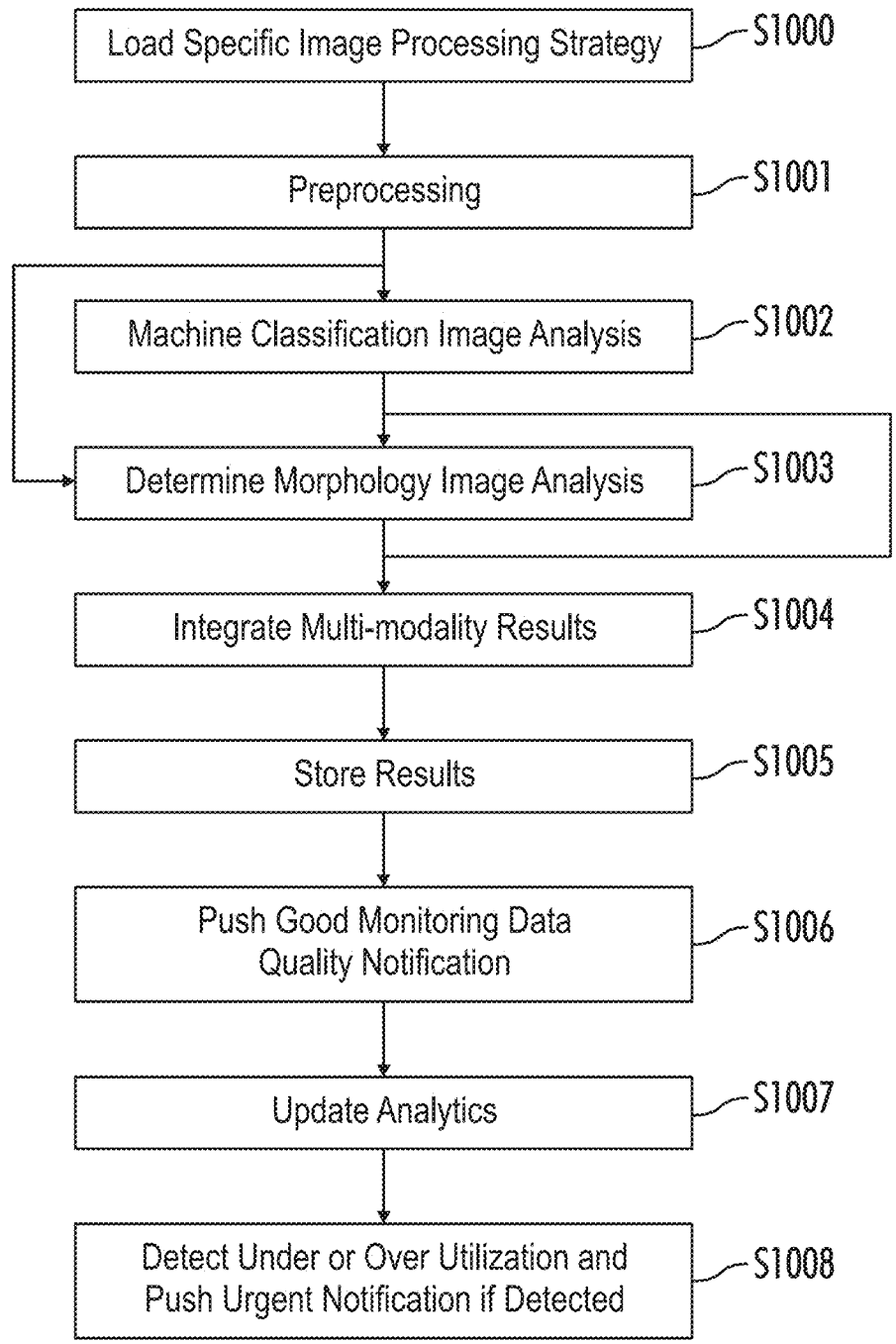
FIG. 10 illustrates an exemplary image processing method in accordance with the present disclosure.

If the received image and/or metadata is determined to be of acceptable quality, the process may continue to step S1000 of FIG. 10, where a specific image processing strategy corresponding to a particular individual or class of packaged product may be loaded by the compliance service. The compliance service may perform preprocessing of the image and/or metadata at step S1001. In various exemplary embodiments, the preprocessing may comprise one or more of, for example, noise, smoothing, thresholding, geometric transformation, edge detection, etc., without departing from the spirit and the scope of the present disclosure. The compliance service may optionally perform machine classification image analysis at step S1002. The compliance service may further optionally perform deterministic morphology image analysis at step S1003. Multi-modality results may be integrated at step S1004, and results linked to one or more monitoring appointments may be stored at step S1005. A notification indicating good monitoring data quality may be transmitted by the compliance service (e.g., to the notification engine of the compliance service). Analytics corresponding to the image analysis and/or packaged product may be updated at step S1007. The compliance service may determine at step S1008 whether there is an under or over utilization of a particular drug by a patient based on the updated analytics. An urgency-stratified notification corresponding to a noted under or over utilization may be transmitted from the compliance service when an under-or-overage detected and may optionally be combined with patient-specific data, medication related data or other factors.

Figure 11:
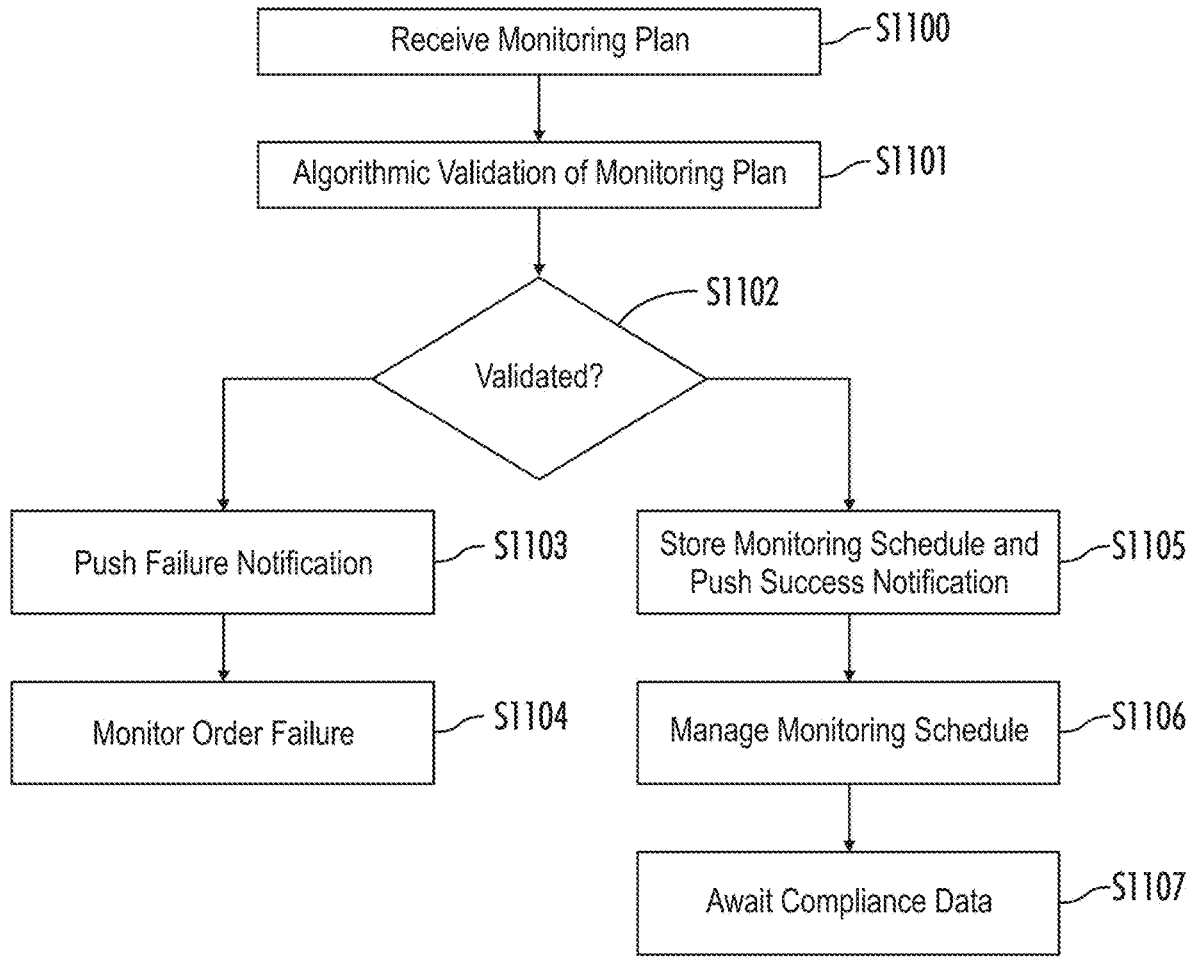
FIG. 11 illustrates an exemplary process corresponding to compliance service operations relating to receipt of a monitoring plan, in accordance with the present disclosure.

FIG. 11 illustrates an exemplary process corresponding to compliance service operations corresponding to receipt of a monitoring plan. The process begins at step S1100, where a monitoring plan is received by the compliance service. The compliance service may perform an algorithmic validation of the received monitoring plan at step S1101. The compliance service may determine at step S1102 whether the monitoring plan is valid. If the monitoring plan is determined to be invalid, the compliance service may transmit a failure notification (e.g., to a notification engine of the compliance service as a monitor order failure, provided as step S1104). If the received monitoring plan is validated by the compliance service at step S1102, the process may continue to step S1105, where a monitoring schedule may be stored either locally and/or remotely by the compliance service, and a success notification may be transmitted by the compliance service (e.g., to a notification engine of the compliance service).

A monitoring schedule may be managed by the compliance service at step S1106. In one exemplary embodiment, the compliance service may provide a monitoring schedule service which is configured to coordinate and manage one or more monitoring schedules. In various embodiments, the monitoring schedule service may track past, present, and/or future scheduled monitoring events and optionally permit access and/or communicate information relating to past, present, and/or future scheduled monitoring events. The compliance service may be configured to allow one or more individuals to observe and/or add, edit, or remove any scheduled event within the monitoring schedule. Individuals or groups permitted to view, add, edit, or remove events may include patients, doctors, pharmacists, nurses, insurance companies, or any other person or entity relating to a scheduled event. After managing the monitoring schedule, the compliance service may await the receipt of compliance data at step S1107.

Figure 12:
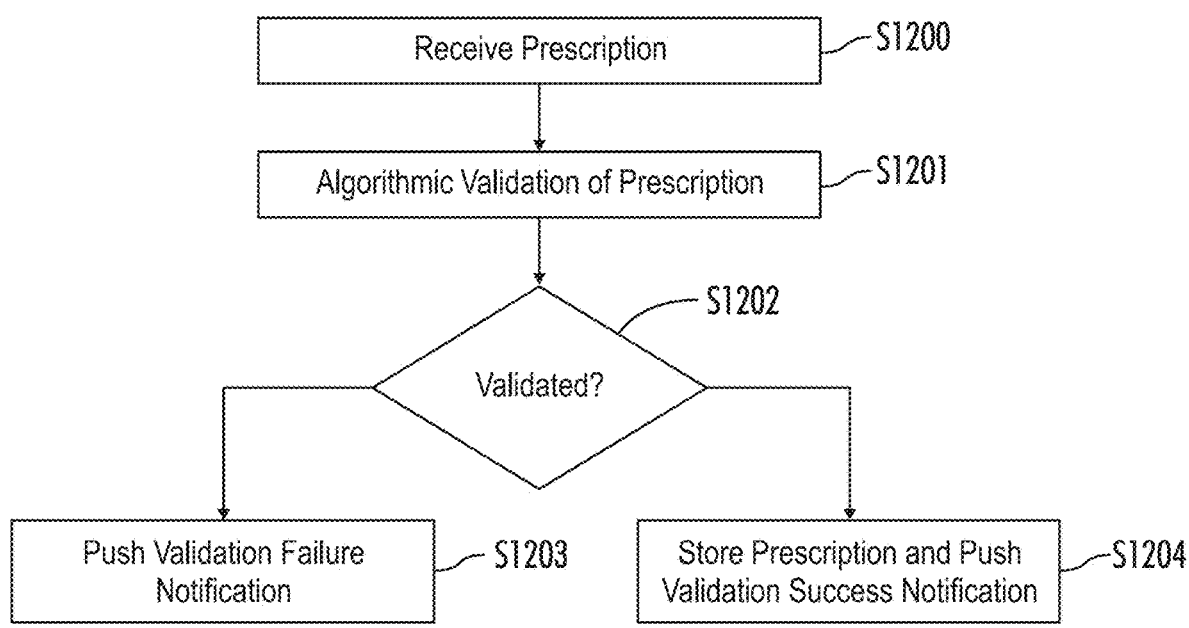
FIG. 12 illustrates an exemplary process corresponding to a compliance service receiving a prescription in accordance with the present disclosure.

FIG. 12 illustrates an exemplary process corresponding to a compliance service receiving a prescription in accordance with the present disclosure. The process may begin at step S1200, where the compliance service may receive a prescription (e.g., from a pharmacy system, a .ehr system, or any other source or provider of prescription data). The compliance service may perform an algorithmic validation of the received prescription at step S1201. If the prescription is not validated at step S1202, the compliance service may transmit (e.g., push) a validation failure message (e.g., to a notification engine associated with the compliance service). If the received prescription is validated, the process may continue by storing prescription information and may transmit (e.g., push) a validation success notification (e.g., to a notification engine associated with the compliance service) at step S1204.

Figure 13:
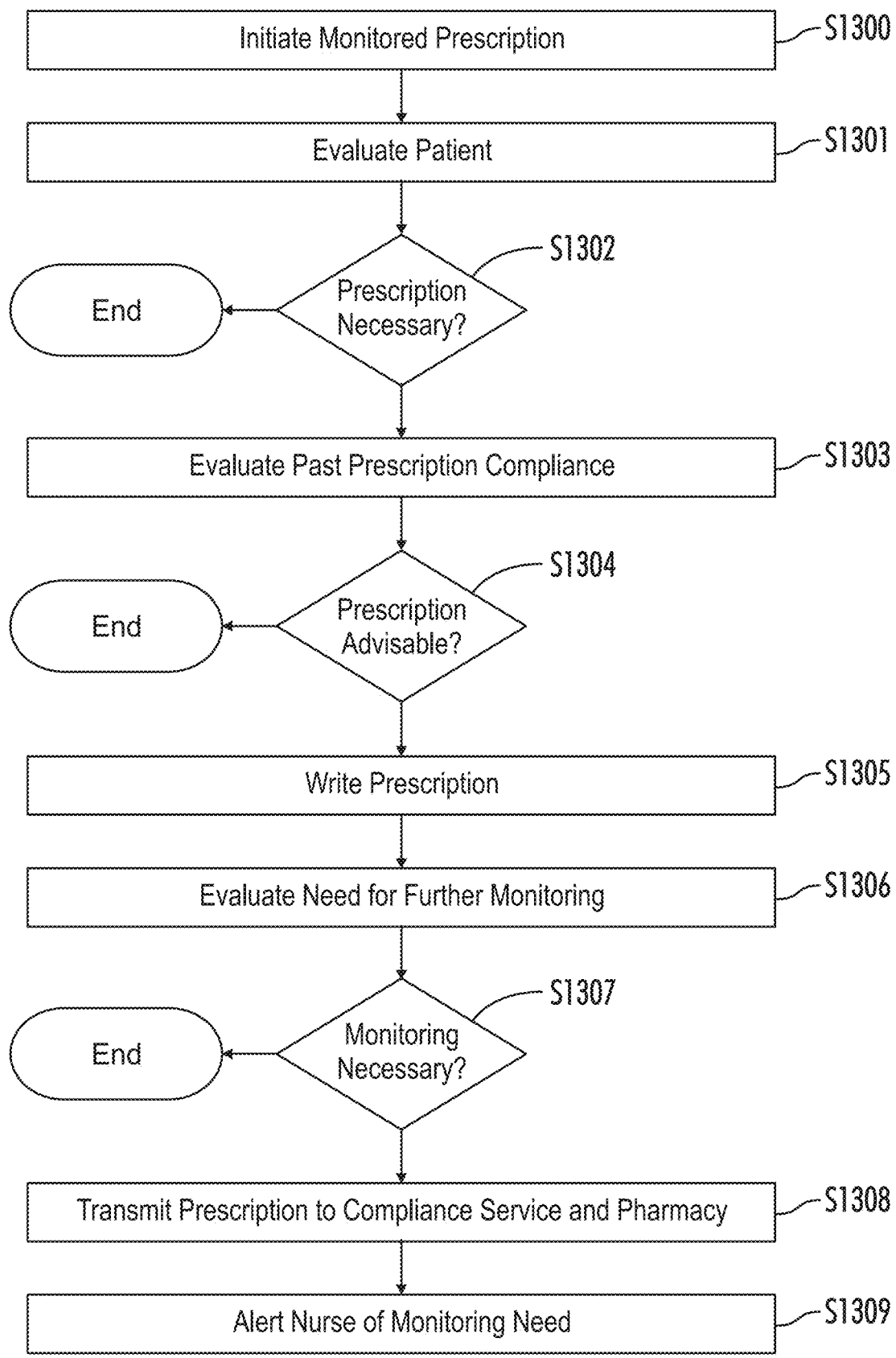
FIG. 13 illustrates an exemplary process corresponding to steps taken when a clinician office initiates a monitored prescription in accordance with the present disclosure.

FIG. 13 illustrates an exemplary process corresponding to steps taken when a clinician office initiates a monitored prescription in accordance with the present disclosure. The process may begin at step S1300, where a professional at a clinician's office (e.g., a physician) initiates a monitored prescription (e.g., by means of a clinician electronic device 30). At step S1301, the professional may evaluate a patient. Based on the patient evaluation, the professional may determine whether a prescription is necessary at step S1302. If no prescription is necessary, this process may end. If it is determined that a prescription is necessary, the process may continue to step S1303, where the professional may evaluate the patient's past prescription compliance, potential risks of noncompliance in the future and potential costs and benefits of prescription compliance monitoring.

Based on the evaluation at step S1303, the professional may determine whether a prescription is advisable at step S1304. If it is determined that a prescription is not advisable, this process may end. If it is determined that a prescription is advisable, the process may continue to step S1305 where the professional may write a prescription for the patient. The professional may evaluate a need for further monitoring at step S1306 and make a determination at step S1307 whether monitoring of the patient's prescription usage is necessary. If it determined that no monitoring is necessary, this process may end. If it is determined that monitoring is necessary, the process may continue to step S1308, where a prescription may be transmitted to the compliance service and to a pharmacy. The professional may optionally alert a second professional (e.g., a nurse) of the need to monitor a patient's prescription drug usage at step S1309.

Figure 14:
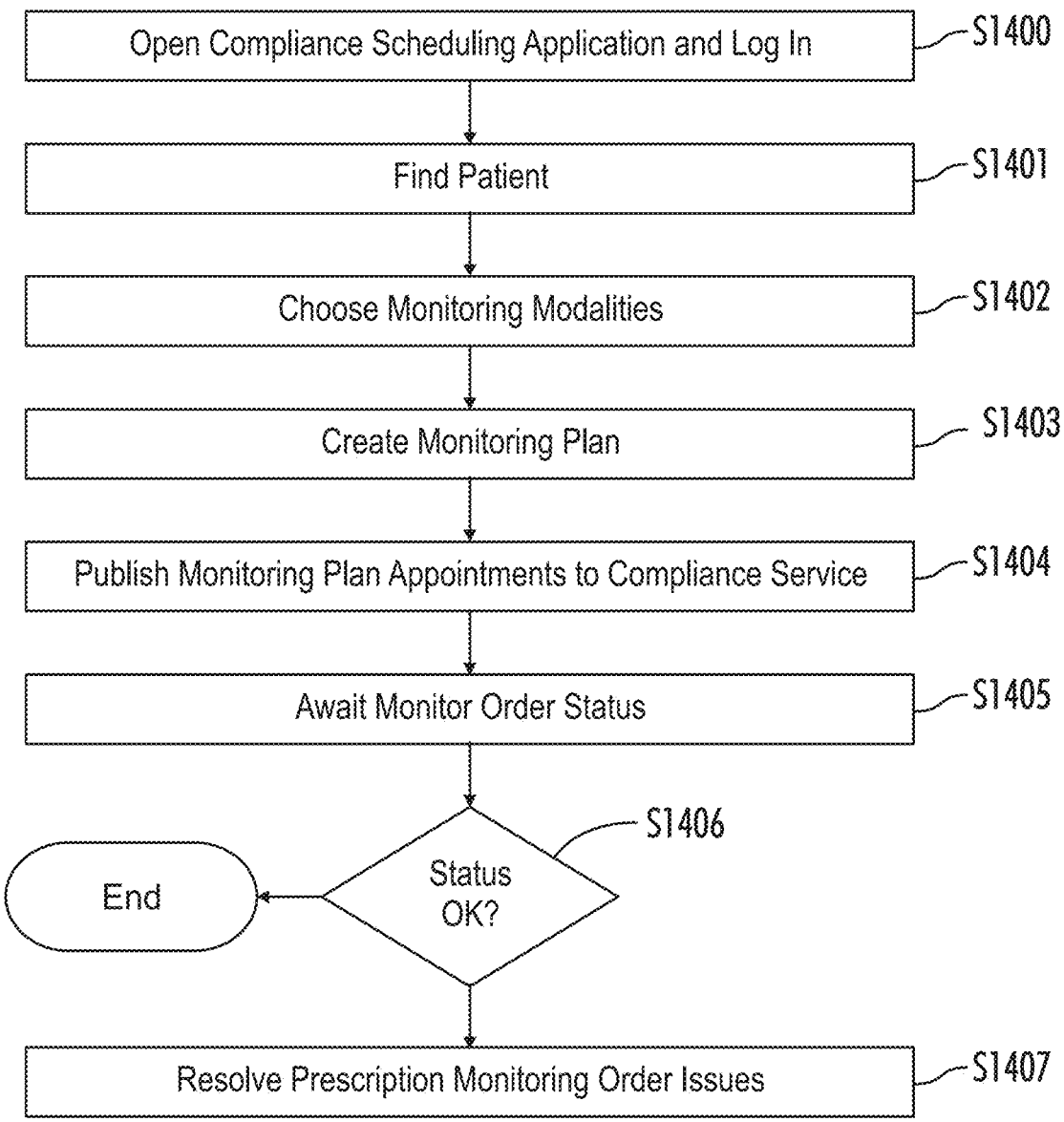
FIG. 14 illustrates an exemplary process of an individual associated with a clinician office creating a monitoring schedule consistent with the present disclosure.

FIG. 14 illustrates an exemplary process of an individual associated with a clinician office creating a monitoring schedule consistent with the present disclosure. The process may begin at step S1400, where a compliance scheduling application may be opened, and a professional (e.g., a physician or nurse) may optionally log into the compliance scheduling application. Using the compliance scheduling application, a professional may locate a particular patient at step S1401. The professional may select one or more monitoring modalities at step S1402. For example, various monitoring modalities may include a named pattern, an enumerated list, may be computer-generated, and/or may be a repeating event. A monitoring plan may then be created at step S1403. Monitoring plan appointments may be published to the compliance service at step S1404.

The professional may receive one or more monitor order messages at step S1405. In one exemplary embodiment, the one or more monitor order messages may be received from a notification engine of the compliance service, and may comprise, for example, a monitor order success or failure message. A monitoring order status may be determined at step S1406. If it is determined that a monitoring order status is acceptable, this process may end. However, if it is determined that a monitoring order status is not acceptable, the process may continue to step S1407, where one or more prescription monitoring order issues may be resolved (e.g., by an individual at the clinician office).

Figure 15:
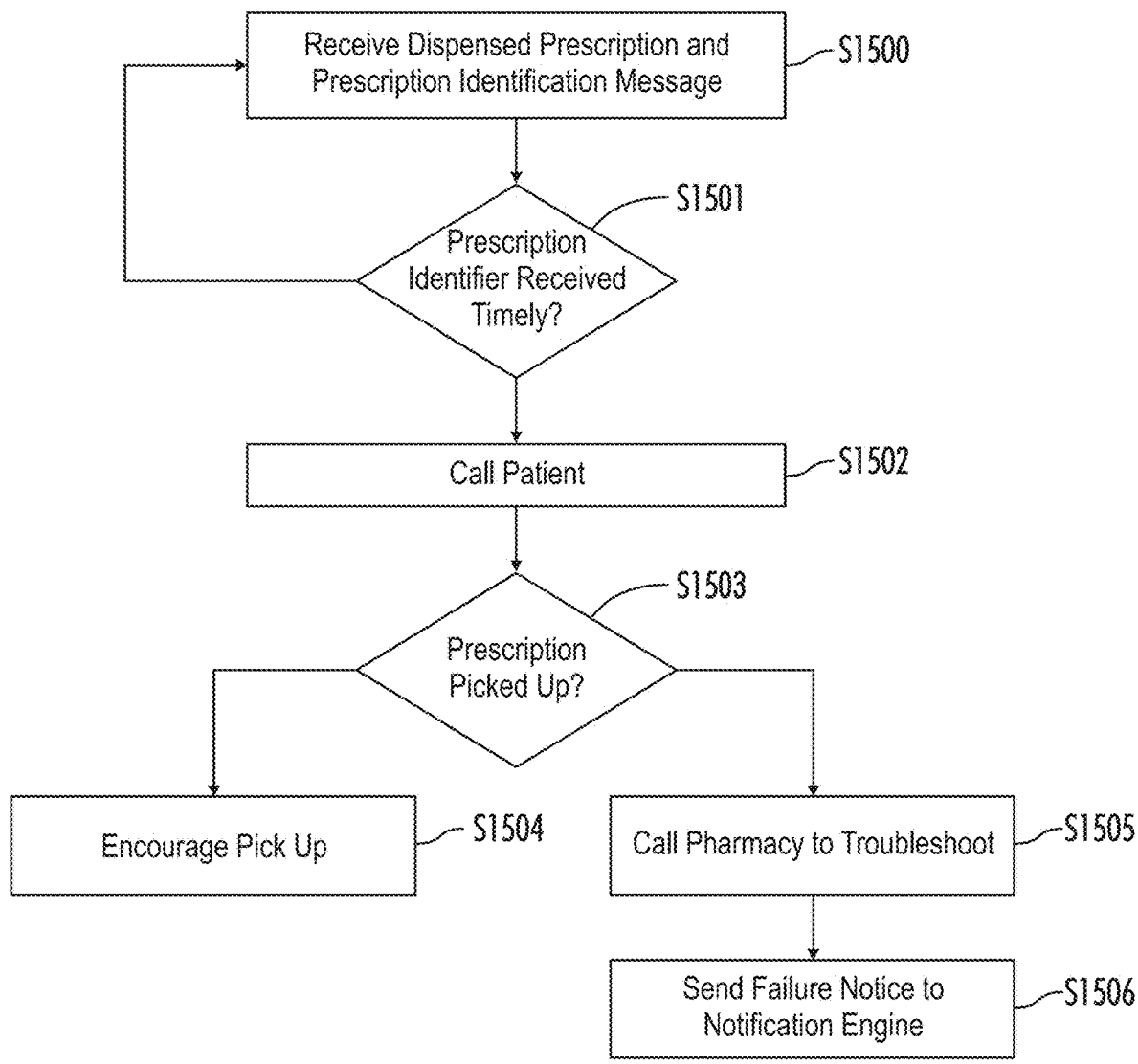
FIG. 15 illustrates an exemplary embodiment of a process of verifying that a patient has picked up a dispensed prescription, in accordance with the present disclosure.

FIG. 15 illustrates an exemplary embodiment of a process of verifying that a patient has picked up a dispensed prescription, in accordance with the present disclosure. The process may begin at step S1500, where a dispensed prescription and/or prescription identification message is received by an individual associated with a clinician's office (e.g., a clerk). It may be determined at step S1501 whether a received prescription identifier was received in a timely manner. If the prescription identifier was received timely, this process may return to step S1500 or the process may end. If it is determined that the prescription identifier was not timely received, the process may continue to step S1502, where the individual may call the patient associated with the prescription identifier. The process may then continue to step S1503 where it may be determined whether the prescription has been picked up. In one embodiment, an amount of time between steps S1502 and S1503 may be a designated threshold, may be a predetermined period of time, or may be spontaneous upon the individual's determination, without departing from the spirit and the scope of the present disclosure.

If it is determined at step S1503 that the prescription has not been picked up, the process may continue to step S1504, where the patient may be encouraged to pick up the prescription (e.g., by either an individual at the clinician's office or by an individual associated with a pharmacy). If it is determined that the prescription has been picked up, the process may continue to step S1505, where an individual associated with the clinician's office may contact the pharmacy to troubleshoot the cause of the non-timely received prescription identifier. A failure notice may be transmitted to a notification engine of the compliance service at step S1506.

Figure 16:
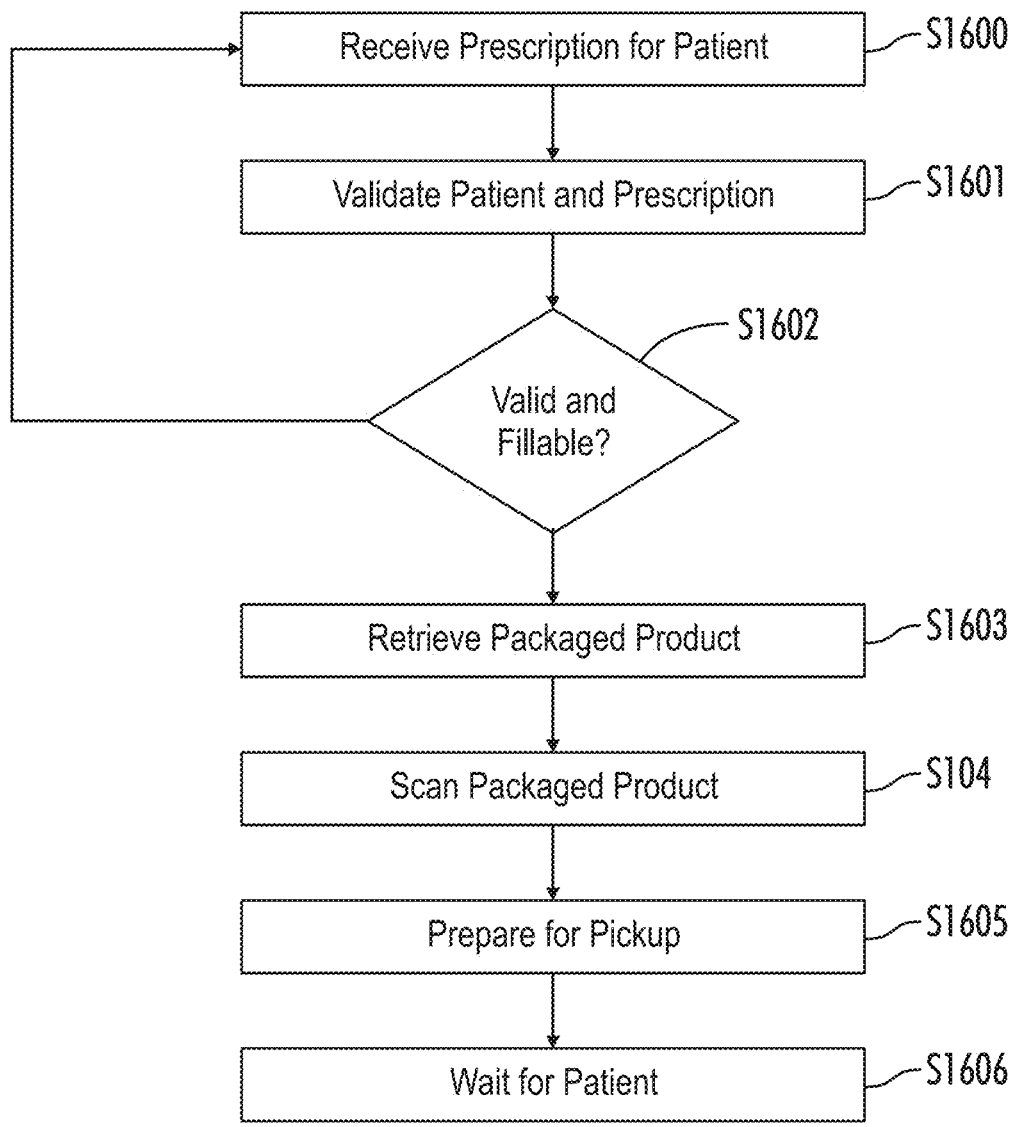
FIG. 16 illustrates an exemplary embodiment of a process for a pharmacy dispensing a prescription in accordance with the present disclosure.

FIG. 16 illustrates an exemplary embodiment of a process for a pharmacy dispensing a prescription in accordance with the present disclosure. The process may begin at step S1600, where a prescription for a patient is received (e.g., at a pharmacy at one or more pharmacy electronic device 40). At step S1601, at least one of the patient and the prescription may be validated (e.g., by a pharmacy tech associated with the pharmacy). At step S1602, it may be determined whether the prescription is valid and fillable. In one embodiment, the determination of whether the prescription is valid and fillable may be performed in association with an individual related to the pharmacy (e.g., a pharmacy tech or dispensing pharmacist). If it is determined at step S1602 that the prescription is either not valid or not fillable, this process may end and/or responsible organization(s) or law enforcement agencies may be notified, and the process may return to step S1600.

If the prescription is determined to be valid and fillable, the process may continue to step S1603, where a packaged product (e.g., pharmaceutical drug associated with the prescription) is retrieved (e.g., by a pharmacy tech from the pharmacy). The packaged product may be scanned at step S1604 and prepared for pickup at step S1605. Once the packaged product has been prepared for pickup, the pharmacy may hold the packaged product and wait for the patient to pick up the packaged product at step S1606.

Figure 17:
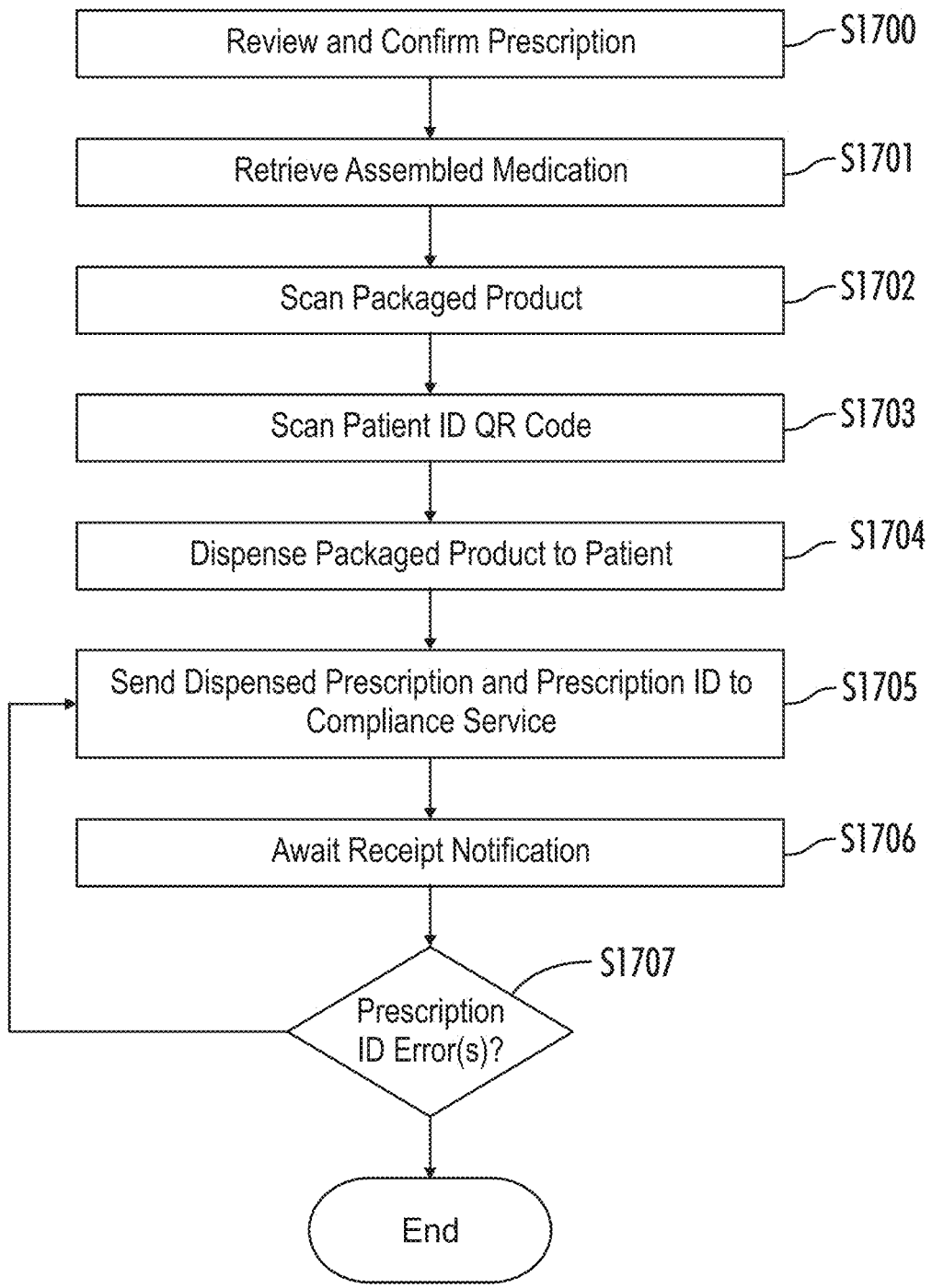
FIG. 17 illustrates an exemplary process of distributing a packaged product to a patient in accordance with the present disclosure.

FIG. 17 illustrates an exemplary process of distributing a packaged product to a patient in accordance with the present disclosure. The process may begin at step S1700, where an individual associated with a pharmacy (e.g., a dispensing pharmacist) may review and confirm a prepared prescription when a patient arrives to pick up the prescription. The individual associated with the pharmacy may retrieve a previously assembled medication at step S1701 and scan the packaged product at step S1702. A patient identifier and/or coded information may be scanned at step S1703. The patient identifier and/or coded information may comprise a QR code in one embodiment. The patient identifier and/or coded information may be used in various embodiments to uniquely identify at least one of the patient and a valid prescription associated with the patient. At step S1704, the packaged product may be dispensed to the patient.

A dispensed prescription and prescription identifier may be transmitted to the compliance service from the pharmacy at step S1705 (e.g., from a pharmacy information system). In one embodiment, the pharmacy information system may await prescription identifier receipt notification at step S1706. In one exemplary embodiment, the pharmacy information system may await receipt of prescription information from a notification engine of the compliance service. After receipt of the prescription identifier receipt notification, a received prescription identifier may be checked for errors at step S1707. If errors are detected at step S1707, the process may return to step S1705. If no errors are detected, this process may end.

Figure 18:
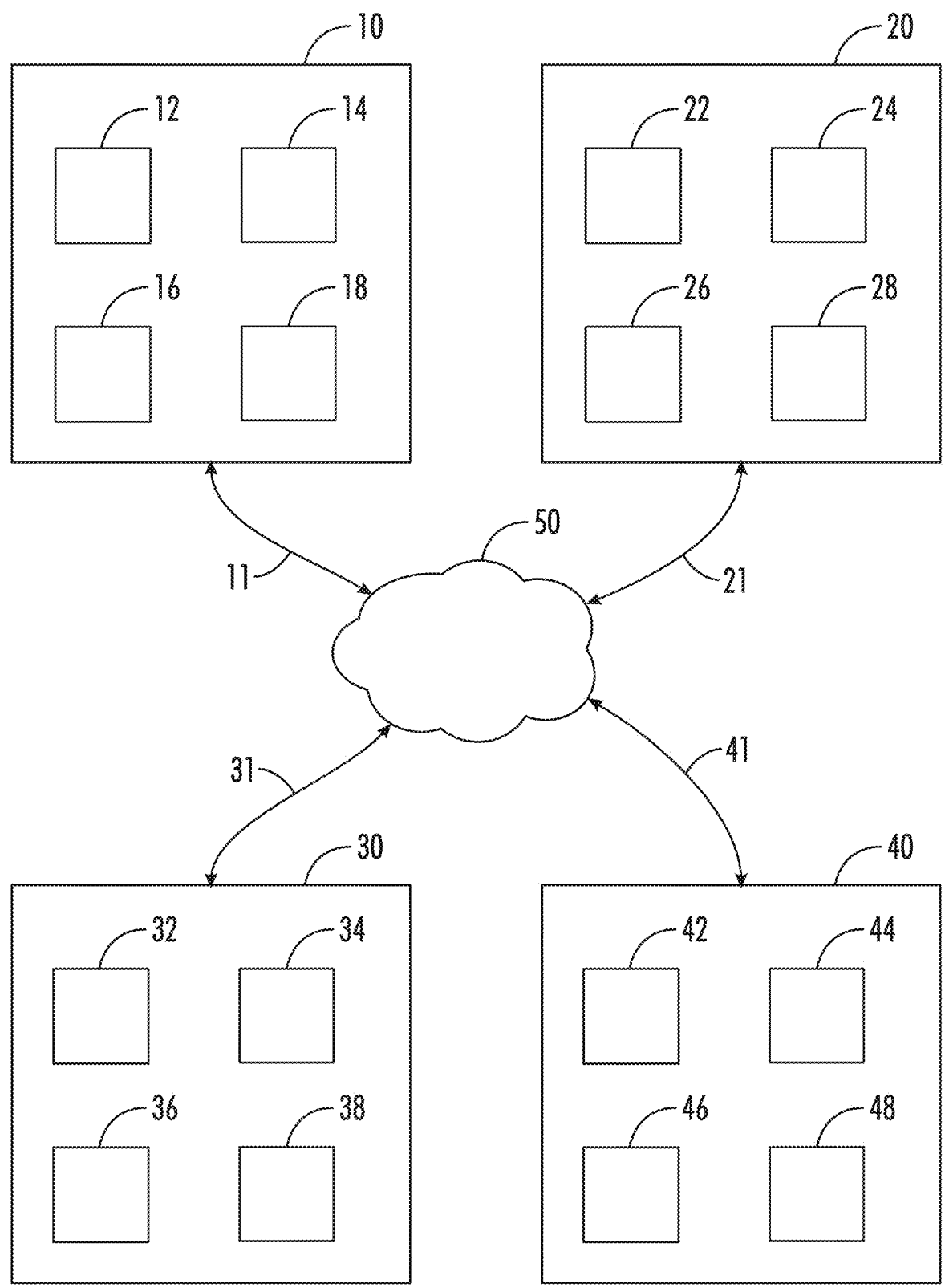
FIG. 18 illustrates an exemplary embodiment of a physical configuration of computing elements in accordance with the present disclosure

FIG. 18 illustrates an exemplary embodiment of an interconnected network consistent with the present disclosure. The interconnected network may comprise a client electronic device 10. The client electronic device 10 may comprise one or more of a microprocessor 12, a storage unit 14, a communications unit 16, and a display unit 18. The communications unit 16 of the client electronic device 10 may be configured to connect to a network 50 via connection 11. In one exemplary embodiment, the network 50 may comprise the Internet, a public network, a private network, or any other communications medium capable of conveying electronic communications. Connection between the communications unit 16 and network 50 may be by wired interface, wireless interface, or a combination thereof, without departing from the spirit and the scope of the present disclosure. In operation, the client electronic device 10 may store one or more sets of instructions in the storage unit 14, which may be executed by the microprocessor 12 to perform the one or more sets of instructions. The display unit 18 may be embodied within the client electronic device 10 or may be either wired or wirelessly-interfaced with the client electronic device 10.

In various exemplary embodiments, the client electronic device 10 may be a desktop computer, a laptop computer, a smart phone, or any other electronic device capable of executing instructions. The microprocessor 12 may take the form of a generic hardware processor, a special-purpose hardware processor, or a combination thereof. In embodiments having a generic hardware processor, the generic hardware processor may be converted to a special-purpose processor by means of executing a particular algorithm for providing a specific operation or result. Client electronic device 10 may be associated with a fixed location or may be capable of being transported, either during operation or while powered off. In one embodiment where the client electronic device 10 is a client's cellular telephone, the client electronic device 10 may be located at a client's premises. In various embodiments, the client electronic device 10 may be operated remotely, and may be configured to obtain or otherwise operate upon one or more instructions stored physically remote from the client electronic device 10 (e.g., via client-server communications and/or cloud-based computing).

One or more compliance services consistent with the present disclosure may be provided by one or more compliance servers 20. Each compliance service 20 may be connected to network 50 via communications link 21 and may comprise one or more of a microprocessor 22, a storage unit 24, a communications unit 26, and/or a display unit 28. Each of the microprocessor 22, storage unit 24, communications unit 26, and/or display unit 28 may respectively correspond to the previously-described microprocessor 12, storage unit 14, communications unit 16, and/or display unit 18 without departing from the spirit and the scope of the present disclosure.

Each compliance server 20 may be associated with a fixed location or may be capable of being transported, either during operation or while powered off. In one embodiment, one or more compliance server 20 may be located at a fixed location and comprise a server. In various embodiments, the compliance server 20 may be operated remotely, and may be configured to obtain or otherwise operate upon one or more instructions stored physically remote from the compliance server 20 (e.g., via client-server communications and/or cloud-based computing).

One or more clinician electronic devices 30 consistent with the present disclosure may be provided by electronic devices. Each clinician electronic device 30 may be connected to network 50 via communications link 31 and may comprise one or more of a microprocessor 32, a storage unit 34, a communications unit 36, and/or a display unit 38. Each of the microprocessor 32, storage unit 34, communications unit 36, and/or display unit 38 may respectively correspond to the previously-described microprocessor 12, storage unit 14, communications unit 16, and/or display unit 18 without departing from the spirit and the scope of the present disclosure.

Each clinician electronic device 30 may be associated with a fixed location or may be capable of being transported, either during operation or while powered off. In one embodiment, one or more clinician electronic device 30 may be located at a fixed location and comprise a desktop computer, or may comprise a moveable laptop or tablet computer in another embodiment. In various embodiments, the clinician electronic device 30 may be operated remotely, and may be configured to obtain or otherwise operate upon one or more instructions stored physically remote from the clinician electronic device 30 (e.g., via client-server communications and/or cloud-based computing).

One or more pharmacy electronic devices 40 consistent with the present disclosure may be provided by electronic devices. In one exemplary embodiment, the one or more pharmacy electronic devices 40 may form at least a part of a pharmacy information system. Each pharmacy electronic device 40 may be connected to network 50 via communications link 41 and may comprise one or more of a microprocessor 42, a storage unit 44, a communications unit 46, and/or a display unit 48. Each of the microprocessor 42, storage unit 44, communications unit 46, and/or display unit 48 may respectively correspond to the previously-described microprocessor 12, storage unit 14, communications unit 16, and/or display unit 18 without departing from the spirit and the scope of the present disclosure.

Each pharmacy electronic device 40 may be associated with a fixed location or may be capable of being transported, either during operation or while powered off. In one embodiment, one or more pharmacy electronic device 40 may be located at a fixed location and comprise a desktop computer, or may comprise a moveable laptop or tablet computer in another embodiment. In various embodiments, the pharmacy electronic device 40 may be operated remotely, and may be configured to obtain or otherwise operate upon one or more instructions stored physically remote from the pharmacy electronic device 40 (e.g., via client-server communications and/or cloud-based computing).

Figure 19:
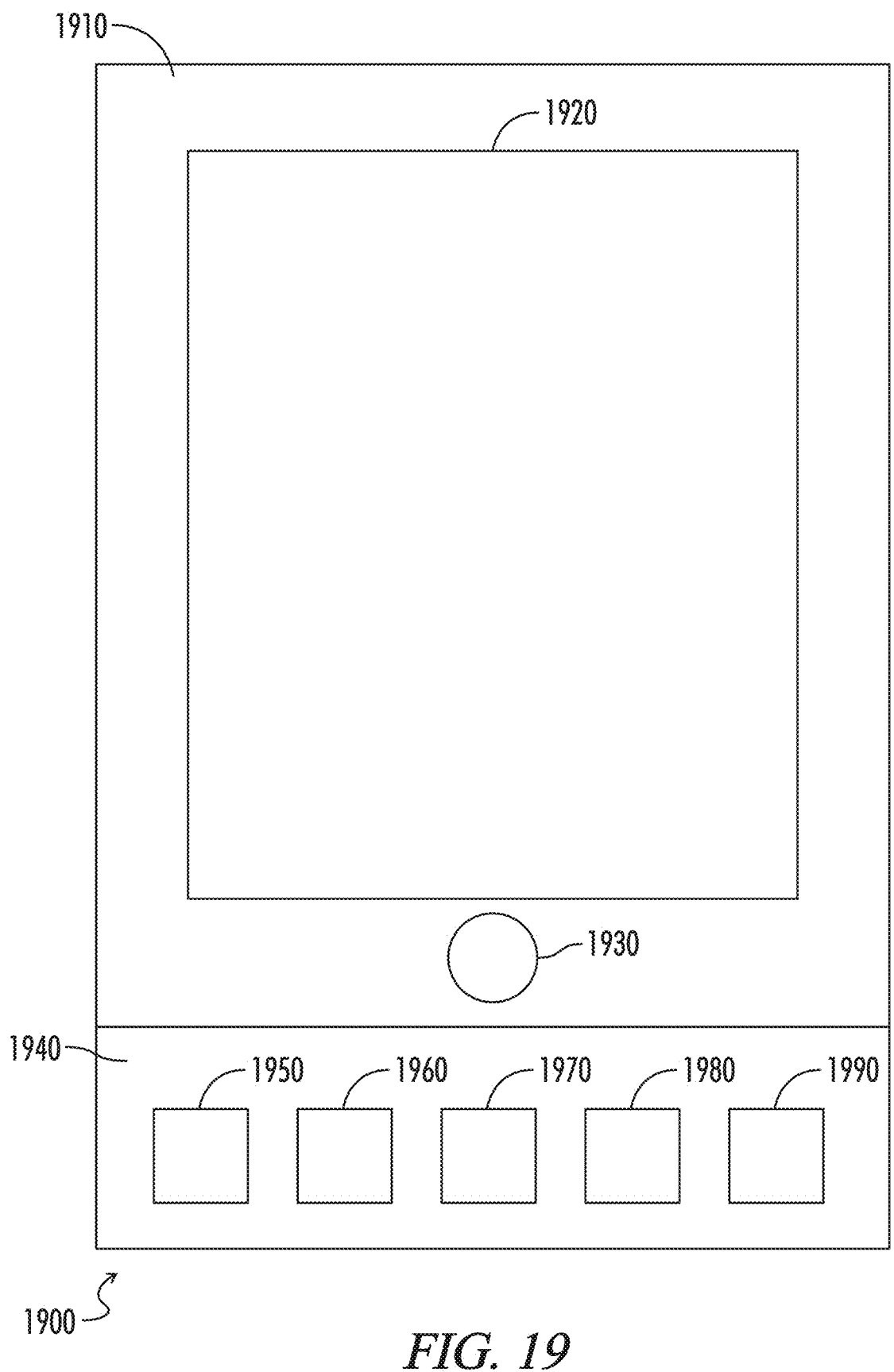
FIG. 19 illustrates a client electronic device implementing a conformance verification process via an acquisition process according to an exemplary embodiment.

FIG. 19 illustrates a client electronic device 1900 implementing a conformance verification process via an acquisition process according to an exemplary embodiment. The client electronic device 1900 includes a body 1910 having a plurality of sections thereupon. For example, the exemplary embodiment of FIG. 19 includes a capture area 1920, an action area 1930, and a menu area 1940. The body 1910 may include a physical body of the client electronic device 1900, a physical display portion of the client electronic device 1900 (e.g., a liquid crystal display (LCD) or light emitting diode (LED) display unit), or any other physical or software-implemented structure or interface provided by the client electronic device 1900.

The capture area 1920 may include a portion of the body 1910 configured to provide image, video, or other data to a user of the client electronic device 1900. For example, in one embodiment, the capture area 1920 may be used to convey visual information associated with the taking of or result of an image capture operation. The image capture operation may be associated with, for example, a pill count confirmation process as described herein and as used for verifying conformance with a given prescription. In addition, or as an alternative, at least a portion of the capture area 1920 may include the ability to select a previously taken, stored, or accessible image for use in conformance verification. For example, the client electronic device 1900 may enable a user of the client electronic device 1900 to access or link to confirmation data such as images, videos, or other confirmation data stored at a storage of the client electronic device, at a device or location external to the client electronic device 1900, or a combination thereof.

The client electronic device 1900 may include an action area 1930 configured to enable a selection of capture data and/or cause the client electronic device 1900 to capture verification information associated with the capture area 1920. For example, in one exemplary embodiment, the action area 1930 is a camera capture button configured to operate in conjunction with a camera of the client electronic device 1900. When the action area 1930 is selected during operation, the client electronic device 1900 may be configured to record image, video, or other verification information associated with the capture area 1920. The captured verification information may then be used as a part of a conformance verification process.

The client electronic device 1900 may further include a menu area 1940. The menu area 1940 may include one or more selectable sections. For example, in the embodiment illustrated in FIG. 19, the menu area 1940 may include an acquire section 1950, a schedule section 1960, an information section 1970, a history section 1980, and a settings section 1990. Selection of the acquire section 1950 may cause the client electronic device to operate in an acquire mode. For example, information associated with a camera or other information acquisition device coupled to or otherwise accessible by the client electronic device 1900 may be presented to a user via the capture area 1920 when the acquire section 1950 is selected (and/or as a default during operation or when scheduled).

The process of operating in the acquisition mode is further described below with reference to FIG. 26.

Figure 20:
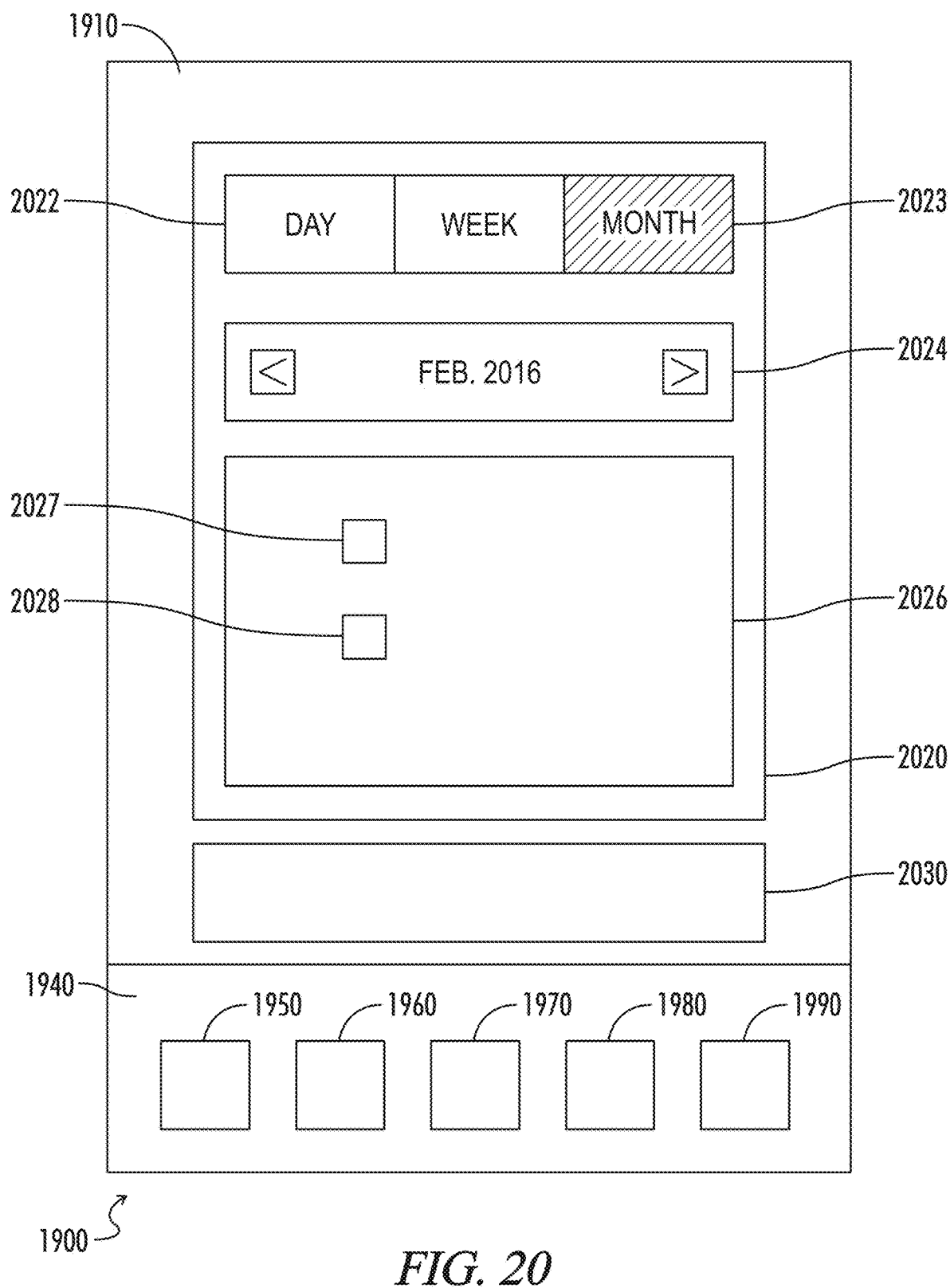
FIG. 20 illustrates a client electronic device implementing a schedule operation according to an exemplary embodiment.

FIG. 20 illustrates a client electronic device 1900 implementing a schedule operation according to an exemplary embodiment. The client electronic device 1900 includes a schedule section 2020 at a display portion thereof. The schedule section 2020 includes at least one of a time reference selector 2022, an index selector 2024, and a calendar section 2026. The client electronic device 1900 further includes a scheduled event display section 2030. The time reference selector 2022 may present one or more time reference values selectable by a user to identify a time reference for display within the calendar section 2026. For example, the time reference selector 2022 may include the values "Day," "Week," and/or "Month," optionally along with any other time reference value. An output of the calendar section 2026 may thus be modified according to a time reference value selected from the time reference selector 2022 (e.g., a user can switch between daily schedules, weekly, schedules, and monthly schedules displayed in the calendar section 2026 by selecting an appropriate time reference value within the time reference selector 2022. A current and/or default selection of a time reference value of the time reference selector 2022 may be visually distinguishable by a user of the client electronic device 1900, for example by providing a shaded selection area 2023.

The client electronic device 1900 may further include the index selector 2024. The index selector 2024 may provide one or more visual indicia 2025 selectable by a user to modify an output of the calendar section 2026. For example, the index selector 2024 may display one unit of a time reference associated with the time reference selector 2022 and one or more selectable operations associated with the calendar section 2026. In the exemplary embodiment illustrated in FIG. 20, the index selector conveys a setting associated with "Feb. 2016" (e.g., a current or other month in conjunction with the shaded selection area 2023) and includes visual indicia 2025 configured to allow selections for increasing or decreasing the display month in the index selector 2024 and at least a portion of the output provided by the calendar section 2026.

The calendar section 2026 is configured to convey one or more temporal representations 2027 associated with at least one of the time reference selector 2022 and the index selector 2024. For example, in the exemplary embodiment illustrated by FIG. 20, the calendar section 2026 conveys a monthly view of the month of February 2016, including one or more days of the month as the one or more temporal representations 2027. In one exemplary embodiment, the calendar section 2026 includes one or more action identifiers 2028. The one or more action identifiers may be associated with the one or more temporal representations 2027 in various embodiments. For example, the one or more action identifiers may be color-coded status icons associated with one or more temporal representations 2027. In various embodiments, each action identifier 2027 may convey a status associated with one or more temporal representation 2027.

In one exemplary embodiment, each action identifier 2027 may be used to identify both the presence of a scheduled action (e.g., by visual representation on the calendar section 2026), and a corresponding status. The corresponding status may be identified, for example, by color. For example, a green status color of an action identifier 2028 may represent that an action event was scheduled at an identified temporal representation 2027, and that the status associated with the action event is or was acceptable. On the other hand, if the status associated with the action event was not successful, the action identifier 2028 may be a red color. For future scheduled action events, the action identifier 2028 may be a separate color, such as grey, in one or more embodiments.

As described above, the calendar section 2026 may be used to visually convey one or more temporal periods associated with at least one of the time reference selector 2022 and the index selector 2024. For example, in the embodiment illustrated by FIG. 20, the calendar 2026 includes a visual representation of the month of February 2016, including a plurality of temporal representations 2027 and corresponding action identifiers 2028. During operation, a user of the client electronic device 1900 may select one or more of the plurality of temporal representations 2027. Additionally or alternatively, a current date or other default setting may be used to automatically determine the selected temporal representation 2027. When one or more temporal representations 2027 are selected, information corresponding to one or more corresponding action identifiers 2028 may be visually conveyed via the scheduled event display section 2030. For example, in the embodiment illustrated by FIG. 20, the scheduled event display section 2030 may convey that a random pill count is due today.

The scheduled event display section 2030 may optionally include one or more user-selectable sections or other notification means (such as a pop-up notification or other information-conveying capability) for permitting a user to enter information and/or perform one or more operations corresponding to at least one action identifier 2028. For example, in one exemplary embodiment, the scheduled event display section 2030 may indicate a random pill count. A user of the client electronic device 1900 may select at least a portion of the scheduled event display section 2030 to enable the user to perform at least one operation corresponding to the random pill count, such as executing the client electronic device 1900 in an acquire mode as described above with reference to FIG. 19.

Figure 21:
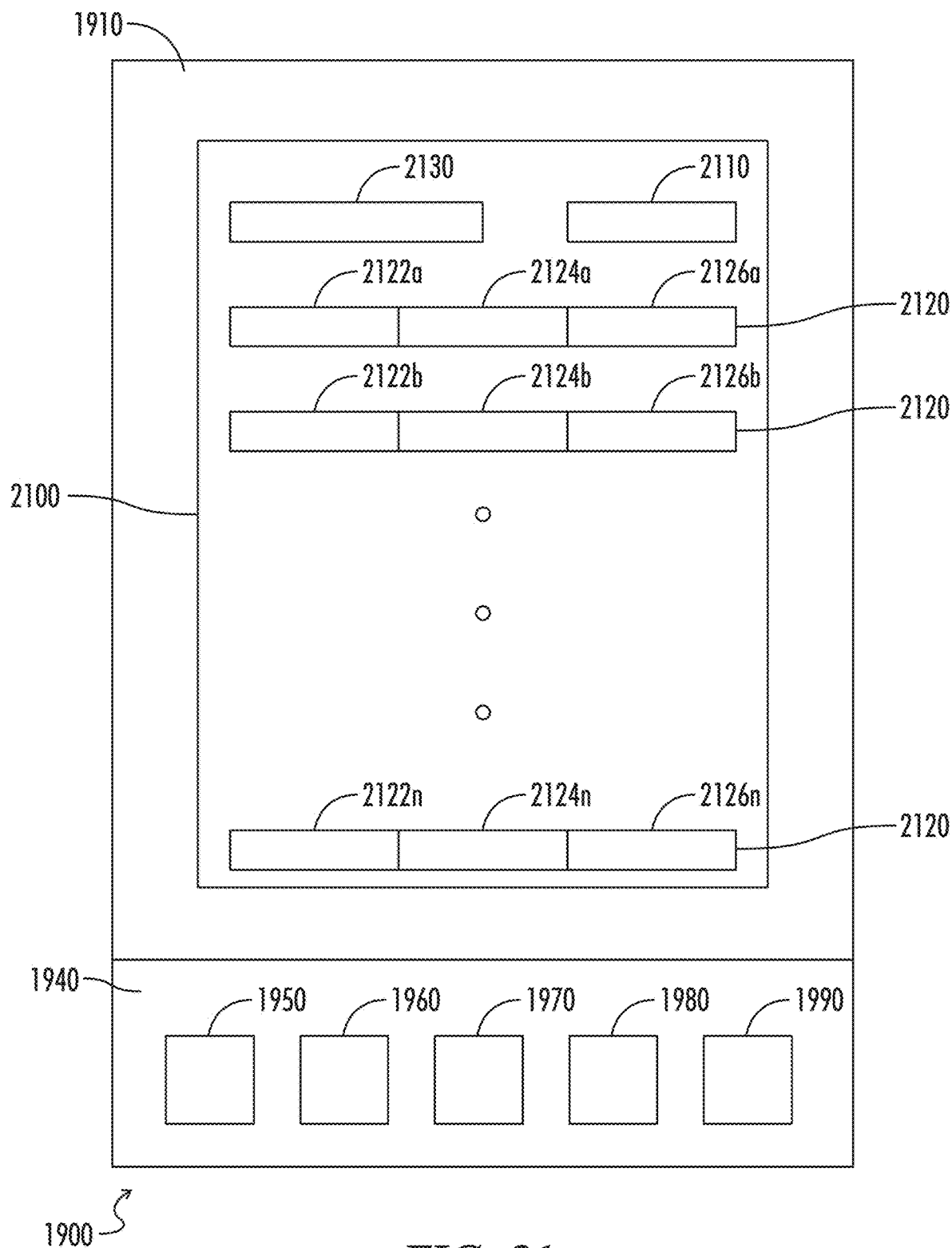
FIG. 21 illustrates a client electronic device implementing an information operation according to an exemplary embodiment.

FIG. 21 illustrates a client electronic device 1900 implementing an information operation according to an exemplary embodiment. The client electronic device 1900 includes an information section 2100 at a display portion thereof. The information section 2100 is configured to provide at least one set of information associated with a user and/or prescription data. The information section may include a details section 2110 configured to provide at least one of scheduled and actual usage information associated with one or more prescriptions. For example, during operation when the details section 2110 is selected, the information section 2100 may be configured to display at least one of prescription data, such as dosage amount and dosage interval, and user prescription history data, such as historical prescription usage data and prescription dates/amounts.

The information section 2100 further includes at least one set of usage data 2120. The usage data 2120 includes at least one of temporal data 2122, medication data 2124, and conformance data 2126. The embodiment illustrated in FIG. 21 includes a plurality of usage data 2120, each including at least one of temporal data 2122 (identified as 2122*a-n*), medication data 2124 (identified as 2124*a-n*), and conformance data 2126 (identified as 2126(*a-n*)).

The temporal data 2122 of the usage data 2120 may provide one or more time reference values associated with a particular action. For example, one or more of temporal data 2122*a-n* may be associated with an action value such as a required pill count operation. In various embodiments, at least one of the temporal data 2122*a-n* may be a date and/or time indicator associated with a past, present, or future pill count operation. At least one of the temporal data 2122*a-n* may optionally be configured to convey an action status associated with an associated action operation (e.g., a green check to indicate successful pill count operation, a red 'X' to indicate an unsuccessful pill count operation, etc.). When displayed to a user of the client electronic device 1900, at least a portion of a visual representation associated with temporal data 2122 may be selectable by a user, for example to obtain further information associated with the corresponding action (e.g., to view stored or otherwise obtainable information regarding the action operation or lack thereof).

The medication data 2124 of the usage data 2120 may provide one or more sets of medication data associated with a particular action. For example, one or more of medication data 2124*a-n* may be associated with an action value such as a required pill count operation. In one exemplary embodiment, at least one of the medication data 2124*a-n* may represent a medication name and/or dosage amount. During operation, each of the medication data 2124 of the usage data 2120 may correspond to one or more medications.

The conformance data 2126 of the usage data 2120 may provide information regarding a conformance value associated with a particular action. One or more of conformance data 2126*a-n* may be associated with an action value such as a required pill count operation. In one exemplary embodiment, one or more of the conformance data 2126*a-n* may include a visual indicator associated with a current pill count compared to expected usage. For example, the visual indicator may include a visual indicator configured to show whether a current pill count is higher, lower, or on pace with an expected pill count.

The information section 2100 may further include an action identifier 2130. The action identifier 2130 may provide information regarding an action type corresponding to the usage data 2120. For example, the action identifier may display "Pill Counts" when the usage data 2120 provided by the information section corresponds to pill count action data.

Figure 22:
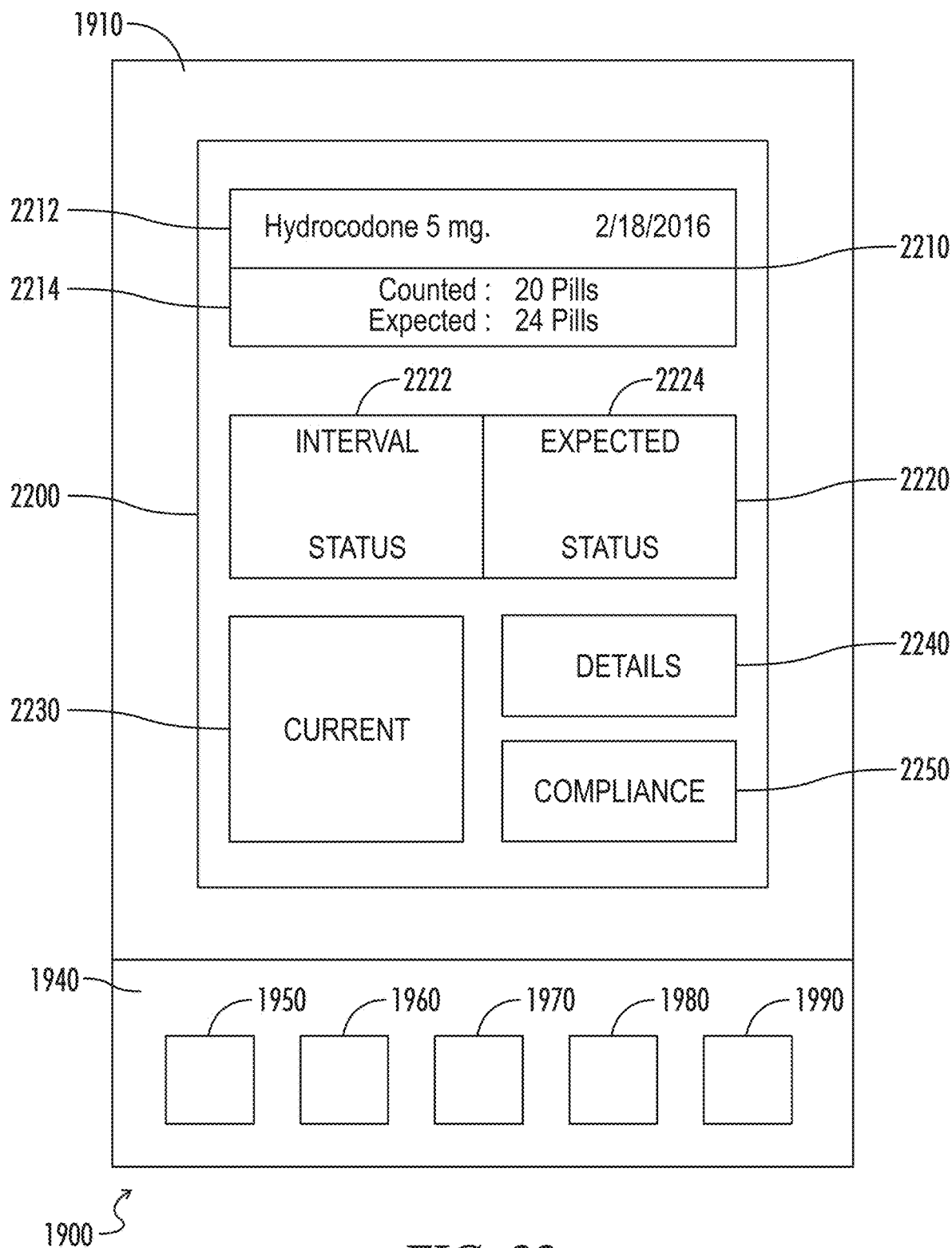
FIG. 22 illustrates a client electronic device implementing an action details operation according to an exemplary embodiment.

FIG. 22 illustrates a client electronic device 1900 implementing an action details operation according to an exemplary embodiment. The client electronic device 1900 includes a details section 2200 at a display portion thereof. The details section 2200 includes at least one of a medication section 2210, a usage section 2220, a current data section 2230, a current data details section 2240, and a compliance section 2250.

The medication section 2210 includes at least one of medication identification section 2212 and a pill count section 2214. The medication identification section 2212 may include information relating to at least one of a medication type, a dosage amount, a prescription date, a current prescription status date, or any other information relating to a particular medication and/or information relating to a user of the medication or usage information. For example, in the embodiment illustrated by FIG. 22, the medication information section includes an identification of the medication as Hydrocodone, the dosage as 5 mg, and the current prescription status date as Feb. 18, 2016. In this embodiment, the current prescription status date provides the date of the most current pill count data. The pill count section 2214 may include any information regarding a prescription pill count, including a counted pill value, an expected pill value, or any other pill count information. For example, in the embodiment illustrated by FIG. 22, the pill count section 2214 includes an expected pill count number and the current counted pill number (e.g., corresponding to the current prescription status date as of the last pill count).

The details section 2200 may further include a usage metric section 2220. The usage metric section 2220 may be configured to provide usage metric data associated with at least one medication. Information conveyed by the usage metric section 2220 may be textual, graphical, or any combination thereof. For example, in the embodiment illustrated by FIG. 22, an interval use section 2222 may provide a graphical representation of a user's medication usage within a particular interval, and a monthly use section 2224 may provide a graphical representation of a user's medication usage within a current or historical month.

The details section 2200 may further include a current information section 2230. The current information section 2230 may be configured to provide one or more indications of current data relating to a particular action and a particular medication. For example, in one exemplary embodiment, the current information section 2230 may provide data corresponding to the most current pill count, such as displaying the most recent pill count acquisition data (e.g., in the form of the image, video or other acquired data). A current information details section 2240 may be provided to provide additional information relating to the most recent pill count data information provided by the current information section 2230. For example, the current information details section 2240 may provide at least one of a pill count due date/time, a date and/or time when the information contained in the current information section 2230 was transmitted, a date and/or time when the information contained in the current information section 2230 was received by a conformance verification system, or any other information relating to the data contained in the current information section.

The details section 2200 may further include a compliance section 2250. The compliance section 2250 may be configured to convey a compliance status to a user of the client electronic device 1900. The compliance status presented at the compliance section 2250 may include multiple compliance statuses, for example including at least one of an interval compliance status, a monthly compliance status, a yearly compliance status, an overall compliance status, or the like.

One or more of the data displayed via the details section 2200 may be stored locally at the client electronic device 1900, stored remotely from the client electronic device 1900, or a combination thereof. For example, in one exemplary embodiment, at least one of the data elements presented via the details section 2200 may be obtained in real-time or previously obtained from a remote server and/or cloud-based storage system. The client electronic device 1900 may be configured to request at least one of the data elements presented via the details screen, may be configured to receive a data push from an external source, or a combination thereof, without departing from the spirit and the scope of the present disclosure.

Figure 23:
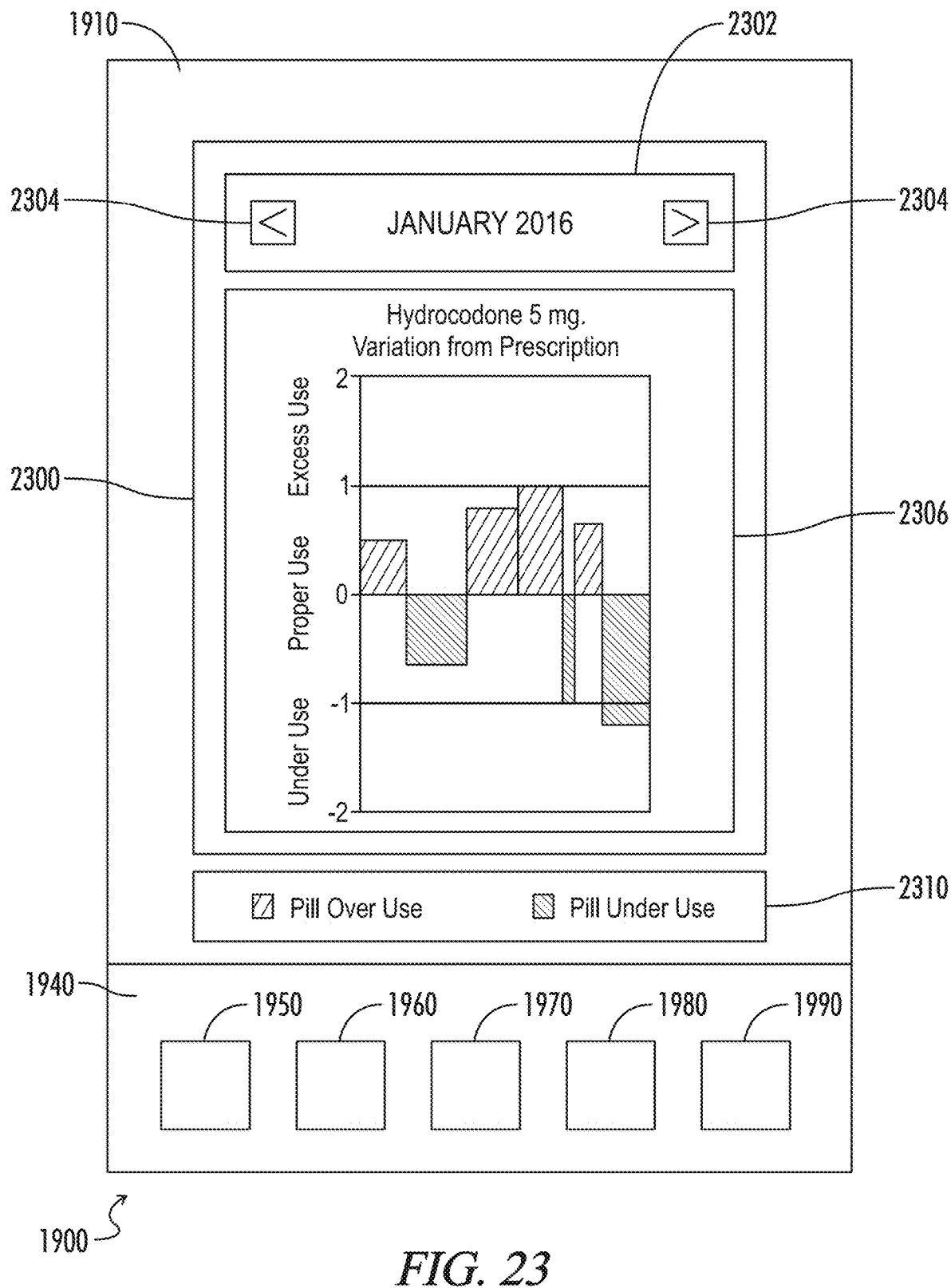
FIG. 23 illustrates a client electronic device implementing a graphing operation according to an exemplary embodiment.

FIG. 23 illustrates a client electronic device 1900 implementing a graphing operation according to an exemplary embodiment. The client electronic device 1900 includes a graph section 2300 at a display portion thereof. The graph section 2300 may be configured to convey at least a portion of medication, user, and/or user history information, along with any additional information. For example, in the embodiment illustrated by FIG. 23, the graph section 2300 may include an identification of a medication for Hydrocodone and a dosage amount associated with a prescription.

The graph section 2300 may include at least one index selector 2302 configured to provide one or more visual indicia 2304 selectable by a user to modify an output of a representation 2306. For example, the index selector 2302 may provide a time period corresponding to the representation and one or more selectable operations 2304 associated with the representation 2306. In the exemplary embodiment illustrated in FIG. 23, the index selector 2302 conveys a setting associated with "January 2016" and includes visual indicia 2304 configured to allow selections for increasing or decreasing the display period in the index selector 2302 and at least a portion of the output provided by the representation 2306.

The graph section 2300 may be configured to provide information relating to at least one medication and at least one action. For example, the graph section 2300 may include a textual, graphical, or other representation 2306 of a medication history. Information used to create the representation 2306 may be obtained from one or more pill count actions and corresponding data. In one exemplary embodiment, the representation 2306 is a graph of pill usage over time, based at least in part upon current and expected pill count values.

The representation 2306 may, in various embodiments, implement at least one of color coding and axis-based ranging for graphically displaying at least one of normal usage, over-usage, and/or under-usage of at least one medication based on data from one or more pill counts. For example, in the embodiment illustrated in FIG. 23, a pill over use condition may be distinguished from a pill under use condition via color coding, and excessive use and/or under use conditions may be specified by one or more particular ranges (e.g., as plotted on a vertical axis of the representation, or any other means of graphically or textually conveying over- or under-usage). At least one of pill over use, excess use, pill under use, and under use criteria may be specified by at least one of a physician, a pharmacist, a pill provider, a monitoring service, a government entity, or any other person or organization capable of monitoring or limiting access or use to one or more medications or prescriptions.

Figure 24A:
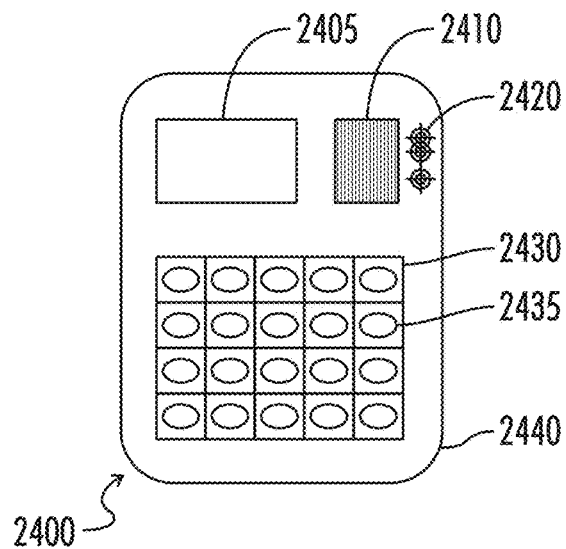
FIGS. 24A-B illustrate examples of blister packaging in accordance with one or more embodiments.
Figure 24B:
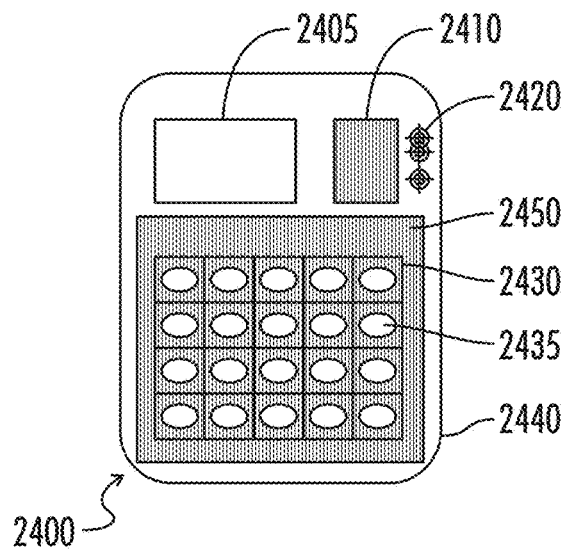

FIGS. 24A-B illustrate example blister packaging in accordance with one or more embodiments. The blister package 2400 of FIG. 24A optionally includes at least one information section 2405. The information section 2405 may include a QR code, a bar code, plain text, image data, or any other means of conveying information capable of use consistent with the present disclosure. The information section 2405 may be used to uniquely identify a particular blister package 2400 or to include any data or information intended to be used by the client electronic device 1900 or any other processing or operating element of the disclosed system. Additionally or alternatively, the information section 2405 may store or otherwise include information relating a particular prescription, medication, pill attribute, or any other information capable of use with the present disclosure.

In addition or alternative to the information section 2405, the blister package 2400 may include an identifier 2410. As previously described, the identifier 2410 may be used to uniquely identify a particular blister package 2410. Additionally or alternatively, the identifier 2410 may store or otherwise include information relating a particular prescription, medication, pill attribute, or any other information capable of use with the present disclosure. The blister package 2400 may optionally include a color or size reference section 2420. The color or size reference section 2420 may be used in various embodiments for calibration and/or confirmation of one or more visual aspects of the blister package 2400 when imaged or otherwise acquired, for example during an acquire mode as previously described.

The blister package 2400 may further include one or more spaces 2430. In one embodiment, a size and/or shape of the one or more spaces 2430 may correspond to at least one attribute of a medication associated with the blister package 2400 (e.g., at least one of the spaces 2430 may be configured having a sufficient size to contain or enclose at least a portion of a medication associated with the blister package 2400. In one embodiment, information contained within or referenced by the identifier 2410 may include at least one parameter associated with at least one of the spaces 2430.

Although described with reference to a space, it should be appreciated that one or more of the spaces 2430 may form an enclosure configured to enclose at least one medication 2435. In such an embodiment, the one or more spaces 2430 forming an enclosure may be configured to be opened or otherwise manipulated to obtain the at least one medication 2435 contained therein. In one exemplary embodiment, the one or more spaces 2430 may be configured to implement a visual indicator when a medication 2435 enclosure has been opened or tampered with. For example, the blister package 2400 may include at least a portion of a surface material 2440 within the one or more spaces 2430 which, when exposed to light or air, changes physical appearance and/or conveys a predetermined message or indicator.

In one exemplary embodiment, at least one of the one or more spaces 2430 includes a designated space or surface area of the blister package 2400. A presence, size, and/or location of each space 2430 may be predetermined (e.g., and stored in the identifier 2410) or may be dynamically determined using an acquire mode of the client electronic device 1900 or by accessing a remote data source such as a data server or cloud-based storage network. The client electronic device 1900 may be configured to obtain at least one parameter associated with the blister package 2400 and to use the at least one parameter to perform at least one action. For example, the client electronic device 1900 may be configured to obtain a pill profile stored within the identifier 2410 and/or obtained from a storage of the client electronic device 1900 or a remote device, and may perform a pill counting operation using an image, video, or other data acquired by the client electronic device 1900 in an acquire mode by processing the acquired image, video, or other data in accordance with the pill profile data (e.g., a size, shape, or color of a particular medication pill, etc.).

One or more metadata elements may be used to describe or assist with aspects of the submission not necessarily included in a photo, for example to identify securely the sending device and user. One or more sets of metadata may include, for example, a device ID, a device certificate, a person ID, a person certificate, an application version, a submission date/time, a calendar appointment ID, or any other information associated with a submission. In various embodiments, the metadata may be implemented as a two-part payload. The metadata may be variously configured to be included in at least a portion of data of submitted data, or may be stored or otherwise obtainable from one or more sources external to the submitted data. In one or more embodiments, a client electronic device may have stored thereon or otherwise have access to one or more sets of data configured to be used as or in conjunction with data or submitted data. For example, in one exemplary embodiment, the client electronic device may have copies of a first digital certificate, a device ID, a person ID, a second digital certificate, application version information, calendar appointment ID, or any other set of information capable of use in the manner described herein.

Although described with reference to a blister package, it should be appreciated that one or more inserts or external sources of information may be used as at least a portion of the blister package 2400, either in whole or in part. For example, in one embodiment, the blister package 2400 may be implemented by a particular card or sheet of paper intended to be placed in proximity, above, below, or beside one or more pills, blister package 2400, or blister packages 2400 for use, for example in a pill counting operation. In such embodiments, at least one of the information section 2405 and/or identifier 2410 may be provided on the card and/or sheet of paper. Although described with reference to a card or sheet of paper, any material or object capable of being imaged or having data otherwise obtained either therefrom may be used.

Although described as a single particular card or sheet of paper, at least one portion of the particular card or sheet of paper may be predetermined or pre-printed, and at least one portion of the particular card or sheet of paper may be dynamically generated and/or presented to medication user at any time. Furthermore, at least one particular card or sheet of paper may be generated and/or provided to a medication user by any entity capable of monitoring medication usage of the medication user, or by the compliance service or client electronic device 1900 (e.g., a doctor pharmacist, etc.). For example, in one exemplary embodiment, one or more sheets may be provided to a medication user by a pharmacist at the time that a medication is delivered to the medication user, and at least a portion of a particular card or sheet may be dynamically generated or otherwise provided to the medication user at a later time for use in a pill count (e.g., at least one identifier may be provided to a medication user at the time of a pill count operation to ensure that the medication user could not pre-record conforming pill count images). At least a portion of a particular card or sheet of paper may be provided for download by the client electronic device 1900, and may, in one exemplary embodiment, be printed by the medication user for use in an acquire mode. Additionally or alternatively, the at least a portion of a particular card or sheet of paper may include a digital signature, authorization, or element used in conjunction with the acquire mode.

The blister package 2400 of FIG. 24B includes at least one of the information section 2405, identifier 2410, color or size reference section 2420, one or more spaces 2430, and surface material 2440. The blister package 2400 of FIG. 24B further includes one or more markings 2450. In one exemplary embodiment, the one or more markings 2450 are printed or otherwise visible on the surface material 2440 of the blister package 2400. However, as previously described, at least one of the one or more markings 2450 may be separate from or in addition to one or more others of the one or more markings 2450, and may be dynamically generated and/or provided to or obtainable by a medication user at any time.

Although described herein with reference to a blister packaging (e.g., blister packaging 2400) having one or more information sections, identifiers, or markings (e.g., information section 2405, identifier 2410, one or more markings 2450), it should be appreciated that implementations consistent with the present disclosure may process one or more sets of acquired data either with or without one or any of the information sections, identifiers, or markings. For example, in one embodiment, a compliance service may be configured to receive an image, video or other data providing only pill data (e.g., an image or video containing only images of pills). The compliance service may be configured, for example, to perform medication conformance verification using at least one of pill data (such as pill size, shape, color, etc.) stored locally to the compliance service or available from an external source, and profile information associated with at least one of the medication user, one or more medication attributes, a pharmacist, etc. Furthermore, the compliance system may use multiple forms of acquired data from one or more sources to determine conformance. For example, in one exemplary embodiment, an image of one or more pills obtained from a client electronic device 1900 may be used in conjunction with a weight measurement of the one or more pills from the client electronic device 1900 or a separate device. The compliance service may further require any form of data synchronization (such as matching timestamps for multiple data sets or sources or visual indication of common timing) for reaching a compliance determination.

Figure 25A:
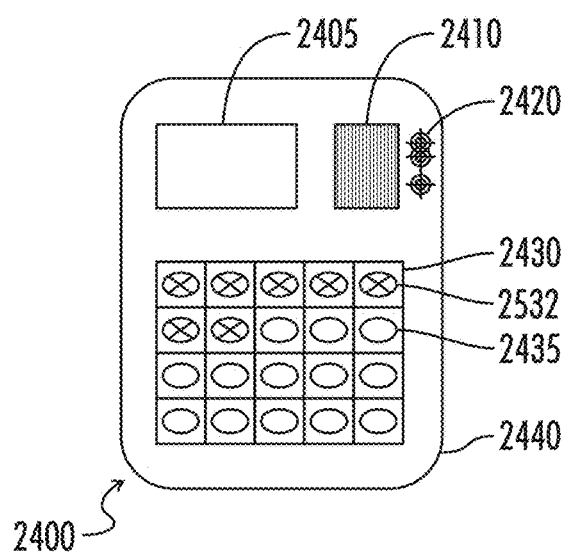
FIGS. 25A-B illustrate blister packages having one or more medication pills removed or tampered with in accordance with exemplary embodiments.
Figure 25B:
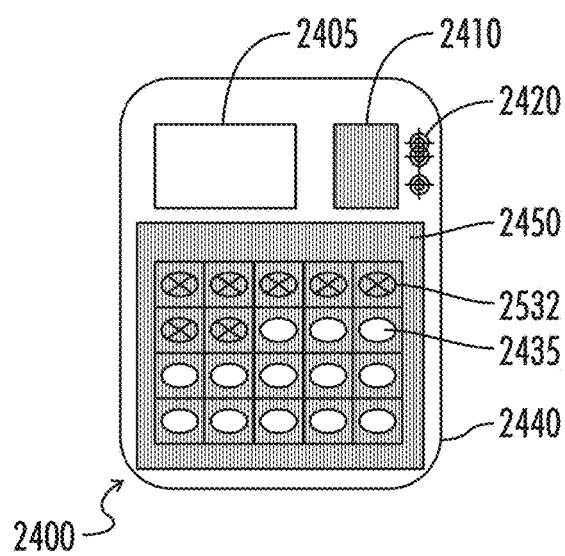

FIGS. 25A-B illustrate blister packages 2400 having one or more medication pills removed or tampered with. The blister package 2400 of FIG. 25A includes at least one of the information section 2405, identifier 2410, color or size reference section 2420, one or more spaces 2430, and surface material 2440. The blister package 2400 of FIG. 25A further includes seven empty or tampered with spaces 2532 of the one or more spaces 2430, each either missing a pill or having been tampered with. As previously described, when opened or tampered with, each of the one or more spaces 2430 may be configured to provide visual indicia for use with the systems described herein. For example, at least a portion of the surface material 2440 or a portion of at least one space 2430 may be configured to display evidence of opening or tampering. Although illustrated with visual crosses through the empty or tampered with spaces 2532, it should be appreciated that any means of visual indicia may be used, including, for example, color changes, printed indicia, graphics, or any other means of conveying information.

Similarly, the blister packaging 2400 of FIG. 25B may implement visual indicia of missing pills and tampering, for example also using the one or more markings 2450 described with respect to FIG. 24B. At least a portion of the one or more markings 2450 may be provided by at least one of the one or more spaces 2430 or at an area associated with at least one of the one or more spaces 2430. For example, at least a portion of the one or more markings 2450 may be located on at least one surface of the one or more spaces 2430, may be located on the surface material 2440, may be located on a surface of at least one medication, may be located at any associated physical or virtual location, or any combination thereof. Furthermore, at least a portion of the one or more markings may be provided at a front or a back surface of the blister package 2400. In practice, one or more surfaces of a blister package 2400 may be required to be acquired for a verification operation (e.g., a front surface of the blister package 2400 may contain at least a portion of the one or more markings 2450, a rear surface of the blister package 2400 may contain at least a portion of the one or more markings 2450, at least one surface of a medication associated with at least one space 2430 may include at least a portion of the one or more markings 2450, or any combination thereof).

Similarly, a pill verification method (e.g., using an acquire mode of a client electronic device 1900) in accordance with the present disclosure may be performed by obtaining data and/or verifying medication presence, absence, or information from one or more surfaces of the blister package 2400 and/or medication 2435 within the at least one space 2430. Furthermore, two or more verification requirements may be required prior to verification. For example, a pill size and pill color may be required for verification in addition to verification of non-opening and non-tampering of one or more of spaces 2430 to be counted.

Figure 26:
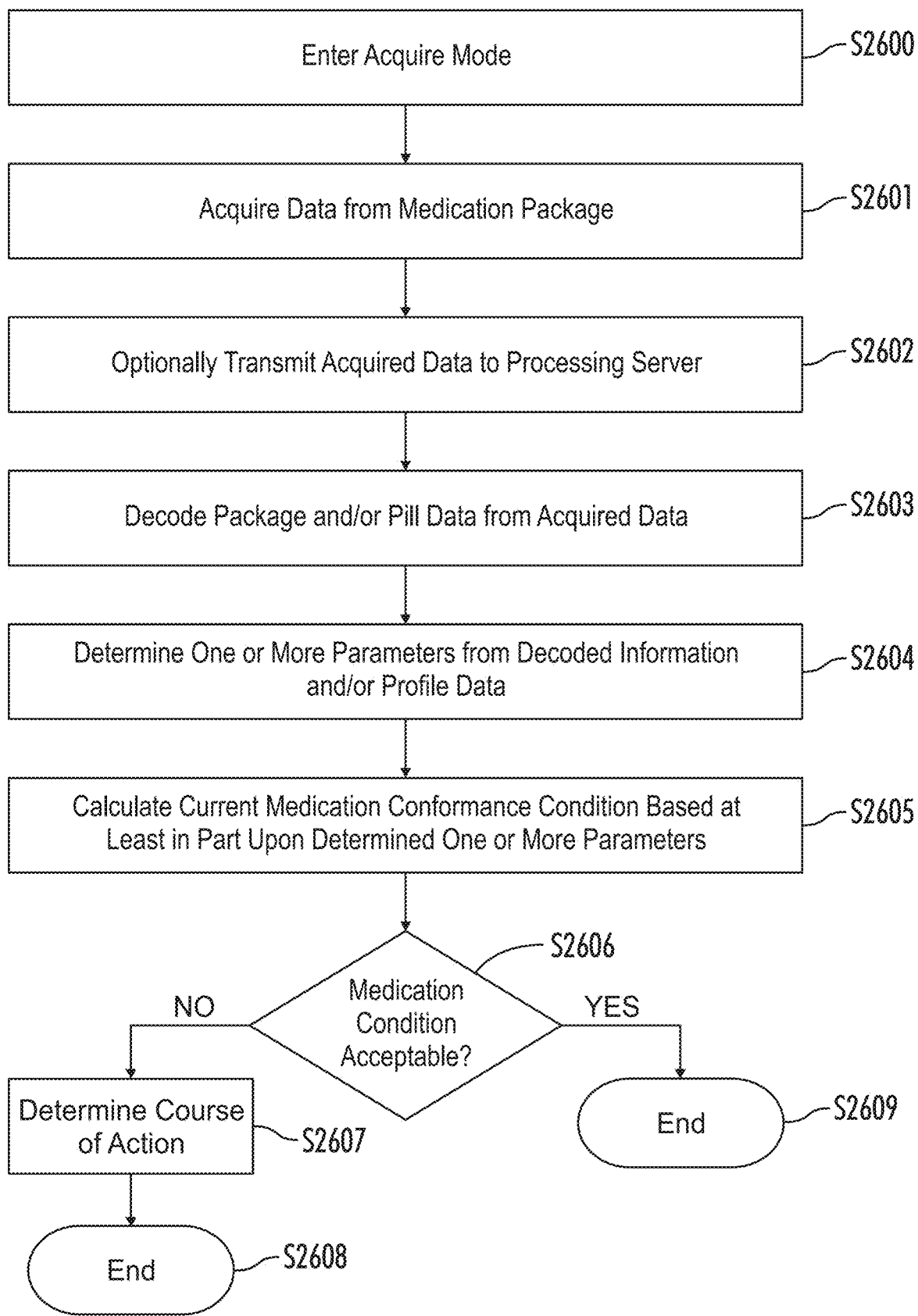
FIG. 26 illustrates a flowchart providing a process for pill count verification according to an exemplary embodiment.

FIG. 26 illustrates a flowchart providing a process for pill count verification according to an exemplary embodiment. The process begins at a step S2600, where the client electronic device 1900 enters an acquire mode. The client electronic device acquires data from a medication package at step S2601 in the manner previous described herein. The process continues to a step S2602, where data acquired by the client electronic device 1900 is optionally transmitted to a processing entity. The processing entity may be a local or remote to the client electronic device, and may include a local processor, a remote server, a cloud-based network, or any combination thereof. The processing entity then decodes at least one of package and pill data from the acquired data at step S2603. The process continues to step S2604, where one or more parameters are determined from at least one of the decoded information and profile data.

In one exemplary embodiment, one or more parameters are decoded from an image, video, or metadata of the image or video obtained during the acquire mode. Additionally or alternatively, one or more parameters may be identified, obtained, or otherwise processed according to at least a portion of profile data associated with at least one of a medication user, a pharmacist, a doctor, a prescription, a medication attribute, or any combination thereof. The non-decoded one or more parameters may be stored, for example, locally at a storage of the client electronic device 1900, at a remote storage, at a cloud-based storage network, or any combination thereof.

Once the one or more parameters are determined, the process continues to step S2605, where a current medication condition is calculated based at least in part upon the determined one or more parameters. The determined one or more parameters may include, for example, a starting pill count, a current pill count, or any attribute or operational requirement associated with at least one of the medication package and/or prescription. The process then continues to step S2606, where it is determined whether the calculated medication conformance condition is acceptable.

If it is determined that the calculated medication conformance condition is not acceptable, the process continues to step S2607, where a course of action is determined and/or undertaken. For example, a medical professional and/or pharmacist may be notified if the calculated medication conformance condition is not acceptable, and the medication user may optionally be required to bring in at least a portion of their prescribed medication when out of conformance. The course of action may be escalated based at least in part upon the particular medication whose use is being monitored, based on the medication user's history, and/or any other criteria desired. The course of action may include, for example at least one of providing a notification to a user of an upcoming or failed conformance, notifying an individual or group (e.g., a nurse or caretaker) of nonconformance and causing the individual or group to contact the user regarding the nonconformance, requesting a "wellness check" by authorities, requiring a user to rectify the noncompliance (for example by taking a photograph of remaining medication), or any other action intended to confirm compliance or ensure the health or safety of the user.

One benefit of an escalating course of action protocol is that the protocol permits expedited feedback from a user regarding medication compliance. For example, if a user has stopped taking a monitored medication for any reason (e.g., potential side effect, co-occurrence of not feeling well, etc.), an appropriate authority may appropriately persuade the user to continue taking the medication, or detect and mitigate complications or adverse drug interactions at an earlier period of time than the user's next scheduled doctor's appointment.

After the course of action is determined, undertaken, and/or completed, the process may end at step S2608. If it is determined that the calculated medication conformance condition is acceptable, the process ends at step S2609.

Figure 27:
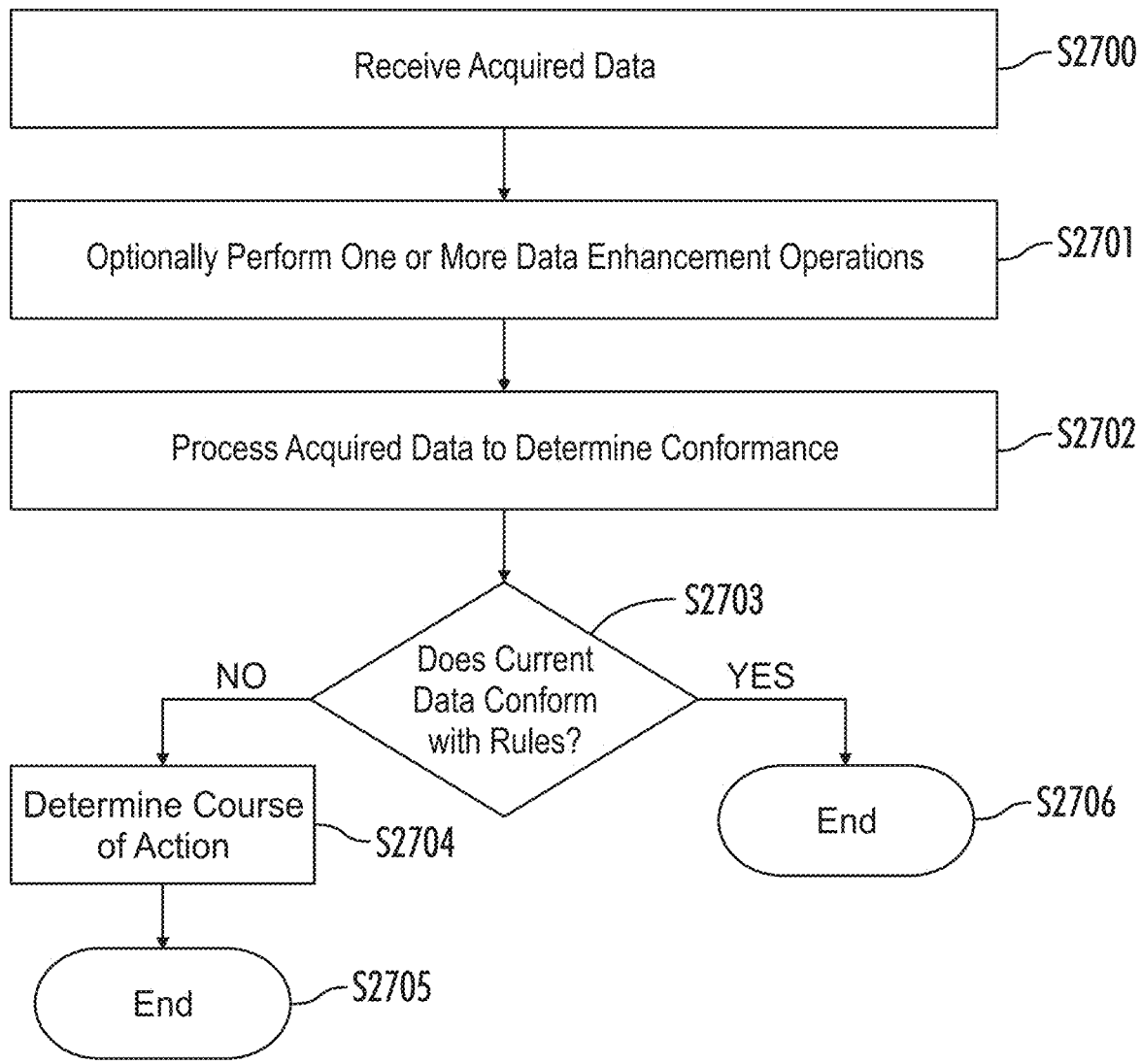
FIG. 27 illustrates a flowchart providing a process for performing data enhancement and conformance verification by a compliance service according to an exemplary embodiment.

FIG. 27 illustrates a flowchart providing a process for performing data enhancement and conformance verification by a compliance service according to an exemplary embodiment. The process begins at a step S2700, where acquired data is received by the compliance service. In one embodiment, the acquired data is received directly from the client electronic device 1900. However, the acquired data may be received or otherwise acquired by the compliance service from any other entity having access to the acquired data, without departing from the spirit and the scope of the present disclosure. The process continues to step S2701, where one or more data enhancement operations are optionally performed. The one or more data enhancement operations may include, for example, image processing for image data, video processing for video data, encryption/decryption for data, or any other form of processing which can be considered to enhance acquired data or to enhance the functioning and/or capabilities of the compliance service.

The process continues at step S2702, where acquired data is processed by the compliance service to determine medication compliance. Medication conformance may include, for example, pill count determination. The process continues to step S2703, where it is determined whether the processed acquired data indicated conformance with one or more rules associated with the acquired data (e.g., one or more rules relating to pill usage/count). If it is determined that the current data does not conform to one or more rules, the process continues to step S2704, where a course of action is determined (e.g., as described above with reference to step S2607). After the course of action is determined, undertaken, and/or completed, the process may end at step S2705. If it is determined that the current data conforms to the one or more rules, the process ends at step S2706.

Figure 28A:
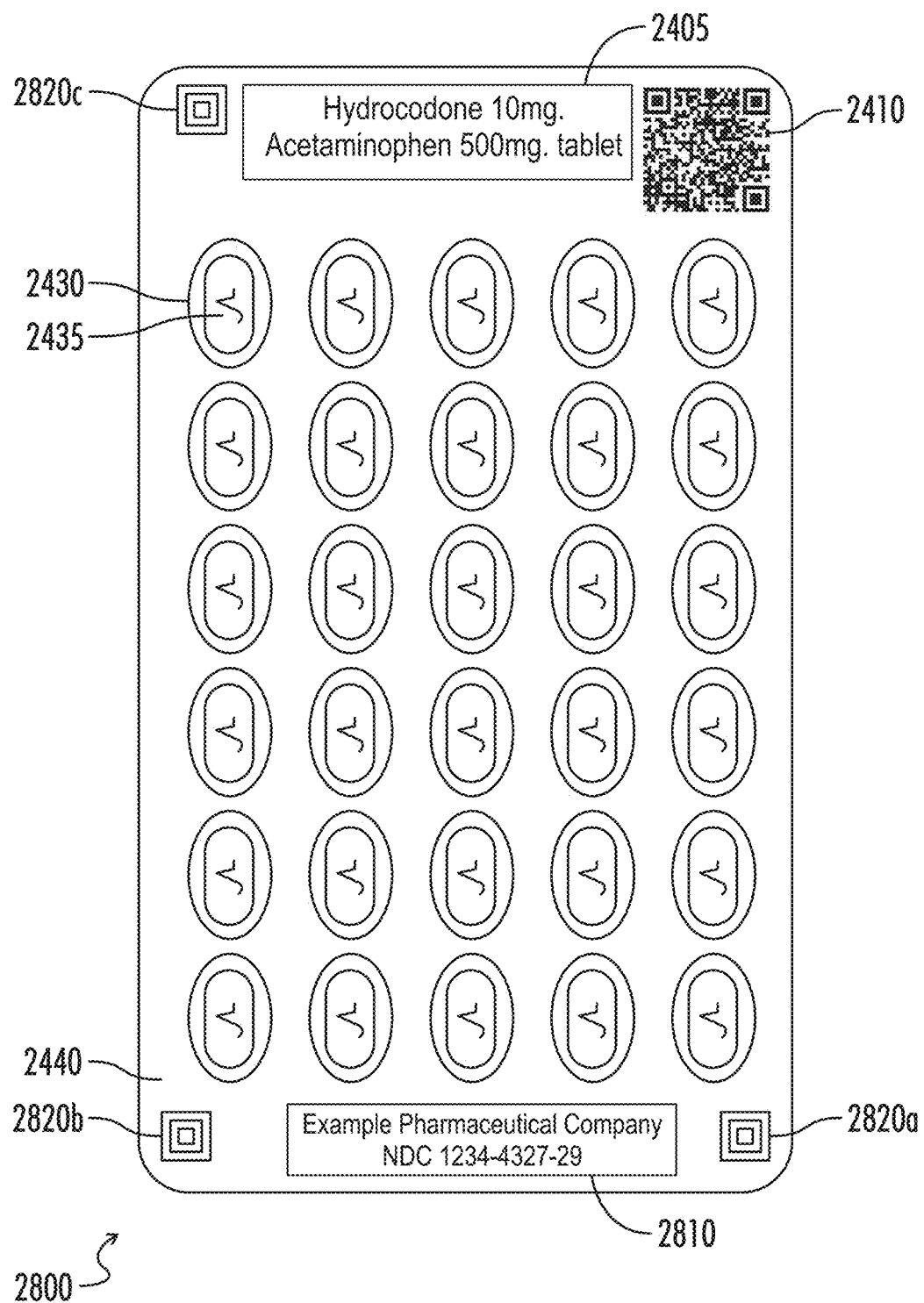
FIGS. 28A-B respectively illustrate a front-view and a rear-view of a blister packaging according an exemplary embodiment.
Figure 28B:
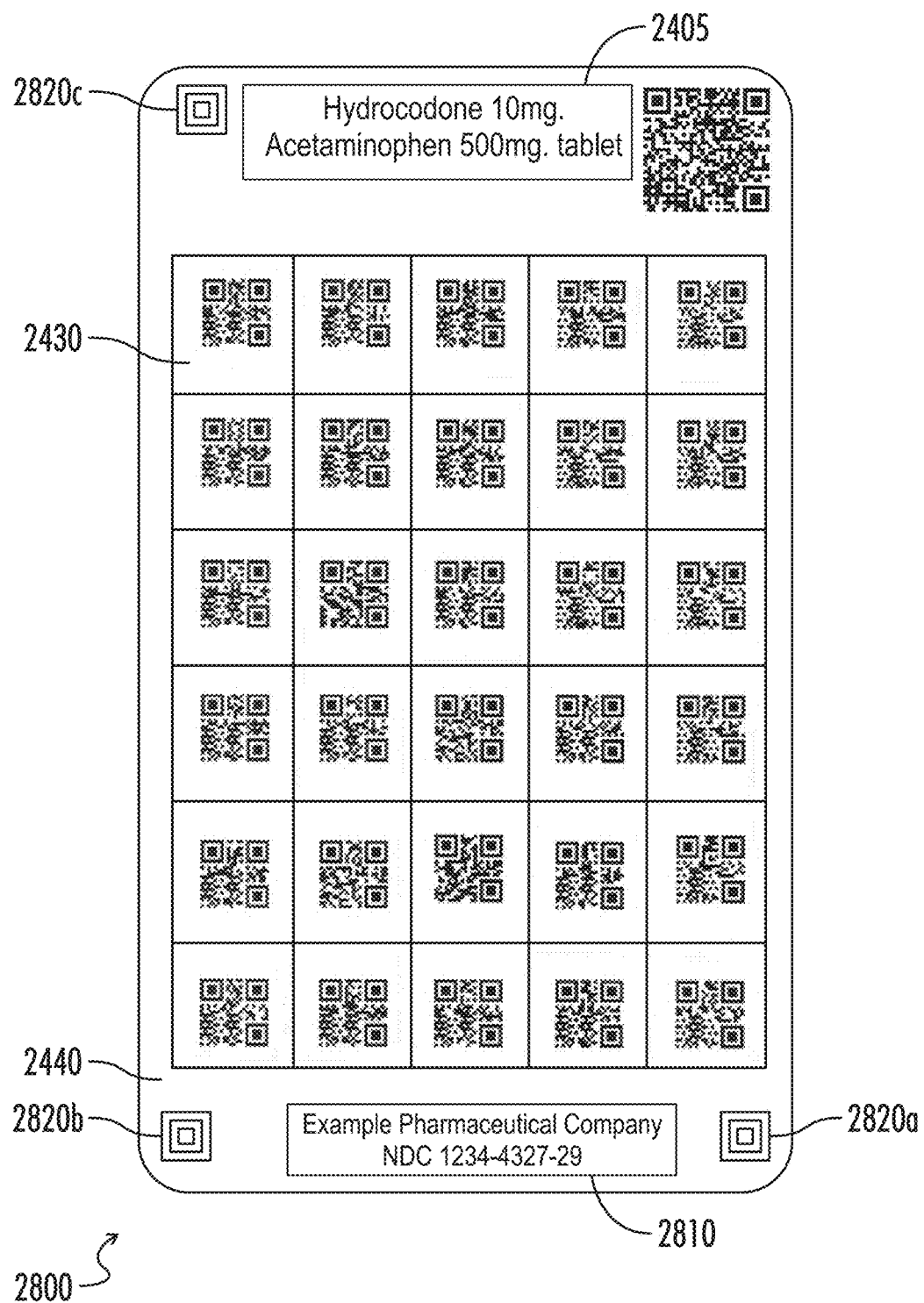

FIGS. 28A-B respectively illustrate a front-view and a rear-view of a blister packaging according to an exemplary embodiment. FIG. 28A illustrates a front-view of a blister packaging 2800 according an exemplary embodiment. Blister packaging 2800 includes one or more of the previously-described at least one information section 2405, an identifier 2410, one or more spaces 2430, at least one medication 2435, and a surface material 2440. The blister packaging 2800 may further include a second information section 2810. The second information section 2810 may include or otherwise convey any data or information relating to a prescription, a user, a provider, a professional, or any other data or information (in at least one of coded and non-coded form) consistent herewith. For example, in the embodiment illustrated in FIG. 28A, the second information section 2810 includes a pharmaceutical company name and an NDC number relating to the prescription(s) included in the blister packaging 2800.

The blister packaging 2800 may further include at least one registration markings 2820. Although illustrated as having three registration markings 2820a-c in FIG. 28A. It should be appreciated that a blister packaging 2800 consistent with the present disclosure may have no registration markings 2820, or any number of registration markings 2820. In one exemplary embodiment, at least one registration marking 2820 may be used to provide image or color adjustment information, to provide a spatial reference schema, to enable adjustment of rotation and/or tilt in perspective of any image, or any additional information usable by a user or device described herein. Further, one or more of the registration markings 2820 may include all or a portion of information intended to include or otherwise convey data. For example, in one exemplary embodiment, a first registration marking 2820a may include or otherwise be associated with a first information set, a second registration marking 2820b may include or otherwise be associated with a second information set, and a third registration marking 2820c may include or otherwise be associated with a third information set. In various embodiments, information associated with at least one registration marking 2820 may be used to assist in performing image or content processing relating to a pill counting operation.

FIG. 28B illustrates a rear-view of a blister packaging 2800 according to an exemplary embodiment. Like the front-view illustrated in FIG. 28A, the rear-side of blister packaging 2800 may include includes one or more of the previously-described at least one information section 2405, an identifier 2410, one or more spaces 2430, at least one medication 2435, and a surface material 2440. The blister packaging 2800 may further include a second information section 2810 and at least one registration marking 2820 as previously described. The blister packaging 2800 may include at least one unique identifier (such as a QR code as illustrated in FIG. 28B) associated with at least one of the one or more spaces 2430 consistent with uses described herein.

Figure 29A:
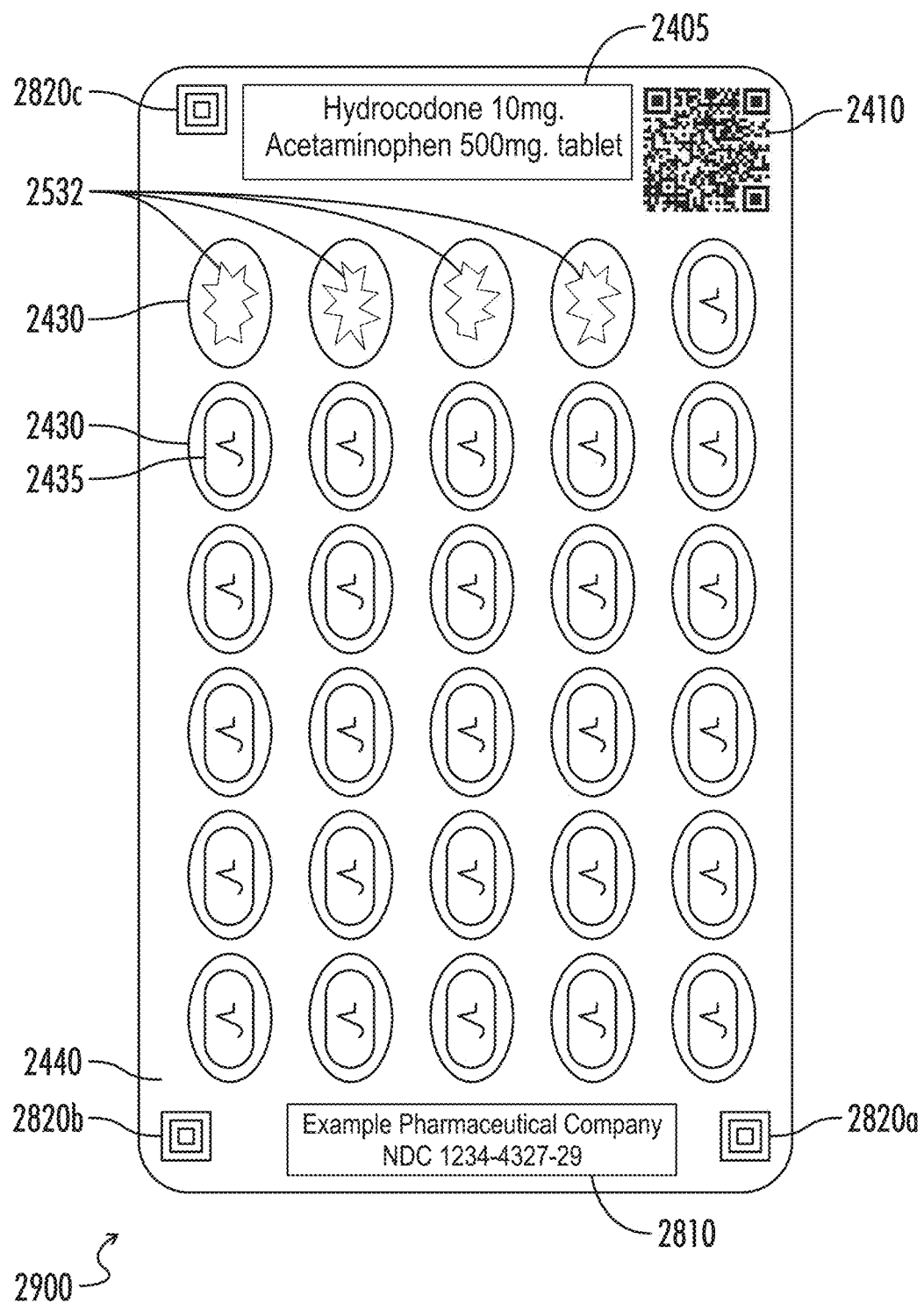
FIGS. 29A-B respectively illustrate a front-view and a rear-view of a blister packaging having pills removed in accordance with an exemplary embodiment.
Figure 29B:
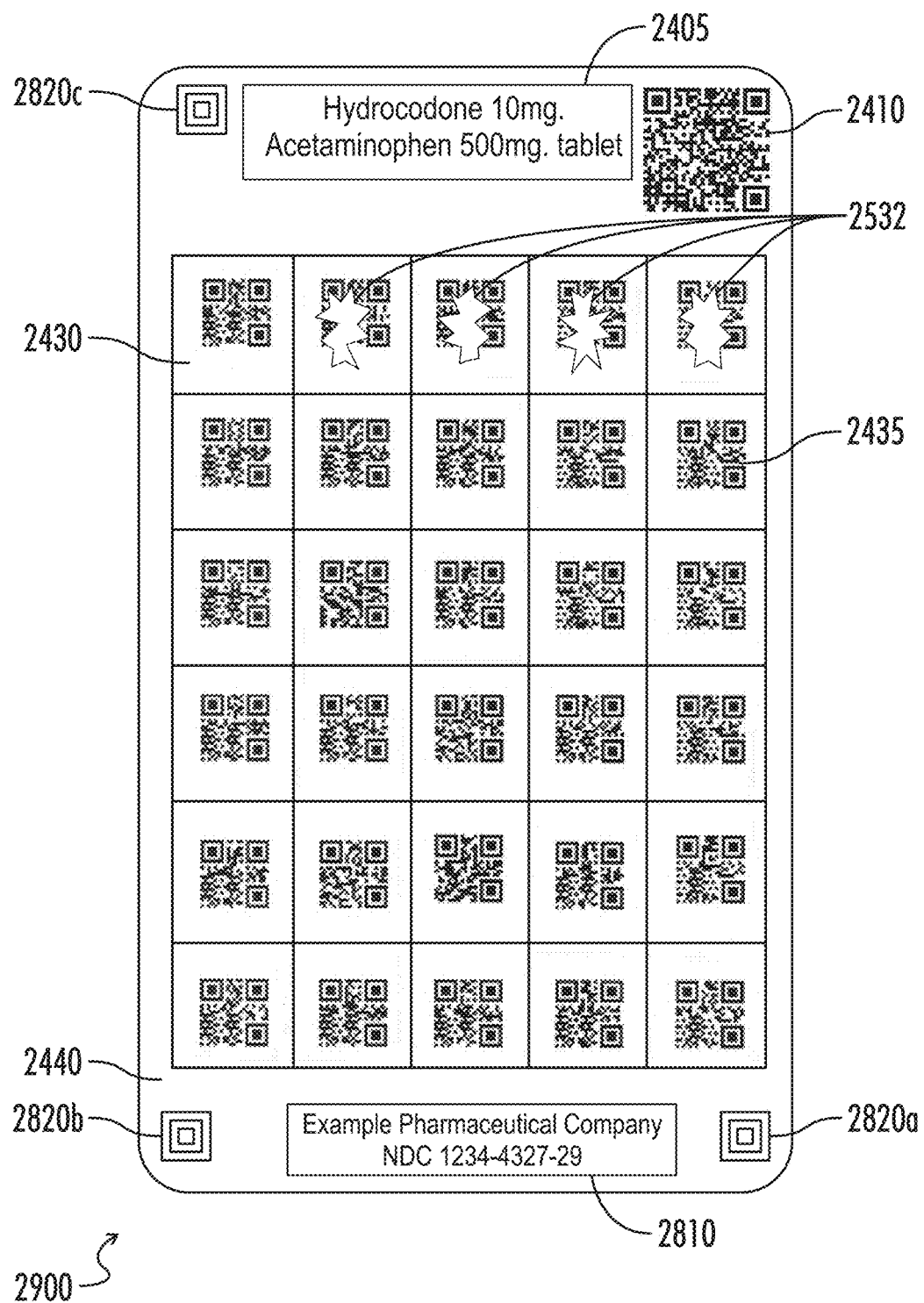

FIGS. 29A-B respectively illustrate a front-view and a rear-view of a blister packaging having pills removed in accordance with an exemplary embodiment. FIG. 29A illustrates a front-view of a blister packaging 2900 according to an exemplary embodiment. Like blister packaging 2800, the blister packaging 2900 includes one or more of the previously-described at least one information section 2405, an identifier 2410, one or more spaces 2430, at least one medication 2435, and a surface material 2440. The blister packaging 2800 may further include a second information section 2810 and at least one registration marking 2820 as previously described. The blister packaging 2900 illustrated by FIG. 29A includes four empty or tampered with spaces 2532. As shown in FIG. 29A and as previously described, a blister packaging 2900 may be configured so as to visually convey the absence and/or presence of one or more medications 2435 for use consistent with the present disclosure. The blister packaging 2900 may further be configured to visually convey a tampering status associated with at least one of the spaces 2430 and medication 2435.

FIG. 29B illustrates a rear-view of a blister packaging 2900 also having four empty or tampered with spaces 2532 consistent with FIG. 29A. As illustrated in FIG. 29B, at least a portion of one or more spaces 2430 may be configured to visually convey an absence and/or presence of one or more medications 2435. The blister packaging 2900 may further be configured to visually convey a tampering status associated with at least one of the spaces 2430 and medication 2435.

Although described with reference to one or more identifiers or information sets associated with a front or back-side of a blister packaging, it should be appreciated at least one of the identifiers and/or information sets may be present on a front surface of the blister packaging, on the back surface of the packaging, and/or a combination thereof. In one exemplary embodiment, a verification process may include capturing an image of both the front and rear sides of the blister packaging. In one exemplary embodiment, a material used as part of the blister packaging, the surface material 2440, or any part thereof may be transparent or otherwise visually indicate a presence or absence of medication within at least one space 2430 in addition to providing an identifier, such as a QR code. For example, at least a portion of the front side of the blister package 2900 may be transparent other than a bar code or QR code printed thereupon or thereunder.

In various exemplary embodiments, capture data may include user-generated images of prescription drugs and/or prescription drug containers, associated transmitted metadata, and data derived from subsequent processing. Images and data may be transmitted from a patient's device (e.g., via a smart phone operating as the client electronic device 1900) in a secure fashion to a secure server associated with the compliance service for processing.

Structured data may be realized from the patient's transmission in at least three ways. First, the sending application may explicitly transmit structured metadata that may include elements relating to the image, the sender, the sending application or the sending device. One benefit of the transmitted data is to ensure accurate, secure, un-tampered and non-repudiable data transmission. The second way that structured data may be realized from the patient's transmission is via interpretation of data encoded as images on the medication product packaging. Bar codes and QR codes are two examples of how structured data may be encoded in product labeling. The third method of generating structured data is via image analysis of the medication product itself.

Data resulting from each of these methods may be stored in a database as a component of the submission system. The submission system is configured to store at least one of the transmitted submission image, the metadata, the encoded data stored visually (e.g., via bar codes), the processed images, the structured or text-based results of image processing, and any messages generated related to the submission.

The submission storage system may flexibly support submitted, interpreted, and calculated data generated by processes that may change over time. The processes to generate stored submission data may be regulated by configuration data.

The system may be configured to allow the system to be flexibly configurable via data rather than programming to support evolution in design of encoded data on the medication package, calculated result sets, image processing protocols, messages, triggers, and events.

The system permits highly flexible definition and grouping of encoded data elements that can be applied to any system of graphical encoding such as bar codes or QR codes. The smallest component may be referred to as an "element". An element may be a single encoded field. An element can be named, assigned units, versioned and assigned status. Examples of elements that might be transmitted via interpretation of a graphical symbol include a globally unique identifier for a package or an RxNORM semantic clinical drug (SCD) identifier.

Coded data elements can be arranged into ordered sets that describe the expected fields in a graphically transmitted data set. Sets may be used to parse transmitted data into useful data elements. Sets may be versioned and assigned status. Elements may be used in multiple sets.

Image processing elements may include individual steps to be taken during the processing of an image. Examples of image processing elements include color thresholding, smoothing, and image masking Image processing protocols include ordered sets of image processing elements. An image processing protocol includes a series of steps to be undertaken in order to process a submitted image. Image processing protocols may be versioned and assigned status. Image processing protocols may be assigned to packaged medicinal products that contain medications with known image characteristics (e.g., round white 8 mm tablet). Image processing protocols may produce sets of intermediate and final results.

Result elements include individual datum that are created by image processing elements and protocols. Result elements are named and may have units. Elements are versioned and assigned status.

Result sets may be ordered groups of result elements. Result set definitions may be used to choreograph the output of image processing protocols. Result sets are versioned and assigned status.

Messages include communications sent from the system to various users, teams, and other actors. An example of a message is "potential overuse of hydrocodone detected." Messages may be assigned to one or more message classes from which they inherit urgency and subscribers. Messages can be expressed in different languages, are versioned and are assigned status.

Message classes are collections of similar messages. Messages within a message class may share a common target sophistication to allow for different levels of language complexity (e.g., directed at providers, consumers, or clerical staff). Messages within a class also share the same urgency and triggering event. An example of a message class might be "extremely urgent notification of hydrocodone overdose targeted at clinicians."

Triggering events are events that can be calculated from data resulting from image processing protocols and other relevant data from prescriptions and drug knowledge bases. Triggering events include specific definitions and rule logic. A simplified example of an event might be that the system has detected 5 untaken medication doses in a 72-hour period. Trigger events have urgency that may be defined in a medication specific manner.

Roles can be assigned to specific message classes allowing for tailoring of message receipt. For example, members of a patient's homecare team serving as emergency contacts may subscribe only to urgent messages in one embodiment.

The urgency of medication noncompliance can be defined by the extent and duration of noncompliance for any particular semantic clinical drug, indication, condition or patient-specific risk. For example, missing one or two doses of furosemide 40 mg tablet in a 7-10-day interval may be defined to be of mild urgency, but missing 3-4 doses in a 1-2-day interval may be defined to be of high urgency. Urgency definitions may be passed through to triggering events, message classes and messages.

Much of the workflow in exemplary embodiments of the system is modeled predicated upon on the idea of a person in a specific role. An individual person is tracked with basic demographic data sufficient to support probabilistic matching algorithms needed to share data with other HIT systems. People may also be assigned a preferred language in order to provide tailored messages and alerts. People may play many roles in the system depending on the context. For example, a person may be a patient in one context and a nurse in another.

Roles are an important concept within the compliance system. People may be assigned one or more roles from choices such as patient, home care giver, pharmacy technician, LPN and physician. Roles may be used in work flow and message flow.

Persons in a particular role, for example Dr. John Smith, can be assigned particular characteristics that vary with role including physical addresses, contact methods (phone, email, etc.) and surrogates. A surrogate is a person who "acts" in the place of the person in a particular role for a period of time (e.g., physician coverage for Dr. Smith while he is on vacation). Persons in a role can also be assigned as an owner of a particular calendar. One important person role characteristics supported by the system is team membership, where available.

The system supports the highly flexible creation and implementation of at least two distinct types of teams—Homecare teams and Healthcare teams.

Homecare teams are patient centered—a person in the patient role is explicitly included in the team definition. Other homecare team members are assigned to be members of a specific patient's homecare team in particular roles. Assignment can be time limited. A patient's homecare team member may also elect an alert sensitivity for that particular patient. For example, a parent may elect high sensitivity for alerts (e.g., receive all) and a friend may only elect to receive urgent alerts. Contact methods and addresses for each homecare team member may be inherited from the person-role assignment. Homecare teams can be calendar owners, making sharing timed events easily accomplished for all homecare team members.

Healthcare teams are primarily provider team-centered (versus patient-centered) in their underlying modeling. This is because healthcare teams, e.g., staff at a solo private practice, can be expected to care for many patients while still having the same basic roles, contacts, addresses, and other features. Healthcare teams are flexibly configured to allow multiple members in varying roles and different addresses. Various methods of contacting the teams are allowed in addition to person-role specific addresses and contacts. Healthcare teams can be calendar owners. Healthcare teams are specifically assigned to patients in a many-to-many fashion. The assignment can be time limited. Healthcare teams and their members can set alert sensitivities for a particular patient or for their specific role on the healthcare team.

Contacts and addresses can be assigned to any specific person-role combination or healthcare team in a one-to-many manner. Contact methods specify channels and channel specific connection data such as "work email" and an SMTP email address or "text messaging" with an SMS address. Addresses may be used to specify physical locations.

Calendars are an underlying core component of the end-to-end compliance system. Calendars may be used to manage events, such as upcoming medication compliance check "appointments". For example, Mr. Doh is scheduled to send an image of his hydrocodone blister pack this Thursday between 5 pm and 9 pm. Calendars can be assigned to people in particular roles, or assigned to homecare teams and healthcare teams.

Prescription Data is an element of the medication compliance system. Prescription data of several types can be managed, including prescription "orders" from the prescribing clinician, prescription "orders" from a pharmacy perspective, including dispensing over time, data about each time medication are dispensed, and data about each package of medicinal products dispensed to the patient. Data regarding drug use evaluations may also be included in the prescription data section. These tables and fields may be compatible with NCPDP Script to the greatest extent possible.

In operation, each user, clinician, or any other individual or group capable of interacting with the disclosed system may have an individual or group login identifier and optional password. Each individual or group login identifier and password may be created either automatically or specified by a user upon a first visit to the portal or may be generated and/or imported via a third-party means (such as o-auth 2.0 or other authorization and/or authentication scheme). One or more individual or group accounts or settings, prescription information, compliance event scheduling, and/or invitations to use the system may be created or edited by any user of the system provided appropriate rights. The system may further permit compliance review by at least one of an individual and a group having appropriate access rights. For example, authorized users may access both raw and processed textual, graphical, or any other data associated with a user's compliance history.

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A system for automated medication compliance assurance for a patient, the system comprising:
   a portal configured to receive monitoring data relating to the patient from at least one of a healthcare provider, a pharmacist, or a pill provider and to transmit a monitoring plan request responsive to the received monitoring data relating to the patient received from the at least one healthcare provider, pharmacist, or pill provider;
   a compliance service configured to receive the monitoring plan request, the compliance service being further configured to generate and store a monitoring schedule based on the received monitoring plan request, the monitoring schedule including a scheduled pill count operation, the compliance service configured to transmit at least a portion of the monitoring schedule to a device of a user associated with the monitoring schedule; and
   an electronic device having a data capture apparatus, the data capture apparatus being configured to obtain data associated with a medication container, the medication container being configured to provide indicia associated with a state of at least a portion of the medication container, wherein the data capture apparatus comprises an image capture device, and wherein the indicia comprises computer-detectable visual indicia at a surface of the at least a portion of the medication container useable to detect evidence of a presence or absence of at least one pill of the medication container,
   wherein the compliance service is further configured (i) to perform a processing operation on the obtained data associated with the medication container, the processing operation including at least one of (i) a deterministic morphological image analysis operable to identify at least one contiguous pixel collection in relation to the monitoring plan request, or (ii) a machine classification image analysis including a learning operation and classification operation based at least in part upon a number of pills, a percentage of use, or an image quality in relation to the monitoring plan request, and (ii) to determine a patient medication usage metric associated with the scheduled pill count operation, the medication usage metric based at least in part on an analysis of the data associated with the medication container including the detected evidence of the presence or absence of at least one pill of the medication container, and
   wherein the compliance service is configured to determine a medication compliance status by comparing the patient medication usage metric to an expected utilization associated with the monitoring schedule, and is further configured to selectively determine a course of action based at least in part upon the medication compliance status and to selectively escalate the course of action based at least in part upon a status of the course of action, the selectively escalated course of action includes at least one of transmitting a scheduling communication or requiring that the data capture apparatus of the electronic device capture additional data associated with the medication container.

2. The system of claim 1, wherein the portal is configured to receive the monitoring data from at least one clinician.

3. The system of claim 1, wherein the medication container comprises at least one identifier, and wherein the compliance service is configured to determine the patient medication usage metric at least in part based upon the at least one identifier.

4. The system of claim 3, wherein the identifier comprises a Quick Response (QR) code, wherein the data capture apparatus is configured to capture an image of the medication container including the QR code.

5. The system of claim 1, wherein the electronic device is a mobile device and the data capture apparatus comprises a camera associated with the mobile device, at least one of the mobile device and the data capture apparatus being configured to associated one or more sets of metadata with a captured image or video.

6. The system of claim 1, wherein the indicia includes at least one of a QR code or a bar code, and wherein the indicia is configured to be placed on at least one of a front surface and a rear surface of the medication container.

7. The system of claim 1, wherein the scheduled pill count operation is a randomly scheduled pill count operation not previously known to the patient.

8. A method of providing patient medication compliance assurance, the method comprising:
   receiving monitoring data relating to the patient from at least one of a healthcare provider, a pharmacist, or a pill provider;
   transmitting a monitoring plan request to a compliance service responsive to the received monitoring data relating to the patient received from the at least one healthcare provider, pharmacist, or pill provider;
   receiving the monitoring plan request at the compliance service and generating a monitoring schedule based at least in part upon the received monitoring plan request, the patient monitoring schedule including a scheduled pill count operation;
   transmitting at least a portion of the monitoring schedule to a device associated with the patient;
   obtaining data associated with a medication container by an electronic device configured to provide indicia associated with a state of at least a portion of the medication container, wherein the obtaining data associated with the medication container includes capturing at least one image of the medication container using an image capture device of the electronic device, and wherein the indicia comprises computer-detectable visual indicia at a surface of the at least a portion of the medication container useable to detect evidence of a presence or absence of at least one pill of the medication container;

determining a patient medication usage metric associated with the scheduled pill count operation, the medication usage metric based at least in part upon an analysis of the data associated with the medication container including the detected evidence of the presence or absence of at least one pill of the medication container using at least one of (i) a deterministic morphological image analysis operable to identify at least one contiguous pixel collection in relation to the monitoring plan request, or (ii) a machine classification image analysis including a learning operation and classification operation based at least in part upon a number of pills, a percentage of use, or an image quality in relation to the monitoring plan request;

determining a medication compliance status by comparing the patient medication usage metric to an expected utilization associated with the monitoring schedule; and selectively determining a course of action based at least in part upon the medication compliance status and to selectively escalate the course of action based at least in part upon a status of the course of action, the selectively escalated course of action including at least one of transmitting a scheduling communication or requiring that the electronic device capture additional data associated with the medication container.

9. The method of claim 8, further comprising:
receiving the monitoring data from at least one clinician.

10. The method of claim 8, further comprising:
determining the patient medication usage metric based at least in part upon at least one identifier associated with the medication container.

11. The method of claim 10, further comprising:
capturing an image of the medication container including a Quick Response (QR) code.

12. The method of claim 8, further comprising:
using a mobile device to function as the electronic device, wherein the obtaining data associated with the medication container comprises capturing an image of the medication container using a camera of the mobile device.

13. The method of claim 8, further comprising:
placing the indicia on at least one of a front surface and a rear surface of the medication container, wherein the indicia includes at least one of a QR code and a bar code.

14. The method of claim 8, further comprising:
determining a notification status based at least in part upon the determined medication compliance status;
selecting at least one notification based upon the notification status, the notification being associated with at least one receiver; and
communicating the at least one notification to the at least one receiver according to the determined notification status.

15. The method of claim 14, wherein the notification status comprises a status associated with a second or subsequent non-conformance, and wherein the at least one notification comprises an escalated notification based upon the second or subsequent non-conformance.

16. The method of claim 14, wherein the at least one receiver comprises at least one of a doctor, a nurse, a pharmacist, or a person or service associated with prescribing or monitoring patient medication conformance.

17. An apparatus for providing medication compliance service assurance for a patient, the apparatus comprising:
a communications unit configured to receive a monitoring plan request relating to the patient from at least one of a healthcare provider, a pharmacist, or a pill provider and to obtain data associated with a medication container from an electronic device, the data containing an identifier associated with a state of at least a portion of the medication container, wherein obtaining the data associated with the medication container includes capturing at least one image of the medication container using an image capture device, and further wherein the identifier comprises computer-detectable visual indicia at a surface of the at least a portion of the medication container useable to detect evidence of a presence or absence of at least one pill of the medication container; and
a data processing component configured to:
(i) generate a monitoring schedule based on the received monitoring plan request, the monitoring schedule including a scheduled pill count operation;
(ii) transmit at least a portion of the monitoring schedule to a device associated with the patient;
(iii) determine a patient medication usage metric associated with the scheduled pill count operation, the medication usage metric based at least in part upon an analysis of the data associated with the medication container including the detected evidence of the presence or absence of at least one pill of the medication container using at least one of (i) a deterministic morphological image analysis operable to identify at least one contiguous pixel collection in relation to the monitoring plan request, or (ii) a machine classification image analysis including a learning operation and classification operation based at least in part upon a number of pills, a percentage of use, or an image quality in relation to the monitoring plan request;
(iv) determine a medication compliance status by comparing the patient medication usage metric to an expected utilization associated with the monitoring schedule; and
(v) selectively determine a course of action based at least in part upon the medication compliance status and selectively escalating the course of action based at least in part upon a status of the course of action, the selectively escalated course of action including at least one of transmitting a scheduling communication or transmitting a requirement that the electronic device capture additional data associated with the medication container.

18. The apparatus of claim 17, wherein the data processing component is configured to determine the patient medication usage metric based at least in part upon the at least one identifier.

19. The apparatus of claim 17, wherein the communications unit is configured to receive the medication data including a Quick Response (QR) code, and wherein the data processing component is configured to process the received medication data to identify the QR code.

20. The apparatus of claim 19, wherein the data processing component is configured to determine the patient medication usage metric based at least in part upon the identified QR code.

21. The apparatus of claim 20, wherein the data processing component is further configured to determine and to implement at least one course of action when the comparison of the patient medication usage metric to the expected utilization associated with the monitoring schedule indicates a noncompliance status.

* * * * *